(12) United States Patent
Andrews et al.

(10) Patent No.: US 7,928,099 B2
(45) Date of Patent: Apr. 19, 2011

(54) PYRIMIDO [4,5-D] AZEPINE DERIVATIVES AS 5-HT$_{2c}$ AGONISTS

(75) Inventors: Mark Andrews, Sandwich (GB); Julian Blagg, Sandwich (GB); Paul Brennan, Sandwich (GB); Paul Fish, Sandwich (GB); R. Ian Storer, Sandwich (GB); Gavin Whitlock, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 12/532,715

(22) PCT Filed: Mar. 14, 2008

(86) PCT No.: PCT/IB2008/000731
§ 371 (c)(1),
(2), (4) Date: Oct. 22, 2009

(87) PCT Pub. No.: WO2008/117169
PCT Pub. Date: Oct. 2, 2008

(65) Prior Publication Data
US 2010/0113422 A1    May 6, 2010

Related U.S. Application Data

(60) Provisional application No. 60/896,527, filed on Mar. 23, 2007.

(51) Int. Cl.
*A61P 15/00*    (2006.01)
*A61P 25/00*    (2006.01)
*A61K 31/55*    (2006.01)
*C07D 487/04*    (2006.01)

(52) U.S. Cl. ........................................ 514/215; 540/578

(58) Field of Classification Search .................. 514/215; 540/578
See application file for complete search history.

(56) References Cited

U.S. PATENT DOCUMENTS

2007/0032481 A1    2/2007    Dvorak et al. ............. 514/227.8
2007/0225275 A1    9/2007    Allison et al. ................ 514/215

FOREIGN PATENT DOCUMENTS

| EP | 1552842 | 7/2005 |
|----|---------|--------|
| WO | WO 2006044762 | 4/2006 |
| WO | WO 2007019083 | 2/2007 |
| WO | WO 2007109355 | 9/2007 |
| WO | WO 2007146122 | 12/2007 |

*Primary Examiner* — Brenda L Coleman
(74) *Attorney, Agent, or Firm* — Jennifer A. Kispert; John A. Wichtowski

(57) ABSTRACT

The present invention provides a compound of formula (I):

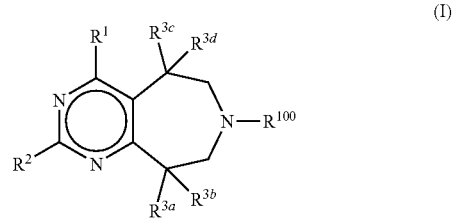

or a pharmaceutically acceptable salt thereof wherein the variables $R^1$, $R^2$, $R^{3a}$, $R^{3b}$, $R^{3c}$, $R^{3d}$, and $R^{100}$ are as defined herein. The invention is also directed to pharmaceutical compositions comprising the compounds of formula (I) and methods of treating a 5-HT$_{2c}$ receptor-mediated disorders with a compound of formula (I) or a pharmaceutical composition comprising a compound of formula (I).

11 Claims, No Drawings

PYRIMIDO [4,5-D] AZEPINE DERIVATIVES AS 5-HT$_{2c}$ AGONISTS

This application is a national stage filing of PCT/IB2008/000731 filed Mar. 14, 2008, which claims the benefit of Provisional Patent Application No. 60/896,527 filed Mar. 23, 2007.

This invention relates to fused azepine derivatives potentially useful in medicine. More particularly, this invention relates to pyrimidine-fused azepine derivatives and to processes for the preparation of, intermediates used in the preparation of, compositions containing and the uses of, such derivatives.

The fused azepine derivatives of the present invention are modulators (preferably agonists) of the 5-HT receptor, preferably the 5-HT$_{2c}$ receptor. 5-HT$_{2c}$ receptor modulators/agonists are believed to have a number of therapeutic applications, particularly in the treatment of sexual dysfunction, schizophrenia, cognitive deficits including cognitive deficits associated with schizophrenia, anxiety, depression, obsessive-compulsive disorder, epilepsy, obesity, and LUTS, among others. Preferably, the modulators/agonists are selective for the 5-HT$_{2c}$ receptor over other 5-HT receptors.

Bishop, M. J. and Nilsson, B. M., "New 5-HT$_{2c}$ Receptor Agonists" Expert Opin. Ther. Patents, 2003, 13(11): 1691-1705, review patent applications that describe compounds having agonist activity at the 5-HT$_{2c}$ receptor. The review also addresses indications for which evidence exists to support the use of 5-HT$_{2c}$ agonists in their treatment, such as obesity, schizophrenia, anxiety, depression, obsessive-compulsive disorder, sexual dysfunction, epilepsy, and urinary incontinence, among others. Toxicity and non-selectivity of ligands for the various 5-HT receptors remain a challenge. It is suspected that the non-selectivity of some ligands contributes to various adverse side effects such as hallucinations and cardiovascular complications. Therefore, there remains a need for 5-HT$_2$, selective receptor ligands.

It has now been found that compounds of the present invention are modulators, preferably, agonists of the 5-HT$_{2c}$ receptor, preferably selective agonists for this receptor over other 5-HT receptors. The compounds of the present invention are therefore potentially useful in the treatment of a wide range of disorders, particularly in the treatment of 5-HT$_{2c}$ receptor-mediated disorders in animals including humans. The treatment of female sexual dysfunction (FSD) is a preferred use. All forms of female sexual dysfunction (FSD) are potentially treatable with the compounds of the present invention including female sexual arousal disorder (FSAD), female orgasmic disorder (FOD), hypoactive sexual desire disorder (HSDD), or sexual pain disorder. The treatment of male sexual dysfunction, particularly male erectile dysfunction (MED), is another preferred use. Other preferred uses of the present invention include treatment of eating disorders, promotion of weight loss, control of weight, or treatment of obesity. Other conditions that may be treated with the compounds of the present invention include psychoses, schizophrenia, schizophreniform disorder, schizoaffective disorder, delusional disorder, substance-induced psychotic disorder, personality disorder of the paranoid type, or personality disorder of the schizoid type. Compounds of the present invention may also be used for the treatment of dementia, cognitive deficit symptoms of Alzheimer's disease, attention deficit symptoms of Alzheimer's disease, multi-infarct dementia, alcoholic dementia or other drug-related dementia, dementia associated with intracranial tumors or cerebral trauma, dementia associated with Huntington's disease or Parkinson's disease, AIDS-related dementia, delirium, amnestic disorder, post-traumatic stress disorder, mental retardation, a learning disorder, attention-deficit/hyperactivity disorder, age-related cognitive decline, cognitive deficits associated with psychoses, or cognitive deficits associated with schizophrenia. Conditions that may be treated with the compounds of the present invention also include benign prostactic hyperplasia, overactive bladder or LUTS.

The terms "treating", "treat", or "treatment" as used herein are intended to embrace both prevention and control i.e., prophylactic, and palliative treatment of the indicated conditions.

Various pyrimidoazepine derivatives useful for the treatment of diseases associated with the 5-HT$_{2c}$ receptor are referred to in WO2006044762. Pyrimidine fused heterocycles useful for the treatment of diseases associated with leucocyte activation are referred to in US2003191143. N-containing heterocyclic compounds useful for the treatment of diseases such as thrombosis, ischemic heart disease, cerebrovascular disorder, circulatory disorders, migraine, diabetic peripheral nerve disorder and neuralgia afer herpes zoster are disclosed in JP11171865. JP2005162673A refers to quaternary ammonium salts of bicyclic pyrimidine derivatives useful for the treatment of inflammation and allergic and autoimmune diseases. International Patent Application publication number WO2007019083 refers to pyrimidine fused compounds as 5-HT receptor modulators.

There is a need to provide new 5-HT$_{2c}$ agonists that are good drug candidates. In particular, preferred compounds should bind potently to the 5-HT$_{2c}$ receptor whilst showing little affinity for other receptors and show functional activity as agonists. They should be well absorbed from the gastrointestinal tract, be metabolically stable and possess favourable pharmacokinetic properties. When targeted against receptors in the central nervous system they should cross the blood brain barrier freely and when targeted selectively against receptors in the peripheral nervous system they should not cross the blood brain barrier. They should be non-toxic and demonstrate few side-effects. Furthermore, the ideal drug candidate will exist in a physical form that is stable, non-hygroscopic and easily formulated.

In particular, compounds of the present invention are selective agonists of the 5-HT$_{2c}$ receptor. Advantageously, compounds of the invention show little or no affinity for the 5-HT$_{2a}$ and 5-HT$_{2b}$ receptors. In addition, preferred compounds of the invention are metabolically stable.

The present invention therefore provides a compound of formula (I):

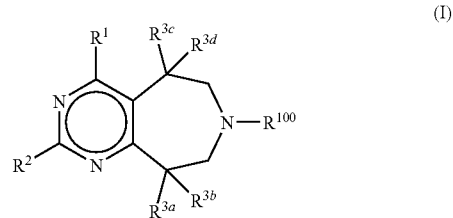

or a pharmaceutically acceptable salt, solvate (including a hydrate), or prodrug thereof, wherein:

$R^1$ is H, $(C_1-C_4)$alkyl, fluoro$(C_1-C_4)$alkyl, $(C_3-C_6)$cycloalkyl, fluoro$(C_3-C_6)$cycloaolkyl, fluoro$(C_1-C_4)$alkoxy, $-NR^4R^5$, $-OR^{10}$, or Het$^1$, said alkyl, cycloalkyl and alkoxy being optionally substituted by one or more hydroxyl;

Het$^1$ is a 5- or 6-membered heterocyclic ring containing one nitrogen atom at the point of attachment, and comprising up to 2 further heteroatoms selected from oxygen, nitrogen and sulphur, said ring being optionally substituted by 1 to 3 groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl;

$R^2$ is —($CH_2$)$_p$-phenyl, —CH($R^6$)-phenyl, —C($R^6$)$_2$-phenyl, —NR$^7$R$^8$, or —NR$^9$—($CH_2$)$_p$-phenyl wherein in each instance the phenyl radical is optionally substituted by up to four groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl;

$R^{3a}$, $R^{3b}$, $R^{3c}$ and $R^{3d}$ are independently H, ($C_1$-$C_4$)alkyl or fluoro($C_1$-$C_4$)alkyl;

$R^4$ is H, ($C_1$-$C_4$)alkyl or fluoro($C_1$-$C_4$)alkyl;

$R^5$ is ($C_1$-$C_6$)alkyl, fluoro($C_1$-$C_6$)alkyl, ($C_3$-$C_6$)cycloalkylmethyl, fluoro($C_3$-$C_6$)cycloalkylmethyl, said alkyl and cycloalkyl being optionally substituted by one or more hydroxyl, phenyl, or —($CH_2$)$_q$-Het$^2$;

Het$^2$ is a 5-membered heterocyclic ring containing 1 or 2 heteroatoms independently selected from nitrogen and oxygen, said ring being optionally substituted by 1 to 3 groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl;

each $R^6$ is independently ($C_1$-$C_4$)alkyl, fluoro($C_1$-$C_4$)alkyl, hydroxyl, or fluorine; when $R^2$ is —C($R^6$)$_2$-phenyl, both $R^6$ can be taken together to form a ($C_3$-$C_6$)cycloalkyl or a fluoro($C_3$-$C_6$)cycloalkyl group with the carbon atom to which they are bound;

$R^7$ is H, ($C_1$-$C_4$)alkyl, fluoro($C_1$-$C_4$)alkyl, ($C_3$-$C_6$)cycloalkyl or fluoro($C_3$-$C_6$)cycloalkyl;

$R^8$ is ($C_1$-$C_4$)alkyl, fluoro($C_1$-$C_4$)alkyl, ($C_3$-$C_6$)cycloalkyl, ($C_3$-$C_6$)cycloalkylmethyl, or fluoro($C_3$-$C_6$)cycloalkyl;

or $R^7$ and $R^8$, together with the nitrogen atom to which they are bound, form a 4- to 6-membered heterocyclic ring optionally comprising 1 further heteroatom selected from oxygen and sulphur, said ring being optionally fused to a phenyl ring;

$R^9$ is H, ($C_1$-$C_4$)alkyl or fluoro($C_1$-$C_4$)alkyl;

$R^{10}$ is ($C_1$-$C_4$)alkyl optionally substituted by —($C_3$-$C_6$)cycloalkyl, —($C_1$-$C_4$)alkoxy, —$CF_3$, —N[($C_1$-$C_4$)alkyl]$_2$, phenyl optionally substituted by cyano, or Het$^3$;

Het$^3$ is a 5- or 6-membered heterocyclic ring containing 1 or 2 heteroatoms independently selected from nitrogen and oxygen, said ring being optionally substituted by ($C_1$-$C_4$)alkyl;

p is 1 or 2;

q is 0, 1 or 2;

and $R^{100}$ is H or a NH prodrug moiety, such as are described in Fleischer et al, *Advanced Drug Delivery Reviews*, 19(1996), 115-130, e.g. $CO_2R^{101}$ wherein $R^{101}$ is a $C_{1-10}$ alkyl group and C(O)$R^{102}$ wherein $R^{102}$ is a $C_{1-10}$ alkyl group.

In the description and appended claims, the term "alkyl" refers to a straight-chain or branched-chain saturated aliphatic hydrocarbon radical containing the specified number of carbon atoms. Examples of alkyl radicals include methyl, ethyl, n-propyl, isopropyl, n-butyl, isobutyl, sec-butyl, tert-butyl.

The term "cycloalkyl" refers to a carbocyclic ring containing the specified number of carbon atoms. Examples of carbocyclic rings include cyclopropyl, cyclobutyl, cyclopentyl, cyclohexyl.

The terms "fluoroalkyl", "fluoralkoxy", "fluorocycloalkyl" refer to alkyl, alkoxy and cycloalkyl radicals which can have any number of fluorine atoms as substituents. Particularly preferred radicals include perfluoroalkyl, perfluoroalkoxy and perfluorocycloalkyl, for example, $CF_3$.

The term "alkoxy" refers to a radical OR where R is an alkyl as defined above. Examples of alkoxy include methoxy, ethoxy, n-propoxy, i-propoxy, n-butoxy, i-butoxy, sec-butoxy and t-butoxy.

The term "halogen" refers to fluorine, chlorine, bromine or iodine.

The terms "Het$^1$" and "Het$^2$" refer to heterocyclic rings as defined above. Each ring is saturated, partially unsaturated or aromatic. When the heterocyclic ring contains one or more available nitrogen atoms, N-oxides are included within the scope of the invention.

Examples of saturated or partially unsaturated heterocyclic groups at Het$^1$ include pyrrolidine, pyrazolidine, imidazolidine, thiazolidine, isoxazolidine, piperidine, piperazine, morpholine, thiomorpholine.

Examples of saturated or partially unsaturated heterocyclic groups at Het$^2$ include pyrrolidine, tetrahydrofuran, pyrazolidine, imidazolidine, isoxazolidine.

Examples of aromatic heterocyclic groups at Het$^2$ include pyrrole, imidazole, pyrazole, oxazole, isoxazole. Examples of aromatic heterocyclic groups at Het$^1$ include those of Het$^2$ and triazole, pyridine, pyrazine, pyrimidine, pyridazine, thiadiazine, thiazole, isothiazole, oxadiazole, thiadiazole.

Preferably, $R^{3a}$ is H or methyl. More preferably, $R^{3a}$ is H. Preferably, each $R^{3b}$, $R^{3c}$ and $R^{3d}$ is H.

In an alternative embodiment, $R^{3c}$ is preferably H or methyl. More preferably, $R^{3c}$ is H.

Preferably each $R^{3a}$, $R^{3b}$ and $R^{3d}$ is H.

In one preferred embodiment, $R^1$ is H, ($C_1$-$C_4$)alkyl, fluoro($C_1$-$C_4$)alkyl, ($C_3$-$C_6$)cycloalkyl, fluoro($C_3$-$C_6$)cycloalkyl, ($C_1$-$C_4$)alkoxy, fluoro($C_1$-$C_4$)alkoxy, —NR$^4$R$^5$, or Het$^1$, said alkyl, cycloalkyl and alkoxy being optionally substituted by one or more hydroxyl.

In a further preferred embodiment, $R^1$ is H, ($C_1$-$C_4$)alkyl, ($C_3$-$C_6$)cycloalkyl, ($C_1$-$C_4$)alkoxy, —NR$^4$R$^5$, or Het$^1$.

$R^1$ more preferably is H, ($C_1$-$C_4$)alkyl, ($C_1$-$C_4$)alkoxy, —NR$^4$R$^5$, or Het$^1$.

In one preferred embodiment, Het$^1$ is a 5- or 6-membered heterocyclic ring containing one nitrogen atom at the point of attachment, and further comprising either (a) 0, 1 or 2 nitrogen atoms or (b) one oxygen atom, said ring being optionally substituted by 1 to 3 groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl. More preferably Het$^1$ is a 5- or 6-membered heterocyclic ring containing one nitrogen atom at the point of attachment, and further comprising either (a) 0 or 1 nitrogen atom or (b) one oxygen atom, said ring being optionally substituted by 1 to 3 groups selected from amino, —NH[($C_1$-$C_4$)alkyl], —N[($C_1$-$C_4$)alkyl]$_2$, hydrogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

Yet more preferably, Het$^1$ is N-linked and is selected from pyrrolidine, piperidine, imidazole, pyrazole, pyridine and morpholine, each of which being optionally substituted by 1 to 3 groups selected from hydroxyl, halogen, cyano, ($C_1$-$C_4$)

alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

Most preferably, $Het^1$ is N-linked and is selected from pyrrolidine, imidazole, pyrazole and morpholine, each of which being optionally substituted by 1 to 3 groups selected from hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

In a further aspect, $R^1$ is preferably H, ($C_1$-$C_4$)alkyl or ($C_1$-$C_4$)alkoxy. More preferably, $R^1$ is H or ($C_1$-$C_4$)alkoxy. Most preferably, $R^1$ is H.

In a further aspect, $R^1$ is preferably —$NR^4R^5$ and $R^5$ is ($C_1$-$C_6$)alkyl, said alkyl being optionally substituted by hydroxyl.

In a yet further aspect, $R^1$ is preferably —$NR^4R^5$ and $R^5$ is ($C_3$-$C_6$)cycloalkylmethylene, said cycloalkyl being optionally substituted by hydroxyl.

In an alternative aspect, $R^1$ is preferably —$NR^4R^5$, $R^5$ is —$(CH_2)_q$-$Het^2$ and $Het^2$ is tetrahydrofuran optionally substituted by 1 to 3 groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

More preferably, $Het^2$ is tetrahydrofuran-2-yl, optionally substituted by 1 to 3 groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

In another aspect, $R^1$ is preferably —$NR^4R^5$, $R^5$ is —$(CH_2)_q$-$Het^2$ and $Het^2$ is pyrazole, optionally substituted by 1 to 3 groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

More preferably, $Het^2$ is pyrazol-1-yl, optionally substituted by 1 to 3 groups selected from amino, —NH[($C_1$-$C_4$)alkyl], —N[($C_1$-$C_4$)alkyl]$_2$, hydroxyl, halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

Preferably, $R^2$ is —$(CH_2)_p$-phenyl, —$CH(R^6)$-phenyl, —$C(R^6)_2$-phenyl, or —$NR^9$—$(CH_2)_p$-phenyl, wherein in each instance the phenyl radical is optionally substituted by up to four groups selected from halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

More preferably, $R^2$ is —$NR^9$—$CH_2$-phenyl, wherein the phenyl radical is optionally substituted by up to four groups selected from halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

In an alternative aspect, $R^2$ is more preferably —$CH(R^6)$-phenyl or —$C(R^6)_2$-phenyl, wherein each $R^6$ is fluorine or the two $R^6$ together form a cyclopropyl group with the carbon atom to which they are bound and wherein in each instance the phenyl radical is optionally substituted by up to four groups selected from halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

In a further aspect, $R^2$ is more preferably —$CH_2$-phenyl, wherein in each instance the phenyl radical is optionally substituted by up to four groups selected from halogen, cyano, ($C_1$-$C_4$)alkyl, fluoro($C_1$-$C_4$)alkyl, ($C_1$-$C_4$)alkoxy, fluoro($C_1$-$C_4$)alkoxy, said alkyl and alkoxy being optionally substituted by one or more hydroxyl.

Most preferably, $R^2$ is benzyl.

In one preferred embodiment, $R^5$ is ($C_1$-$C_6$)alkyl, fluoro($C_1$-$C_6$)alkyl, ($C_3$-$C_6$)cycloalkylmethylene, fluoro($C_3$-$C_6$)cycloalkylmethyl, said alkyl and cycloalkyl being optionally substituted by one or more hydroxyl, or —$(CH_2)_q$-$Het^2$;

In one preferred embodiment, $R^7$ and $R^8$ are each independently ($C_1$-$C_4$)alkyl, fluoro($C_1$-$C_4$)alkyl, ($C_3$-$C_6$)cycloalkyl or fluoro($C_3$-$C_6$)cycloalkyl.

Preferably, $R^{100}$ is H.

Particularly preferred compounds of the invention include those in which each variable in Formula (I) is selected from the suitable and/or preferred groups for each variable. Even more preferable compounds of the invention include those where each variable in Formula (I) is selected from the more preferred or most preferred groups for each variable.

Exemplary compounds of the invention include:
4-methoxy-2-(1-phenylethyl)-6,7,8,9-tetrahydro-5H-pyrimido[4,5-d]azepine;
2-(3-chlorobenzyl)-N-methyl-6,7,8,9-tetrahydro-5H-pyrimido[4,5,d]azepine-4-amine;
2-[difluoro(phenyl)methyl]-4-methoxy-6,7,8,9-tetrahydro-5H-pyrimido[4,5-d]azepine;
N,N-dimethyl-2-(1-methyl-1-phenylethyl)-6,7,8,9-tetrahydro-5H-pyrimido[4,5-d]azepin-4-amine;
2-(1-phenylcyclopropyl)-6,7,8,9-tetrahydro-5H-pyrimido[4,5-d]azepine;
N-methyl-2-(1-phenylcyclopropyl)-6,7,8,9-tetrahydro-5H-pyrimido[4,5-d]azepin-4-amine;
4-pyrrolidin-1-yl-2-(1-phenylcyclopropyl)-5,6,8,9-tetrahydro-7H-pyrimido[4,5-d]azepine;
N-benzyl-N-methyl-4-pyrrolidi-1-yl-6,7,8,9-tetrahydro-5H-pyrimido[4,5,d]azepin-2-amine;
2-benzyl-N-(cyclopropylmethyl)-N-methyl-6,7,8,9-tetrahydro-5H-pyrimido[4,5-d]azepin-4-amine;
2-benzyl-N-isopropyl-6,7,8,9-tetrahydro-5H-pyrimido[4,5-d]azepin-4-amine;
2-benzyl-4-[(3R)-3-methylmorpholin-4-yl]-6,7,8,9-tetrahydro-5H-pyrimido[4,5-d]azepine,
[1-(2-benzyl-6,7,8,9-tetrahydro-5H-pyrimido[4,5-d]azepin-4-yl)pyrrolidin-2-yl]methanol;
1-(2-benzyl-6,7,8,9-tetrahydro-5H-pyrimido[4,5-d]azepin-4-yl)piperidine-4-carbonitrile;
N-[2-(2-chlorophenyl)ethyl]-6,7,8,9-tetrahydro-5H-pyrimido[4,5-d]azepin-2-amine;
N-(2-phenylethyl)-6,7,8,9-tetrahydro-5H-pyrimido[4,5-d]azepin-2-amine;
2-benzyl-4-(2,2,2-trifluoro-ethoxy)-6,7,8,9-tetrahydro-5H-pyrimido[4,5-d]azepine;
2-(2-chlorobenzyl)-6,7,8,9-tetrahydro-5H-pyrimido[4,5-d]azepine;
2-[2-(trifluoromethyl)benzyl]-6,7,8,9-tetrahydro-5H-pyrimido[4,5-d]azepine;
2-(4-tert-butylbenzyl)-4-methoxy-6,7,8,9-tetrahydro-5H-pyrimido[4,5-d]azepine;
2-(4-ethylbenzyl)-4-methoxy-6,7,8,9-tetrahydro-5H-pyrimido[4,5-d]azepine;
2-(4-isopropylbenzyl)-4-methoxy-6,7,8,9-tetrahydro-5H-pyrimido[4,5-d]azepine;
4-methoxy-2-[4-(trifluoromethyl)benzyl]-6,7,8,9-tetrahydro-5H-pyrimido[4,5-d]azepine;
N-benzyl-6,7,8,9-tetrahydro-5H-pyrimido[4,5-d]azepin-2-amine;

2-[2-(2-methylphenyl)ethyl]-6,7,8,9-tetrahydro-5H-pyrimido[4,5-d]azepine;
2-(2-phenylethyl)-6,7,8,9-tetrahydro-5H-pyrimido[4,5-d]azepine;
2-[2-(4-chlorophenyl)ethyl]-4-methoxy-6,7,8,9-tetrahydro-5H-pyrimido[4,5-d]azepine;
2-[2-(2-chlorophenyl)ethyl]-4-methoxy-6,7,8,9-tetrahydro-5H-pyrimido[4,5-d]azepine;
and the pharmaceutically acceptable salts, solvates and prodrugs thereof.

Preferably the compound is selected from:
N-methyl-2-(1-phenylethyl)-6,7,8,9-tetrahydro-5H-pyrimido[4,5-d]azepin-4-amine;
2-(1-methyl-1-phenylethyl)-6,7,8,9-tetrahydro-5H-pyrimido[4,5-d]azepine;
2-(1-methyl-1-phenylethyl)-4-morpholin-4-yl-6,7,8,9-tetrahydro-5H-pyrimido[4,5-d]azepine;
N-benzyl-4-methoxy-N-methyl-6,7,8,9-tetrahydro-5H-pyrimido[4,5,d]azepin-2-amine;
1-(2-benzyl-6,7,8,9-tetrahydro-5H-pyrimido[4,5-d]azepin-4-yl)piperidin-3-ol;
2-benzyl-4-piperidin-1-yl-6,7,8,9-tetrahydro-5H-pyrimido[4,5-d]azepine;
2-benzyl-4-(3-methylpiperidin-1-yl)-6,7,8,9-tetrahydro-5H-pyrimido[4,5-d]azepine;
2-benzyl-N-(tetrahydrofuran-3-yl)-6,7,8,9-tetrahydro-5H-pyrimido[4,5-d]azepin-4-amine;
2-[2-(3-chlorophenyl)ethyl]-4-methoxy-6,7,8,9-tetrahydro-5H-pyrimido[4,5-d]azepine;
phenyl-(6,7,8,9-tetrahydro-5H-pyrimido[4,5-d]azepin-2-yl)-methanol;
2-benzyl-4-(1H-pyrazol-1-yl)-6,7,8,9-tetrahydro-5H-pyrimido[4,5-d]azepine;
2-(1-phenylethyl)-6,7,8,9-tetrahydro-5H-pyrimido[4,5-d]azepine;
2-[difluoro(phenyl)methyl]-N-methyl-6,7,8,9-tetrahydro-5H-pyrimido[4,5-d]azepin-4-amine;
2-[difluoro(phenyl)methyl]-4-methoxy-6,7,8,9-tetrahydro-5H-pyrimido[4,5-d]azepine;
4-morpholin-4-yl-2-(1-phenylcyclopropyl)-6,7,8,9-tetrahydro-5H-pyrimido[4,5-d]azepine;
N-benzyl-N-methyl-4-morpholin-4-yl-6,7,8,9-tetrahydro-5H-pyrimido[4,5,d]azepin-2-amine;
N-2-benzyl-N-2,N-4,N-4-trimethyl-6,7,8,9-tetrahydro-5H-pyrimido[4,5,d]azepin-2-amine;
2-benzyl-N-methyl-6,7,8,9-tetrahydro-5H-pyrimido[4,5-d]azepin-4-amine;
2-benzyl-N-(tetrahydrofuran-2-ylmethyl)-6,7,8,9-tetrahydro-5H-pyrimido[4,5-d]azepin-4-amine;
2-[(2-benzyl-6,7,8,9-tetrahydro-5H-pyrimido[4,5-d]azepin-4-yl)amino]ethanol;
(2S)-2-[(2-benzyl-6,7,8,9-tetrahydro-5H-pyrimido[4,5-d]azepin-4-yl)amino]-3-methylbutan-1-ol;
2-benzyl-4-[(3S)-3-methoxypyrrolidin-1-yl]-6,7,8,9-tetrahydro-5H-pyrimido[4,5-d]azepine;
2-benzyl-N-[2-(1H-pyrazol-1-yl)ethyl]-6,7,8,9-tetrahydro-5H-pyrimido[4,5-d]azepin-4-amine;
2-[(2-benzyl-6,7,8,9-tetrahydro-5H-pyrimido[4,5-d]azepin-4-yl)amino]propan-1-ol;
2-benzyl-4-morpholin-4-yl-6,7,8,9-tetrahydro-5H-pyrimido[4,5-d]azepine;
1-(2-benzyl-6,7,8,9-tetrahydro-5H-pyrimido[4,5-d]azepin-4-yl)piperidin-4-ol;
1-(2-benzyl-6,7,8,9-tetrahydro-5H-pyrimido[4,5-d]azepin-4-yl)piperidine-3-carbonitrile;
1-{[(2-benzyl-6,7,8,9-tetrahydro-5H-pyrimido[4,5-d]azepin-4-yl)amino]methyl}cyclobutanol;
[1-(2-benzyl-6,7,8,9-tetrahydro-5H-pyrimido[4,5-d]azepin-4-yl)pyrrolidin-3-yl]methanol;
2-benzyl-4-(3-fluoropyrrolidin-1-yl)-6,7,8,9-tetrahydro-5H-pyrimido[4,5-d]azepine;
1-(2-benzyl-6,7,8,9-tetrahydro-5H-pyrimido[4,5-d]azepin-4-yl)pyrrolidin-3-ol;
2-benzyl-4-[(3S)-3-methylmorpholin-4-yl]-6,7,8,9-tetrahydro-5H-pyrimido[4,5-d]azepine;
2-benzyl-N,N-dimethyl-6,7,8,9-tetrahydro-5H-pyrimido[4,5-d]azepin-4-amine;
2-benzyl-9-methyl-6,7,8,9-tetrahydro-5H-pyrimido[4,5-d]azepine;
2-benzyl-N,9-dimethyl-6,7,8,9-tetrahydro-5H-pyrimido[4,5-d]azepin-4-amine;
N-benzyl-N-methyl-6,7,8,9-tetrahydro-5H-pyrimido[4,5-d]azepin-2-amine;
N,N-dimethyl-6,7,8,9-tetrahydro-5H-pyrimido[4,5-d]azepin-2-amine;
2-benzyl-4-cyclopropyl-6,7,8,9-tetrahydro-5H-pyrimido[4,5-d]azepine;
2-benzyl-4-ethyl-6,7,8,9-tetrahydro-5H-pyrimido[4,5-d]azepine;
2-benzyl-6,7,8,9-tetrahydro-5H-pyrimido[4,5-d]azepine;
2-benzyl-4-imidazol-1-yl-6,7,8,9-tetrahydro-5H-pyrimido[4,5-d]azepine;
2-(3-chlorobenzyl)-6,7,8,9-tetrahydro-5H-pyrimido[4,5-d]azepine;
2-(4-chlorobenzyl)-6,7,8,9-tetrahydro-5H-pyrimido[4,5-d]azepine;
4-ethoxy-2-(1-phenylethyl)-6,7,8,9-tetrahydro-5H-pyrimido[4,5-d]azepine;
2-(2-fluorobenzyl)-6,7,8,9-tetrahydro-5H-pyrimido[4,5-d]azepine;
2-(3-fluorobenzyl)-6,7,8,9-tetrahydro-5H-pyrimido[4,5-d]azepine;
2-(4-fluorobenzyl)-6,7,8,9-tetrahydro-5H-pyrimido[4,5-d]azepine;
2-[3-(trifluoromethyl)benzyl]-6,7,8,9-tetrahydro-5H-pyrimido[4,5-d]azepine;
2-(4-methylbenzyl)-6,7,8,9-tetrahydro-5H-pyrimido[4,5-d]azepine;
2-(3-methylbenzyl)-6,7,8,9-tetrahydro-5H-pyrimido[4,5-d]azepine;
2-(2-methylbenzyl)-6,7,8,9-tetrahydro-5H-pyrimido[4,5-d]azepine;
2-benzyl-4-methoxy-6,7,8,9-tetrahydro-5H-pyrimido[4,5-d]azepine;
2-benzyl-4-methyl-6,7,8,9-tetrahydro-5H-pyrimido[4,5-d]azepine;
2-benzyl-4-butyl-6,7,8,9-tetrahydro-5H-pyrimido[4,5-d]azepine;
and the pharmaceutically acceptable salts, solvates and prodrugs thereof.

More preferably the compound is selected from:
2-benzyl-4-(1H-pyrazol-1-yl)-6,7,8,9-tetrahydro-5H-pyrimido[4,5-d]azepine;
2-(1-phenylethyl)-6,7,8,9-tetrahydro-5H-pyrimido[4,5-d]azepine;
2-[difluoro(phenyl)methyl]-N-methyl-6,7,8,9-tetrahydro-5H-pyrimido[4,5-d]azepin-4-amine;
2-[difluoro(phenyl)methyl]-4-methoxy-6,7,8,9-tetrahydro-5H-pyrimido[4,5-d]azepine;
4-morpholin-4-yl-2-(1-phenylcyclopropyl)-6,7,8,9-tetrahydro-5H-pyrimido[4,5-d]azepine;
N-benzyl-N-methyl-4-morpholin-4-yl-6,7,8,9-tetrahydro-5H-pyrimido[4,5,d]azepin-2-amine;

N-2-benzyl-N-2,N-4,N-4-trimethyl-6,7,8,9-tetrahydro-5H-pyrimido[4,5,d]azepin-2-amine;
2-benzyl-N-methyl-6,7,8,9-tetrahydro-5H-pyrimido[4,5-d]azepin-4-amine;
2-benzyl-N-(tetrahydrofuran-2-ylmethyl)-6,7,8,9-tetrahydro-5H-pyrimido[4,5-d]azepin-4-amine;
2-[(2-benzyl-6,7,8,9-tetrahydro-5H-pyrimido[4,5-d]azepin-4-yl)amino]ethanol;
(2S)-2-[(2-benzyl-6,7,8,9-tetrahydro-5H-pyrimido[4,5-d]azepin-4-yl)amino]-3-methylbutan-1-ol;
2-benzyl-4-[(3S)-3-methoxypyrrolidin-1-yl]-6,7,8,9-tetrahydro-5H-pyrimido[4,5-d]azepine;
2-benzyl- N-[2-(1H-pyrazol-1-yl)ethyl]-6,7,8,9-tetrahydro-5H-pyrimido[4,5-d]azepin-4-amine;
2-[(2-benzyl-6,7,8,9-tetrahydro-5H-pyrimido[4,5-d]azepin-4-yl)amino]propan-1-ol;
2-benzyl-4-morpholin-4-yl-6,7,8,9-tetrahydro-5H-pyrimido[4,5-d]azepine;
1-(2-benzyl-6,7,8,9-tetrahydro-5H-pyrimido[4,5-d]azepin-4-yl)piperidin-4-ol;
1-(2-benzyl-6,7,8,9-tetrahydro-5H-pyrimido[4,5-d]azepin-4-yl)piperidine-3-carbonitrile;
1-{[(2-benzyl-6,7,8,9-tetrahydro-5H-pyrimido[4,5-d]azepin-4-yl)amino]methyl}cyclobutanol;
[1-(2-benzyl-6,7,8,9-tetrahydro-5H-pyrimido[4,5-d]azepin-4-yl)pyrrolidin-3-yl]methanol;
2-benzyl-4-(3-fluoropyrrolidin-1-yl)-6,7,8,9-tetrahydro-5H-pyrimido[4,5-d]azepine;
1-(2-benzyl-6,7,8,9-tetrahydro-5H-pyrimido[4,5-d]azepin-4-yl)pyrrolidin-3-ol;
2-benzyl-4-[(3S)-3-methylmorpholin-4-yl]-6,7,8,9-tetrahydro-5H-pyrimido[4,5-d]azepine;
2-benzyl-N,N-dimethyl-6,7,8,9-tetrahydro-5H-pyrimido[4,5-d]azepin-4-amine;
2-benzyl-9-methyl-6,7,8,9-tetrahydro-5H-pyrimido[4,5-d]azepine;
2-benzyl-N,9-dimethyl-6,7,8,9-tetrahydro-5H-pyrimido[4,5-d]azepin-4-amine;
N-benzyl-N-methyl-6,7,8,9-tetrahydro-5H-pyrimido[4,5-d]azepin-2-amine;
N,N-dimethyl-6,7,8,9-tetrahydro-5H-pyrimido[4,5-d]azepin-2-amine;
2-benzyl-4-cyclopropyl-6,7,8,9-tetrahydro-5H-pyrimido[4,5-d]azepine;
2-benzyl-4-ethyl-6,7,8,9-tetrahydro-5H-pyrimido[4,5-d]azepine;
2-benzyl-6,7,8,9-tetrahydro-5H-pyrimido[4,5-d]azepine;
2-benzyl-4-imidazol-1-yl-6,7,8,9-tetrahydro-5H-pyrimido[4,5-d]azepine;
2-(3-chlorobenzyl)-6,7,8,9-tetrahydro-5H-pyrimido[4,5-d]azepine;
2-(4-chlorobenzyl)-6,7,8,9-tetrahydro-5H-pyrimido[4,5-d]azepine;
4-ethoxy-2-(1-phenylethyl)-6,7,8,9-tetrahydro-5H-pyrimido[4,5-d]azepine;
2-(2-fluorobenzyl)-6,7,8,9-tetrahydro-5H-pyrimido[4,5-d]azepine;
2-(3-fluorobenzyl)-6,7,8,9-tetrahydro-5H-pyrimido[4,5-d]azepine;
2-(4-fluorobenzyl)-6,7,8,9-tetrahydro-5H-pyrimido[4,5-d]azepine;
2-[3-(trifluoromethyl)benzyl]-6,7,8,9-tetrahydro-5H-pyrimido[4,5-d]azepine;
2-(4-methylbenzyl)-6,7,8,9-tetrahydro-5H-pyrimido[4,5-d]azepine;
2-(3-methylbenzyl)-6,7,8,9-tetrahydro-5H-pyrimido[4,5-d]azepine;
2-(2-methylbenzyl)-6,7,8,9-tetrahydro-5H-pyrimido[4,5-d]azepine;
2-benzyl-4-methoxy-6,7,8,9-tetrahydro-5H-pyrimido[4,5-d]azepine;
2-benzyl-4-methyl-6,7,8,9-tetrahydro-5H-pyrimido[4,5-d]azepine;
2-benzyl-4-butyl-6,7,8,9-tetrahydro-5H-pyrimido[4,5-d]azepine;
and the pharmaceutically acceptable salts, solvates and prodrugs thereof.

Most preferably the compound is selected from:
2-benzyl-N,9-dimethyl-6,7,8,9-tetrahydro-5H-pyrimido[4,5-d]azepin-4-amine;
2-benzyl-4-(1H-pyrazol-1-yl)-6,7,8,9-tetrahydro-5H-pyrimido[4,5-d]azepine;
2-(1-phenylethyl)-6,7,8,9-tetrahydro-5H-pyrimido[4,5-d]azepine;
2-(4-methylbenzyl)-6,7,8,9-tetrahydro-5H-pyrimido[4,5-d]azepine;
2-benzyl-6,7,8,9-tetrahydro-5H-pyrimido[4,5-d]azepine;
2-benzyl-4-imidazol-1-yl-6,7,8,9-tetrahydro-5H-pyrimido[4,5-d]azepine;
4-ethoxy-2-(1-phenylethyl)-6,7,8,9-tetrahydro-5H-pyrimido[4,5-d]azepine;
2-(3-fluorobenzyl)-6,7,8,9-tetrahydro-5H-pyrimido[4,5-d]azepine;
2-benzyl-N-methyl-6,7,8,9-tetrahydro-5H-pyrimido[4,5-d]azepin-4-amine;
(2S)-2-[(2-benzyl-6,7,8,9-tetrahydro-5H-pyrimido[4,5-d]azepin-4-yl)amino]-3-methylbutan-1-ol;
2-benzyl-N-[2-(1H-pyrazol-1-yl)ethyl]-6,7,8,9-tetrahydro-5H-pyrimido[4,5-d]azepin-4-amine;
2-benzyl-4-morpholin-4-yl-6,7,8,9-tetrahydro-5H-pyrimido[4,5-d]azepine;
1-{[(2-benzyl-6,7,8,9-tetrahydro-5H-pyrimido[4,5-d]azepin-4-yl)amino]methyl}cyclobutanol;
[1-(2-benzyl-6,7,8,9-tetrahydro-5H-pyrimido[4,5-d]azepin-4-yl)pyrrolidin-3-yl]methanol;
2-benzyl-4-[(3S)-3-methylmorpholin-4-yl]-6,7,8,9-tetrahydro-5H-pyrimido[4,5-d]azepine;
2-benzyl-N,N-dimethyl-6,7,8,9-tetrahydro-5H-pyrimido[4,5-d]azepin-4-amine;
2-[difluoro(phenyl)methyl]-N-methyl-6,7,8,9-tetrahydro-5H-pyrimido[4,5-d]azepin-4-amine;
2-[difluoro(phenyl)methyl]-4-methoxy-6,7,8,9-tetrahydro-5H-pyrimido[4,5-d]azepine;
and the pharmaceutically acceptable salts, solvates and prodrugs thereof.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002), incorporated herein by reference.

Pharmaceutically acceptable salts of compounds of formula I may be prepared by one or more of three methods:
(i) by reacting the compound of formula I with the desired acid or base;
(ii) by removing an acid-or base-labile protecting group from a suitable precursor of the compound of formula I or by ring-opening a suitable cyclic precursor, for example, a lactone or lactam, using the desired acid or base; or
(iii) by converting one salt of the compound of formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change; typically first order ('melting point').

The compounds of formula (I) may also exist in unsolvated and solvated forms. The term 'solvate' is used herein to describe a molecular complex comprising a compound of formula (I) and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of formula (1) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $-COO^-Na^+$, $-COO^{31} K^+$, or $-SO_3^-Na^+$) or non-ionic (such as $-N^-N^+(CH_3)_3$) polar head group. For more information, see *Crystals and the Polarizing Microscope* by N. H. Hartshorne and A. Stuart, $4^{th}$ Edition (Edward Arnold, 1970), incorporated herein by reference.

Hereinafter all references to compounds of formula (I) include references to salts, solvates, multi-component complexes and liquid crystals thereof and to solvates, multi-component complexes and liquid crystals of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association), incorporated herein by reference.

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985) and Fleischer et al, *Advanced Drug Delivery Reviews*, 19(1996), 115-130, incorporated herein by reference.

Some examples of prodrugs in accordance with the invention include
(i) where the compound of formula I contains an alcohol functionality (—OH), an ether thereof, for example, a compound wherein the hydrogen of the alcohol functionality of the compound of formula I is replaced by $(C_1-C_6)$alkanoyloxymethyl; and (ii) where the compound of formula I contains a primary or secondary amino functionality (—$NH_2$ or —NHR where R≠H), an amide thereof, for example, a compound wherein, as the case may be, one or both hydrogens of the amino functionality of the compound of formula I is/are replaced by $(C_1-C_{10})$alkanoyl or $CO_2$ $(C_1-C_{10})$alkyl.

Further examples of replacement groups in accordance with the foregoing examples and examples of other prodrug types may be found in the aforementioned references.

Moreover, certain compounds of formula (I) may themselves act as prodrugs of other compounds of formula (I).

The compounds of formula (I) may have asymmetric carbon atoms. The bonds from an asymmetric carbon in compounds of the present invention may be depicted herein using a solid line (—), a solid wedge ( ▬▬ ),or a dotted wedge ( ⋯⋯ ).The use of a solid line to depict bonds from asymmetric carbon atoms is meant to indicate that all possible stereoisomers at that carbon atom are included. The use of either a solid or dotted wedge to depict bonds from asymmetric carbon atoms is meant to indicate that only the stereoisomer shown is meant to be included. It is possible that compounds of formula (I) may contain more than one asymmetric carbon atom. In those compounds, the use of a solid line to depict bonds from asymmetric carbon atoms is meant to indicate that all possible stereoisomers are meant to be included. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula I contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2 to 20%, and may contain from 0 to 5% by volume of an alkylamine. Concentration of the eluate affords the enriched mixture. The absolute composition of the mobile phase will be dependent upon the chiral stationary phase (asymmetric resin) selected.

Stereoisomeric conglomerates may be separated by conventional techniques known to those skilled in the art—see, for example, *Stereochemistry of Organic Compounds* by E. L. Eliel and S. H. Wilen (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula I, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. A variety of disorders (including diseases and/or conditions) have been shown to be modulated by 5-HT$_{2c}$ receptor Uganda. See, e.g., Bishop, Michael J., and Bjorn M. Nilsson, "New 5-HT2c receptor agonist" *Expert Opin, Ther Patents,* 13(11), 1591-1705 (2003). Of particular interest are those disorders including sexual dysfunction, lower urinary tract symptoms, eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), premenstrual syndrome or late luteal phase syndrome, migraine, panic disorder, anxiety, post-traumatic syndrome, dementia (including memory loss, Alzheimer's disease, dementia of aging, vascular dementia, mild cognitive impairment, age-related cognitive decline, and mild neurocognitive disorder), seizure disorders, epilepsy, gastrointestinal disorders (e.g., dysfunction of gastrointestinal motility or intestinal propulsion), attention deficit disorders or attention hyperactivity disorders (ADD/ADHD), disruptive behavior disorders, impulse control disorders, borderline personality disorder, obsessive compulsive disorder, chronic fatigue syndrome, anorexia nervosa, disorders of sleep (e.g., sleep apnea), autism, epilepsy, mutism, spinal cord injury, damage of the central nervous system (e.g., trauma, stroke, neurodegenerative diseases or toxic or infective CNS diseases (e.g., encephalitis or meningitis)), cardiovascular disorders (e.g., thrombosis), Parkinson's disease, diabetes insipidus, and type II diabetes.

The invention relates to compounds of formula (I), and their pharmaceutically acceptable salts, solvates and pro-drugs, which may be used in the prophylaxis and/or treatment of sexual dysfunction.

Sexual dysfunction (SD) is a significant clinical problem which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman el at *J. Urology*, 1999, 161, 5-11).

FSD can be defined as the difficulty or inability of a woman to find satisfaction in sexual expression. FSD is a collective term for several diverse female sexual disorders (Leiblum, S. R. (1998). Definition and classification of female sexual disorders. *Int. J. Impotence Res.*, 10, S104-S106; Berman, J. R., Berman, L. & Goldstein, I. (1999). Female sexual dysfunction: Incidence, pathophysiology, evaluations and treatment options. *Urology*, 54, 385-391). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998). Definition and classification of female sexual disorders, *Int. J. Impotence Res.*, 10, S104-S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants (e.g. SSRIs) or antihypertensive agents.

Sexual pain disorders (e.g. dyspareunia and vaginismus) is characterised by pain resulting from penetration and may be caused by medications which reduce lubrication, endometriosis, pelvic inflammatory disease, inflammatory bowel disease or urinary tract problems.

The prevalence of FSD is difficult to gauge because the term covers several types of problem, some of which are difficult to measure, and because the interest in treating FSD is relatively recent. Many women's sexual problems are associated either directly with the female ageing process or with chronic illnesses such as diabetes and hypertension.

Because FSD consists of several subtypes that express symptoms in separate phases of the sexual response cycle, there is not a single therapy. Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (eg FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects.

Since interest is relatively recent in treating FSD pharmacologically, therapy consists of the following: psychological counselling, over-the-counter sexual lubricants, and investigational candidates, including drugs approved for other conditions. These medications consist of hormonal agents, either testosterone or combinations of oestrogen and testosterone and more recently vascular drugs that have proved effective in male erectile dysfunction. None of these agents has been demonstrated to be very effective in treating FSD.

The Diagnostic and Statistical Manual (DSM) IV of the American Psychiatric Association defines Female Sexual Arousal Disorder (FSAD) as being: "a persistent or recurrent inability to attain or to maintain until completion of the sexual activity adequate lubrication-swelling response of sexual excitement. The disturbance must cause marked distress or interpersonal difficulty."

The arousal response consists of vasocongestion in the pelvis, vaginal lubrication and expansion and swelling of the external genitalia. The disturbance causes marked distress and/or interpersonal difficulty. FSAD is a highly prevalent sexual disorder affecting pre-, peri- and post menopausal (±HRT) women. It is associated with concomitant disorders such as depression, cardiovascular diseases, diabetes and UG disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

It has recently been hypothesised that there is a vascular basis for at least a proportion of patients with symptoms of FSAD (Goldstein et al., Int. J. Impot. Res., 10, S84-S90, 1998) with animal data supporting this view (Park et al., Int. J. Impot. Res., 9, 27-37, 1997). Drug candidates for treating FSAD, which have been under investigation for efficacy, are primarily erectile dysfunction therapies that promote circulation to the male genitalia. They consist of two types of formulation, oral or sublingual medications (Apomorphine, Phentolamine, phosphodiesterase type 5 (PDE5) inhibitors e.g. Sildenafil), and prostaglandin ($PGE_1$) that are injected or administered transurethrally in men, and topically to the genitalia in women.

The compounds of formula (I) are advantageous by providing a means for restoring a normal sexual arousal response—namely increased genital blood flow leading to vaginal, clitoral and labial engorgement. This will result in increased vaginal lubrication via plasma transudation, increased vaginal compliance and increased genital sensitivity. Hence, the compounds of the invention provide means to restore, or potentiate, the normal sexual arousal response.

The compounds of formula (I) find application in the following sub-populations of patients with FSD: the young, the elderly, pre-menopausal, peri-menopausal, post-menopausal women with or without hormone replacement therapy.

The compounds of formula (I) find application in patients with FSD arising from:
 i) Vascylogenic etiologies eg cardiovascular or atherosclerotic diseases, hypercholesterolemia, cigarette smoking, diabetes, hypertension, radiation and perineal trauma, traumatic injury to the iliohypogastric pudendal vacular system.
 ii) Neurogenic etiologies such as spinal cord injuries or diseases of the central nervous system including multiple sclerosis, diabetes, Parkinsonism, cerebrovascular accidents, peripheral neuropathies, trauma or radical pelvic surgery.
 iii) Hormonal/endocrine etiologies such as dysfunction of the hypothalamic/pituitary/gonadal axis, or dysfunction of the ovaries, dysfunction of the pancreas, surgical or medical castration, androgen deficiency, high circulating levels of prolactin eg hyperprolactinemia, natural menopause, premature ovarian failure, hyper and hypothyroidism.
 iv) Psychogenic etiologies such as depression, obsessive compulsive disorder, anxiety disorder, postnatal depression/"Baby Blues", emotional and relational issues, performance anxiety, marital discord, dysfunctional attitudes, sexual phobias, religious inhibition or a traumatic past experiences.
 v) Drug-induced sexual dysfunction resulting from therapy with selective serotonin reuptake inhibitors (SSRis) and other antidepressant therapies (tricyclics and major tranquillizers), anti-hypertensive therapies, sympatholytic drugs, chronic oral contraceptive pill therapy.

Male sexual dysfunction (MSD) is generally associated with either erectile dysfunction, also known as male erectile dysfunction (MED) and/or ejaculatory disorders such as premature ejaculation, anorgasmia (unable to achieve orgasm) or desire disorders such as hypoactive sexual desire disorder (lack of interest in sex), Patients with mild to moderate MED should benefit from treatment with a compound of formula (I) and patients with severe MED may also respond. However, early investigations suggest that the responder rate of patients with mild, moderate and severe MED will be greater in combination with a PDE5 inhibitor. Mild, moderate and severe MED will be terms known to the man skilled in the art, but guidance can be found in *The Journal of Urology*, vol 151, 54-61 (Jan 1994).

The compounds of formula (I) find application in the following sub-populations of patients with MED: psychogenic, endocrinologic, neurogenic, arteriogenic, drug-induced sexual dysfunction (lactogenic) and sexual dysfunction related to cavernosal factors, particularly venogenic causes. These patient groups are described in more detail in Clinical Andrology vol 23, no. 4, p 773-782, and chapter 3 of the book by I. Eardley and K. Sethia "Erectile Dysfunction—Current Investigation and Management, published by Mosby-Wolfe.

The compounds of formula (I) and their pharmaceutically acceptable salts, solvates and prodrugs, may also be useful in the treatment of benign prostatic hyperplasia (BPH), overactive bladder (OAB) and lower urinary tract symptoms (LUTS).

LUTS comprise three groups of urinary symptoms, which may be defined as storage (irritative), voiding (obstructive) and post-micturition symptoms. Storage symptoms comprise urgency, frequency, nocturia, urgency incontinence and stress incontinence, which can be associated with OAB and BPH. Voiding symptoms comprise hesitancy, poor flow, intermittency, straining and dysuria. Post-micturition symptoms comprise terminal dribbling, post-void dribbling and a sense of incomplete emptying.

Over Active Bladder (OAB) is defined as urgency, with or without urge incontinence, usually with frequency and nocturia [Abrams et al, Neurourology and Urodynamics 21:167-178 (2002)]. Prevalence of OAB in men and women is similar, with approximately 16% of the population of the USA suffering from the condition [Stewart et al, Prevalence of Overactive Bladder in the United States: Results from the NOBLE Program; Abstract Presented at the $2^{nd}$ International Consultation on Incontinence, July 2001, Paris, France].

The terms OAB Wet and OAB Dry describe OAB patients with or without urinary incontinence respectively. Until recently, the cardinal symptom of OAB was believed to be urinary incontinence. However, with the advent of the new terms this is clearly not meaningful for the large number of sufferers who are not incontinent (i.e. OAB Dry patients). Thus, a recent study from Liberman et al ['Health Related Quality of Life Among Adults with Symptoms of Overactive Bladder: Results From A US Community-Based Survey'; Urology 57(6), 1044-1050, 2001] examined the impact of all OAB symptoms on the quality of life of a community-based sample of the US population. This study demonstrated that individuals suffering from OAB without any demonstrable loss of urine have an impaired quality of life when compared with controls.

BPH is a chronically progressive disease that can lead to complications such as acute urinary retention, recurrent urinary tract infections, bladder stones and renal dysfunction. The prevalence and average severity of LUTS associated with BPH in men increases with age. BPH leads to an increase in prostate volume, creating urethral and bladder outflow obstruction as well as secondary changes in bladder function. The effects of this are manifested by both storage (irritative) and voiding (obstructive) symptoms.

The compounds of formula (I) and their pharmaceutically acceptable salts, solvates and prodrugs, may also be useful in the treatment of psychotic disorders and conditions such as schizophrenia, delusional disorders and drug induced psychosis; anxiety disorders such as panic and obsessive-compulsive disorder; and movement disorders including Parkinson's disease and Huntington's disease.

Examples of psychotic disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type.

In use to treat psychotic disorders of the schizophrenic types, the compounds of formula (I) would be useful for removing or ameliorating such symptoms as anxiety, agitation, excessive aggression, tension, and social or emotional withdrawal in psychotic patients. In addition, the compounds of formula (I) may be useful in the blocking of serotonin-induced contractions of bronchial tissues and of blood vessels, arteries as well as veins. The compounds of formula (I) may also be useful as sedating-, anxiolytic-, anti-aggressive-, anti-stress-, muscular protectant-, and cardiovascular protectant agents and, consequently, they would be useful to protect warm-blooded animals, for example, in stress situations, e.g., during transport periods and the like situations.

Examples of movement disorders that can be treated according to the present invention include, but are not limited to, Huntington's disease and dyskinesia associated with dopamine agonist therapy, Parkinson's disease, restless leg syndrome, and essential tremor.

Other disorders that can be treated according to the present invention are obsessive/compulsive disorders, Tourette's syndrome and other tic disorders.

The compounds of formula (I) and their pharmaceutically acceptable salts, solvates and prodrugs, may also be useful in the treatment of an anxiety disorder or condition. Examples of anxiety disorders that can be treated according to the present invention include, but are not limited to, panic disorder, agoraphobia, a specific phobia, social phobia, obsessive-compulsive disorder, post-traumatic stress disorder, acute stress disorder and generalized anxiety disorder.

The compounds of formula (I) and their pharmaceutically acceptable salts, solvates and prodrugs, may also be useful in the treatment of a drug addiction, for example an alcohol, amphetamine, cocaine, or opiate addiction. A "drug addiction", as used herein, means an abnormal desire for a drug and is generally characterized by motivational disturbances such a compulsion to take the desired drug and episodes of intense drug craving.

The compounds of formula (I) and their pharmaceutically acceptable salts, solvates and prodrugs, may also be useful in the treatment of a disorder or condition comprising as a symptom a deficiency in attention and/or cognition. The phrase "deficiency in attention and/or cognition" as used herein in refers to a subnormal functioning in one or more cognitive aspects such as memory, intellect, or learning and logic ability, in a particular individual relative to other individuals within the same general age population. "Deficiency in attention and/or cognition" also refers to a reduction in any particular individual's functioning in one or more cognitive aspects, for example as occurs in age-related cognitive decline.

Examples of disorders that comprise as a symptom a deficiency in attention and/or cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; age-related cognitive decline; cognitive deficits associated with psychoses, and cognitive deficits associated with schizophrenia.

The compounds of formula (I) and their pharmaceutically acceptable salts, solvates and prodrugs, may also be useful in the treatment of a mood disorder or mood episode. Examples of mood disorders and mood episodes that can be treated according to the present invention include, but are not limited to, major depressive episode of the mild, moderate or severe type, a manic or mixed mood episode, a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder.

The compounds of formula (I) and their pharmaceutically acceptable salts, solvates and prodrugs, may also be useful in the treatment of a neurodegenerative disorder or condition. As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temporal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy. In one aspect of the present invention, the neurodegenerative disorder or condition comprises, neurodegeneration of striatal medium spiny neurons in a mammal, including a human. In a further aspect of the present invention, the neurodegenerative disorder or condition is Huntington's disease.

The compounds of formula (I) and their pharmaceutically acceptable salts, solvates and prodrugs, may also be useful in the treatment of an anxiety disorder or condition. Examples of anxiety disorders that can be treated according to the present invention include, but are not limited to, panic disorder; agoraphobia; a specific phobia; social phobia; obsessive-compulsive disorder; post-traumatic stress disorder; acute stress disorder; and generalized anxiety disorder.

Thus, according to a further aspect of the present invention, there is provided a compound of formula (I), or a pharmaceutically acceptable salt, solvate or prodrug thereof, for use as a medicament.

In yet a further aspect of the invention, there is provided a pharmaceutical composition including a compound of formula (I) or a pharmaceutically acceptable salt, solvate or prodrug thereof, together with a pharmaceutically or veterinarily acceptable excipient. In one aspect, the composition comprises a therapeutically effective amount of a compound of formula (I). In another aspect, the composition may also comprise one or more additional pharmaceutical agents (e.g., those described hereinbelow).

As a further aspect of the invention, there is provided the use of a compound of formula (I), or a pharmaceutically acceptable salt, solvate or prodrug thereof, for the manufacture of a medicament to treat a 5-$HT_{2c}$ receptor-mediated disorder, condition or disease.

As a yet further aspect of the invention, there is provided the use of a compound of formula (I), or of a pharmaceutically acceptable salt, solvate or prodrug thereof, for the manufacture of a medicament for the treatment of the above mentioned diseases, conditions or disorders, in particular, for the treatment of hypoactive sexual desire disorder, sexual arousal disorder, orgasmic disorder or sexual pain disorder, more particularly, for the treatment of sexual arousal disorder, orgasmic disorder or sexual pain disorder, and, most particularly, for the treatment of sexual arousal disorder.

As an alternative aspect, there is provided a compound of formula (I), or a pharmaceutically acceptable salt, solvate or prodrug thereof, for the treatment of a 5-$HT_{2c}$ receptor-mediated disorder, condition or disease.

In a further aspect, the invention provides a compound of formula (I), or a pharmaceutically acceptable salt, solvate or prodrug thereof, for the treatment of the above mentioned diseases, conditions or disorders, in particular, for the treatment of hypoactive sexual desire disorder, sexual arousal disorder, orgasmic disorder or sexual pain disorder, more particularly, for the treatment of sexual arousal disorder, orgasmic disorder or sexual pain disorder, and, most particularly, for the treatment of sexual arousal disorder.

In another aspect of the present invention, there is provided a method of treating a 5-$HT_{2c}$ receptor-mediated disease, condition, or disorder, which comprises administering to a subject in need of such treatment a therapeutically effective amount of a compound of formula (I) or a pharmaceutically acceptable salt, solvate, prodrug or composition thereof. The method is particularly useful for treating 5-$HT_{2c}$ receptor-mediated disorders.

In a further aspect, the invention provides a method of treating the above mentioned diseases, conditions or disorders, in particular, for the treatment of hypoactive sexual desire disorder, sexual arousal disorder, orgasmic disorder or sexual pain disorder, more particularly, for the treatment of sexual arousal disorder, orgasmic disorder or sexual pain disorder, and, most particularly, for the treatment of sexual arousal disorder, which comprises administering to a subject in need of such treatment a therapeutically effective amount of a compound of formula (I) or a pharmaceutically acceptable salt, solvate, prodrug or composition thereof. The method may further comprise the administration of one or more additional pharmaceutical agents (e.g., those described hereinbelow) for treating the above mentioned diseases.

In the present specification and appended claims, the term "subject" refers to mammals, especially humans (female or male), companion animals (e.g., dogs, cats and horses), edible animals, zoo animals, marine animals, birds and other similar animal species. "Edible animals" refers to food-source animals such as cows, pigs, sheep and poultry.

The expression "therapeutically effective amount" means an amount of a compound of formula (I) that (I) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The compounds of formula (I) and their pharmaceutically acceptable salts, solvates or prodrugs may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of formula (I) may be administered alone or in combination with one or more other compounds of formula (I) or in combination with one or more other drugs (or as any combination thereof). Generally, they will be administered as a formulation in association with one or more pharmaceutically acceptable excipients. The term 'excipient' is used herein to describe any ingredient other than the compound(s) of formula (I). The choice of excipient will to a large extent depend on factors such as the particular mode of administration, the effect of the excipient on solubility and stability, and the nature of the dosage, form.

Pharmaceutical compositions suitable for the delivery of compounds of formula (I) and methods for their preparation will be readily apparent to those skilled in the art. Such compositions and methods for their preparation may be found, for example, in *Remington's Pharmaceutical Sciences*, 19th Edition (Mack Publishing Company, 1995), incorporated herein by reference.

Oral Administration

The compounds of formula (I) may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of formula (I) may also be used in fast-dissolving, fast-disintegrating dosage forms such as those described in Expert Opinion in Therapeutic Patents, 11 (6), 981-986, by Liang and Chen (2001), incorporated herein by reference.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in *Pharmaceutical Dosage Forms: Tablets*, Vol. 1, by H. Lieberman and L. Lachman (Marcel Dekker, New York, 1980), incorporated herein by reference.

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864, incorporated herein by reference. Details of other suitable release technologies such as high energy dispersions and osmotic and coated particles are to be found in *Pharmaceutical Technology On-line*, 25(2), 1-14, by Verma et al (2001), incorporated herein by reference. The use of chewing gum to achieve controlled release is described in WO 00/35298, incorporated herein by reference.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. The compounds of formula (I) may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

Topical Administration

The compounds of formula (I) may also be administered topically, (intra)dermally, or transdermally, to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999), incorporated herein by reference.

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained, pulsed-, controlled-, targeted and programmed release.

Inhaled/Intranasal Administration

The compounds of formula (I) may also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebuliser contains a solution or suspension of the compound(s) of formula (I) comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of formula (I), a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of formula (I) per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release. In the case of dry powder inhalers and aerosols, the dosage unit is determined by means of a valve which delivers a metered amount. Units in accordance with the invention are typically arranged to administer a metered dose or "puff" containing from 1 µg to 10 mg of the compound of formula (I). The overall daily dose will typically be in the range 1 µg to 200 mg which may be administered in a single dose or, more usually, as divided doses throughout the day.

Rectal/Intravaginal Administration

The compounds of formula (I) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular/Aural Administration

The compounds of formula (I) may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

The compounds of formula (I) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148, incorporated herein by reference.

Kit-of-Parts

Inasmuch as it may desirable to administer a compound of formula (I) in combination with another therapeutic agent, for example, for the purpose of treating a particular disease or condition, it is within the scope of the present invention that two or more pharmaceutical compositions, at feast one of which contains a compound of formula (I), may conveniently be combined in the form of a kit suitable for coadministration of the compositions.

Thus the kit of the invention comprises two or more separate pharmaceutical compositions, at least one of which contains a compound of formula (I) or a pharmaceutically acceptable salt, solvate or prodrug or derivative thereof, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

The compounds of the present invention can be administered to a patient at dosage levels in the range of from about 0.1 mg to about 1,000 mg per day (preferably, about 1 mg to about 500 mg per day, more preferably, about 25 mg to about 250 mg per day, most preferably about 5 mg to about 100 mg per day). For a normal adult human having a body weight of about 70 kg, a dosage in the range of from about 0.01 mg to about 20 mg per kilogram body weight is typically sufficient, depending, of course, on the mode of administration, the age, condition and weight of the patient, and will in any case be at the ultimate discretion of the physician. The total daily dose may be administered in single or divided doses.

Combination Therapy

The compounds of formula (I) and their pharmaceutically acceptable salts, solvates or prodrugs may be administered alone or as part of a combination therapy. Thus included within the scope of the present invention are aspects comprising co-administration of, and compositions which contain, in addition to a compound of formula (I), one or more additional pharmaceutical agents. The pharmaceutical compositions may be administered simultaneously or sequentially and in any order. Suitable pharmaceutical agents that may be used in combination with the compounds of formula (I) for treating FSD include:

a) a PDE5 inhibitor, in particular 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); (6R,12aR)-2,3,6,7,12,12a-hexahydro-2-methyl-6-(3,4-methylenedioxyphenyl)-pyrazino[2',1':6,1]pyrido[3,4-b]indole-1,4-dione (tadalafil); 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); N-[[3-(4,7-dihydro-1-methyl-7-oxo-3-propyl-1H-pyrazolo[4,3-d]-pyrimidin-5-yl)-4-propxyphenyl]sulfonyl}-1-methyl2-pyrrolidinepropanamide (udenafil); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one; and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof;

b) a neutral endopeptidase (NEP) inhibitor, in particular wherein said NEP is EC 3.4.24.11, preferably wherein said NEP inhibitor is a selective inhibitor for EC 3.4.24.11; suitable NEP inhibitor compounds are described e.g. in WO 02/02513, EP1097719, WO 02/079143, EP1258474, WO2004/080985, in particular (2S)-2-{[1-({[3-(4-Chlorophenyl)propyl]amino}carbonyl)cyclopentyl]methyl}-4-methoxybutanoic acid and (R)-2-Methyl-3-(1-{[3-(2-methyl-1,3-benzothiazol-6-yl)propyl]carbamoyl}cyclopentyl) propanoic acid;

c) an NPY (neuropeptide Y) inhibitor (preferably an NPY-1 and/or. NPY-5 inhibitor);

d) a dopamine agonist (in particular a selective D2, selective D3, selective D4 and selective D2-like agent) such as Pramipexole (Pharmacia Upjohn compound number PNU95666), ropinirole, apomorphine, surmanirole, quinelorane, PNU-142774, bromocriptine, carbergoline, Lisuride;

e) a melanocortin receptor agonist (e.g., melanotan II, PT-14, PT-141) or a selective MC3 and MC4 agonists (e.g. THIQ);

f) an estrogen receptor modulator, estrogen agonists and/or estrogen antagonists, preferably raloxifene, tibolone or lasofoxifene;

g) an androgen such as androsterone, dehydro-androsterone, testosterone, androstanedione and a synthetic androgen;

h) an oestrogen, such as oestradiol, oestrone, oestriol and a synthetic estrogen, such as oestrogen benzoate;

i) a 5-HT1 a agonist, e.g. flibanserin.

Suitable pharmaceutical agents that may be used in combination with the compounds of formula (I) for treating MED include:

a) a PDE5 inhibitor;

b) an NPY (neuropeptide Y) inhibitor (preferably an NPY-1 and/or NPY-5 inhibitor);

c) a dopamine agonist (in particular a selective D2, selective D3, selective D4 and selective D2-like agent) such as Pramipexole (Pharmacia Upjohn compound number PNU95666), ropinirole, apomorphine, surmanirole, quinelorane, PNU-142774, bromocriptine, carbergoline, Lisuride;

d) a melanocortin receptor agonist (e.g., melanotan II, PT-14, PT-141) or a selective MC3 and MC4 agonists (e.g. THIQ);

e) an α-adrenergic receptor antagonist (also known as α-adrenoceptor blocker, α-receptor blocker or a-blocker); suitable $\alpha_1$-adrenergic receptor antagonists include: phentolamine, prazosin, phentolamine mesylate, trazodone, alfuzosin, indoramin, naftopidil, tamsulosin, phenoxybenzamine, rauwolfa alkaloids, Recordati 15/2739, SNAP 1069, SNAP 5089, RS17053, SL 89.0591, doxazosin, Example 19 of WO9830560, terazosin and abanoquil; suitable $\alpha_2$-adrenergic receptor antagonists include dibenarnine, tolazoline, trimazosin, efaroxan, yohimbine, idazoxan clonidine and dibenarnine; suitable non-selective α-adrenergic receptor antagonists include dapiprazole; further α-adrenergic receptor antagonists are described in PCT application WO99/30697 published on 14 Jun. 1998 and U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference;

f) a neutral endopeptidase (NEP) inhibitor, in particular wherein said NEP is EC 3.4.24.11, preferably wherein said NEP inhibitor is a selective inhibitor for EC 3.4.24.11; suitable NEP inhibitor compounds are described e.g. in WO 02/02513, EP1097719, WO 02/079143, EP1258474, WO2004/080985, in particular (2S)-2-{[1-({[3-(4-Chlorophenyl)propyl]amino}carbonyl)cyclopentyl]methyl}-4-methoxybutanoic acid and (R)-2-Methyl-3-(1-{[3-(2-methyl-1,3-benzothiazol-6-yl)propyl]carbamoyl}cyclopentyl) propanoic acid.

Suitable PDE5 inhibitors for treating MED include: the pyrazolo [4,3-d]pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in international patent application WO 93/06104; the isomeric pyrazolo [3,4-d]pyrimidin-4-ones disclosed in international patent application WO 93/07149; the quinazolin-4-ones disclosed in international patent application WO 93/12095; the pyrido [3,2-d]pyrimidin-4-ones disclosed in international patent application WO 94105661; the purin-6- ones disclosed in international patent application WO 94/00453; the pyrazolo [4,3-d]pyrimidin-7-ones disclosed in international patent application WO 98/49166; the pyrazolo [4,3-d]pyrimidin-7-ones disclosed in international patent application WO 99/54333; the pyrazolo [4,3-d]pyrimidin-4-ones disclosed in EP-A-0995751; the pyrazolo [4,3-d]pyrimidin-7-ones disclosed in international patent application WO 00/24745; the pyrazolo [4,3-d]pyrimidin-4-ones disclosed in EP-A-0995750; the compounds disclosed in international application WO95/19978; the compounds disclosed in international application WO 99/24433 and the compounds disclosed in international application WO 93/07124; the pyrazolo [4,3-d]pyrimidin-7-ones disclosed in international application WO 01/27112; the pyrazolo [4,3-d]pyrimidin-7-ones disclosed in international application WO 01/27113; the compounds disclosed in EP-A-1092718 and the compounds disclosed in EP-A-1092719.

Further suitable PDE5 inhibitors for the use according to the present invention include: 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); (+)-3-ethyl-5-[5-(4-ethylpiperazin-1-ylsulphonyl)-2-(2-methoxy-1(R)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15); 5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124); 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132); (6R,12aR)-2,3,6,7,12,12a-hexahydro-2-methyl-6-(3,4-methylenedioxyphenyl)pyrazino[2', 1':6,1]pyrido[3,4-b]indole-1,4-dione (tadalafil), i.e. the compound of examples 78 and 95 of international application WO95/19978, as well as the compound of examples 1, 3, 7 and 8; 242-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of international application WO99/24433; and the compound of example 11 of international application WO93/07124 (EISAI); and compounds 3 and 14 from Rotella D P, *J. Med. Chem.*, 2000, 43, 1257.

Still other suitable PDE5 inhibitors include: 4-bromo-5-(pyridylmethylamino)-6-[3-(4-chlorophenyl)-propoxy]-3 (2H)pyridazinone; 1-[4-[(1,3-benzodioxol-5-ylmethy)amino]-6-chloro-2-quinozolinyl]-4-piperidine-carboxylic acid, monosodium salt; (+)-cis-5,6a ,7,9,9,9a-hexahydro-2-[4-(trifluoromethyl)-phenyl methyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl)propoxy)-3-(2H)pyridazinone; 1-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)arnino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

Preferred PDE5 inhibitors include 5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil); (6R,12aR)-2,3,6,7,12,12a-hexahydro-2-methyl-6-(3,4-methylenedioxyphenyl)-pyrazino[2',1:6,1]pyrido[3,4-b]indole-1,4-dione (tadalafil); 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil); N-[[3-(4,7-dihydro-1-methyl-7-oxo-3-propyl-1H-pyrazolo[4,3-d]-pyrimidin-5-yl)-4-propxyphenyl]sulfonyl]-1-methyl2-pyrrolidinepropanamide (udenafil); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, and 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one and pharmaceutically acceptable salts thereof.

Suitable pharmaceutical agents that may be used in combination with the compounds of formula (I) for treating obesity and obesity-related eating disorders include anti-obesity agents such as apolipoprotein-B secretion/microsomal triglyceride transfer protein (apo-B/MTP) inhibitors (e.g., gut-selective MTP inhibitors, such as dirlotapide), 11β-hydroxy steroid dehydrogenase-1 (11β-HSD type 1) inhibitors, $PYY_{3-36}$ and analogs thereof, MCR-4 agonists, cholecystokinin-A (CCK-A) agonists, monoamine reuptake inhibitors (such as sibutramine), sympathomimetic agents, $\beta_3$ adrenergic receptor agonists, dopamine agonists (such as bromocriptine), melanocyte-stimulating hormone receptor analogs, cannabinoid 1 receptor antagonists (e.g., CB-1 selective antagonists, see below), melanin concentrating hormone antagonists, leptins (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists (e.g., NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345; and 6,326,375; US Publication Nos. 2002/0151456 and 2003/036652; and international patent applications Nos. WO 03/010175, WO 03/082190 and WO 021048152), thyromimetic agents, dehydroepiandrosterone or an analog thereof, glucocorticoid receptor agonists or antagonists, orexin receptor antagonists, urocortin binding protein antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, an opioid antagonist, neuromedin U receptor agonists, and ghrelin aptamers (e.g., Noxxon Spiegelmer). Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, CB-1 antagonists, gut-selective MTP inhibitors, pseudoephedrine, $PYY_{3-36}$ or an analog thereof, and 2-oxo-N-(5-phenylpyrazinyl)spiro-[isobenzofuran-1(3H),4'-piperidine]-1'-carboxamide. Preferably, the compounds of formula (I) and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; $PYY_{3-36}$ (including analogs thereof) can be prepared as described in US Publication No. 2002/0141985 and WO 03/027637; and the NPY Y5 receptor antagonist 2-oxo-N-(5-phenylpyrazinyl)spiro[isobenzofuran-1(3H),4'-piperidine]-1'-carboxamide can be prepared as described in US Publication No. 2002/0151456. Other NPY Y5 receptor antagonists described in international patent application WO 03/082190 that may be useful in combination with a compound of the present invention are selected from the group consisting of: 3-oxo-N-(5-phenyl-2-pyrazinyl)-spiro[isobenzofuran-1 (3H), 4'-piperidine]-1'-carboxamide; 3-oxo-N-(7-trifluoromethylpyrido[3,2-b]pyridin-2-yl)-spiro-[isobenzofuran-1 (3H), 4'-piperidine]-1'-carboxamide; N-[5-(3-fluorophenyl)-2-pyrimidinyl]-3-oxospiro-[isobenzofuran-1(3H), [4'-piperidine]-1'-carboxamide; trans-3'-oxo-N-(5-phenyl-2-pyrimidinyl)]spiro[cyclohexane-1,1'(3'H)-isobenzofuran]-4-carboxamide; trans-3'-oxo-N-[1-(3-quinolyl)-4-imidazolyl]spiro[cyclohexane-1,1'(3'H)isobenzofuran]-4-carboxamide; trans-3-oxo-N-(5-phenyl-2-pyrazinyl)spiro[4-azaiso-benzofuran-1(3H),1'-cyclohexane]-4'-carboxamide; trans-N-[5-(3-fluorophenyl)-2-pyrimidinyl]-3-oxospiro[5-azaisobenzofuran-1(3H), 1'-cyclohexane]-4'-carboxamide; trans-N-[5-(2-fluoraphenyl)-2-pyrimidinyl]-3-oxospiro[5-azaisobenzofuran-1(3H), 1'-cyclohexane}-4'-carboxamide; trans-N-[1-(3,5-difluorophenyl)-4-imidazolyl]-3-oxospiro [7-azaisobenzofuran-1(3H),1'-cyclohexane]-4'-carboxamide; trans-3-oxo-N-(1-phenyl-4-pyrazolyl)spiro[4-azaisobenzofuran-1(3H), 1'-cyclohexane]-4'-carboxamide; trans-N-[1-(2-fluorophenyl)-3-pyrazolyl]-3-oxospiro[6-azaisobenzofuran-1(3H), 1'-cyclohexane]-4'-carboxamide; trans-3-oxo-N-(l-phenyl-3-pyrazolyl)spiro[6-azaisobenzafuran-1(3H),1'-cyclohexane]-4'-carboxamide; trans-3-oxo-N-(2-phenyl-1,2,3-triazol-4-yl)spiro[6-azaisobenzofuran-1(3H),1'-cyclohexane]-4'-carboxamide; and pharmaceutically acceptable salts and esters thereof. All of the above recited U.S. patents and publications are incorporated herein by reference.

The CB-1 receptor antagonist is preferably selective to the CB-1 receptor. "CB-1 receptor selective" means that the compound has little or no activity to antagonize the cannabinoid-2 receptor (CB-2). More preferably, the CB-1 antagonist is at least about 10 fold more selective for the CB-1 receptor in comparison to the CB-2 receptor. For example, the inhibitory concentration ($IC_{50}$) for antagonizing the CB-1 receptor is about 10 or more times lower than the $IC_{50}$ for antagonizing the CB-2 receptor. Bioassay systems for determining the CB-1 and CB-2 binding properties and pharmacological activity of cannabinoid receptor ligands are described by Roger G. Pertwee in "Pharmacology of Cannabinoid Receptor Ligands" Current Medicinal Chemistry, 6, 635-664 (1999) and in WO 92/02640 (U.S. application Ser. No. 07/564,075 filed Aug. 8, 1990, incorporated herein by reference).

Suitable CB-1 receptor antagonists include compounds disclosed in U.S. Pat. Nos. 5,462,960; 5,596,106; 5,624,941; 5,747,524; 6,017,919; 6,028,084; 6,432,984; 6,476,060; 6,479,479; 6,518,264; and 6,566,356; U.S. Patent Publication Nos. 2003/0114495; 2004/0077650; 2004/0092520; 2004/0122074; 2004/0157838; 2004/0157839; 2004/0214837; 2004/0214838; 2004/0214855; 2004/0214856; 2004/0058820; 2004/0235926; 2004/0248881; 2004/0259887; 2005/0080087; 2005/0026983 and 2005/0101592; international patent applications WO 03/075660; WO 02/076949; WO 01/029007; WO 04/048317; WO 04/058145; WO 04/029204; WO 04/012671; WO 03/087037; WO 03/086288; WO 03/082191; WO 03/082190; WO 03/063781; WO 04/012671; WO 04/013120; WO 05/020988; WO 05/039550; WO 05/044785; WO 05/044822; WO 05/049615; WO 05/061504; WO 05/061505; WO 05/061506; WO 05/061507; and WO 05/103052: and U.S. Provisional Application Nos. 60/673535 filed on Apr. 20, 2005; and 60/673,546 filed on Apr. 20, 2005.

All of the above patents and patent applications are incorporated herein by reference. Preferred CB-1 receptor antagonists for use in the combination compositions and methods of the present invention include: rimonabant (SR141716A also known under the tradename Acomplia™) is available from Sanofi-Synthelabo or can be prepared as described in U.S. Pat. No. 5,624,941; N-(piperidin-1-yl)-1-(2,4-dichlorophenyl)-5-(4-iodophenyl)-4-methyl-1H-pyrazole-3-carboxamide (AM251) is available from Tocris™, Ellisville, Mo.; [5-(4-bromophenyl)-1-(2,4-dichloro-phenyl)-4-ethyl-N-(1-piperidinyl)-1H-pyrazole-3-carboxamide] (SR147778) which can be prepared as described in U.S. Pat. No. 6,645,985; N-(piperidin-1-yl)-4,5-diphenyl-1-methylimidazole-2-carboxamide, N-(piperidin-1-yl)-4-(2,4-dichlorophenyl)-5-(4-chlorophenyl)-1-methylimidazole-2-carboxamide, N-(piperidin-1-yl),4,5-di-(4-methylphenyl)-1-methylimidazole-2-carboxamide, N-cyclohexyl-4,5-di-(4-methylphenyl)-1-methylimidazole-2-carboxamide, N-(cyclohexyl)-4-(2,4-dichlorophenyl)-5-(4-chlorophenyl)-1-methylimidazole-2-carboxamide, and N-(phenyl)-4-(2,4-dichlorophenyl)-5-(4-chlorophenyl)-1-methylimidazole-2-carboxamide which can be prepared as described in WO 03/075660; the hydrochloride, mesylate and besylate salt of 1-[9-(4-chloro-phenyl)-8-(2-chloro-phenyl)-9H-purin-6-yl]-4-ethylamino-piperidine-4-carboxylic acid amide which can be prepared as described in U.S. Patent Publication No. 2004/0092520; 1-[7-(2-chloro-phenyl)-8-(4-chloro-phenyl)-2-methyl-pyrazolo[1,5-a][1,3,5]triazin-4-yl]-3-ethylamino-azetidine-3-carboxylic acid amide and 1-[7-(2-chloro-phenyl)-8-(4-chloro-phenyl)-2-methyl-pyrazolo[1,5-a][1,3,5]triazin-4-yl]-3-methylamino-azetidine-3-carboxylic acid amide which can be prepared as described in U.S. Patent Publication No.

2004/0157839; 3-(4-chloro-phenyl)-2-(2-chloro-phenyl)-6-(2,2-difluoro-propyl)-2,4,5,6-tetrahydro-pyrazolo[3,4-c]pyridin-7-one which can be prepared as described in. U.S. Patent Publication No. 2004/0214855; 3-(4-chloro-phenyl)-2-(2-chloro-phenyl)-7-(2,2-difluoro-propyl)-6,7-dihydro-2H,5H-4-oxa-1,2,7-triaza-azulen-8-one which can be prepared as described in U.S. Patent Publication No. 2005/0101592; 2-(2-chloro-phenyl)-6-(2,2,2-trifluoro-ethyl)-3-(4-trifluoromethyl-phenyl)-2,6-dihydro-pyrazolo[4,3-d]pyrimidin-7-one which can be prepared as described in U.S. Patent Publication No. 2004/0214838; (S)-4-chloro-N-{[3-(4-chloro-phenyl)-4-phenyl-4,5-dihydro-pyrazol-1-yl]-methylamino-methylene}-benzenesulfonamide (SLV-319) and (S)-N-{[3-(4-chloro-phenyl)-4-phenyl-4,5-dihydro-pyrazol-1-yl]-methylamino-methylene}-4-trifluoromethyl-benzenesulfonamide (SLV-326) which can be prepared as described in WO 02/076949; N-piperidino-5-(4-bromophenyl)-1-(2,4-dichloraphenyl)-4-ethylpyrazole-3-carboxamide which can be prepared as described in U.S. Pat. No. 6,432,984; 1-[bis-(4-chloro-phenyl)-methyl]-3-[(3,5-difluoro-phenyl)-methanesulfonyl-methylene]-azetidine which can be prepared as described in U.S. Pat. No. 6,518,264; 2-(5-(trifluoromethyl)pyridin-2-yloxy)-N-(4-(4-chlorophenyl)-3-(3-cyanophenyl)butan-2-yl)-2-methylpropanamide which can be prepared as described in WO 04/048317; 4-{[6-methoxy-2-(4-methoxyphenyl)-1-benzofuran-3-yl]carbonyl}benzonitrile (LY-320135) which can be prepared as described in U.S. Pat. No. 5,747,524; 1-[2-(2,4-dichlorophenyl)-2-(4-fluorophenyl)-benzo[1,3]dioxole-5-sulfonyl]-piperidine which can be prepared as described in WO 04/013120; and [3-amino-5-(4-chlorophenyl)-6-(2,4-dichlorophenyl)-furo[2,3-b]pyridin-2-yl]-phenyl-methanone which can be prepared as described in WO 04/012671.

Suitable intestinal-acting MTP inhibitors for use in the combinations, pharmaceutical compositions, and methods of the invention include dirlotapide ((S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide) and 1-methyl-5-[(4'-trifluoromethyl-biphenyl-2-carbonyl)-amino]-1H-indole-2-carboxylic acid (carbamoyl-phenyl-methyl)-amide which can both be prepared using methods described in U.S. Pat. No. 6,720,351; (S)-2-[(4'-trifluoromethyl-biphenyl-2-carbonyl)-amino]-quinoline-6-carboxylic acid (pentylcarbamoyl-phenyl-methyl)-amide, (S)-2-[(4'-tert-butyl-biphenyl-2-carbonyl)-amino]-quinoline-6-carboxylic acid {[(4-fluoro-benzyl)-methyl-carbamoyl]-phenyl-methyl}-amide, and (S)-2-[(4'-tert-butyl-biphenyl-2-carbonyl)-amino]-quinoline-6-carboxylic acid [(4-fluoro-benzylcarbamoyl)-phenyl-methyl]-amide which can all be prepared as described in U.S. Provisional Patent Application Ser. No. 60/541,678 filed on Feb. 4, 2004; (−)-4-[4-[4-[[(2S,4R)-2-(4-chlorophenyl)-2-[[(4-methyl-4H-1,2,4-triazol-3-yl)sulfanyl]methyl-1,3-dioxolan-4-yl]methoxy]phenyl]piperazin-1-yl]phenyl]-2-(1R)-1-methylpropyl]-2,4-dihydro-3H-1,2,4-triazol-3-one (also known as Mitratapide or R103757) which can be prepared as described in U.S. Pat. Nos. 5,521,186 and 5,929,075; and implitapide (BAY 13-9952) which can be prepared as described in U.S. Pat. No. 6,265,431. Most preferred is dirlotapide, mitratapide, (S)-2-[(4'-trifluoromethyl-biphenyl-2-carbonyl)-amino]-quinoline-6-carboxylic acid (pentylcarbamoyl-phenyl-methyl)-amide, (S)-2-[(4'-tert-butyl-biphenyl-2-carbonyl)-amino]-quinoline-6-carboxylic acid {[(4-fluoro-benzyl)-methyl-carbamoyl]-phenyl-methyl}-amide, or (S)-2-[(4'-tert-butyl-biphenyl-2-carbonyl)-amino]-quinoline-6-carboxylic acid [(4-fluoro-benzylcarbamoyl)-phenyl-methyl]-amide. Suitable antipsychotic agents (or neuroleptic agents) which may be used in combination with the compounds of formula (I) include ziprasidone (e.g., GEODON®), risperidone (e.g., RISPERDAL®), olanzapine (e.g., ZYPREXA®), quetiapine (e.g., SEROQUEL®), clozapine (e.g., CLOZARIL®), haloperidol (e.g., HALDOL®) and pharmaceutically acceptable salts thereof. Ziprasidone (5-(2-(4-(1,2-benzisothiazol-3-yl)-piperazinyl)ethyl)-6-chloro-1,3-dihydro-2H-indol-2-one hydrochloride) may be purchased or prepared using the methods described in U.S. Pat. Nos. 4,831,031; 5,312,925; and 6,150,366. Risperidone (3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one) may be purchased or prepared using the methods described in U.S. Pat. Nos. 4,804,663; 5,453,425; and 5,616,587. Olanzapine (2-Methyl-10-(4-methyl-1-piperazinyl)-4H-thieno-[2,3-b][1,5]benzodiazepine) may be purchased or prepared using the procedures described in U.S. Pat. No. 5,229,382. Quetiapine (11-[4-[2-(2-Hydroxyethoxy)ethyl]-1-piperazinyl]dibenzo[b,f][1,4]thiazepine) may be purchased or prepared using the procedures described in U.S. Pat. No. 4,879,288. Suitable pharmaceutical agents that may be used in combination with the compounds of formula (I) for treating low urinary tract symptoms include PDE5 inhibitors (such as those described above); 5-alpha reductase inhibitors (e.g., finasteride, dutasteride, izonsteride; idronoxil, epristeride); muscarinic antagonists (e.g., atropine, fluvoxate, hyoscine, oxybutynin, darifenacin, tolterodine, (+)-N,N-diisopropyl-3-(2-hydroxy-5-hydroxymethylphenyl)-3-phenylpropylamine, propantheline, propiverine, trospium, solifenacin, fesoterodine); alpha adrenergic receptor antagonists, in particular alpha1 adrenergic receptor antagonists (e.g., doxazosin, terazosin, prazosin, tamsulosin, alfuzosin) or alpha2 adrenergic receptor antagonists (e.g., idazoxan, efaroxan, yohimbine); antagonists or modulators for vasopressin receptors, especially $V_{1A}$ antagonists, such as relcovaptan (SR 49059), conivaptan, atosiban, VPA-985, CL-385004, Vasotocin™.

Other suitable pharmaceutical agents that may be administered in combination with the compounds of the present invention include agents designed to treat tobacco abuse (e.g., nicotine receptor partial agonists (e.g. varenicline), bupropion hypochloride (also known under the tradename Zyban™) and nicotine replacement therapies), ADD/ADHD agents (e.g., Ritalin™, Strattera™, Concerta™ and Adderall™), antidepressants (e.g., fluoxetine hydrochloride (Prozac™); cognitive improvement agents (e.g., donepezil hydrochloride (Aircept™) and other acetylcholinesterase inhibitors); neuroprotective agents (e.g., memantine); and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA). In addition to Zyban, other useful nicotine receptor partial agonists are described in U.S. Pat. Nos. 6,235,734; 6,410,550; and 6,462,035; all of which are incorporated herein by reference.

Other pharmaceutical agents that may be used in combination include anti-inflammatory agents (e.g., COX-2 inhibitors); antihypertensive agents; insulin and insulin analogs (e.g., LysPro insulin); GLP-1 (7-37) (insulinotropin) and GLP-1 (7-36)-NH$_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actos™ (pioglitazone), englitazone, troglitazone, darglitazone, Avandia™ (rosiglitazone; BRL49653); fatty acid oxidation inhibitors: clomoxir, etomoxir; ☐glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan™) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate (e.g., fenofibrate; Tricor™), an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, *Hoodia* plant extracts, and niacin.

Preferred agents for coadministration with the compounds of formula (I) are PDE5 inhibitors, vasopressin V$_{1A}$ antagonists, α-adrenergic receptor antagonists, NEP inhibitors, dopamine agonists, melanocortin receptor agonists, anti-obesity agents, and anti-psychotic agents, as described above.

Such combinations may offer significant advantages, including synergistic activity, in therapy.

If a combination of active agents is administered, then they may be administered simultaneously, separately or sequentially, in formulations which may be the same or different.

General Methods

The routes below, including those mentioned in the Examples and Preparations, illustrate methods of synthesising compounds of formula (I). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example:

"Comprehensive Organic Transformations" by R C Larock, VCH Publishers Inc. (1989); Advanced Organic Chemistry" by J. March, Wiley Interscience (1985);

"Designing Organic Synthesis" by S Warren, Wiley Interscience (1978); "Organic Synthesis—The Disconnection Approach" by S Warren, Wiley Interscience (1982);

"Guidebook to Organic Synthesis" by R K Mackie and D M Smith, Longman (1982);

"Protective Groups in Organic Synthesis" by T W Greene and P G M Wuts, John Wiley and Sons, Inc. (1999); and "Protecting Groups" by P J, Kocienski, Georg Thieme Verlag (1994); and any updated versions of said standard works.

In the following general methods, $R^1$, $R^2$, $R^{3a}$, $R^{3b}$, $R^{3c}$ and $R^{3d}$ are as previously defined for a compound of formula (I) unless otherwise stated, and wherein $R^{100}$ is H. Compounds of formula (I) wherein $R^{100}$ is other than H can be prepared according to *Design of Prodrugs* by H. Bundgaard (Elsevier, 1985) and Fleischer et al, *Advanced Drug Delivery Reviews*, 19(1996), 115-130, mentioned hereinbefore, for example, from compounds wherein $R^{100}$ is H.

In one embodiment, compounds of formula (I) can be prepared as described in Scheme 1 below.

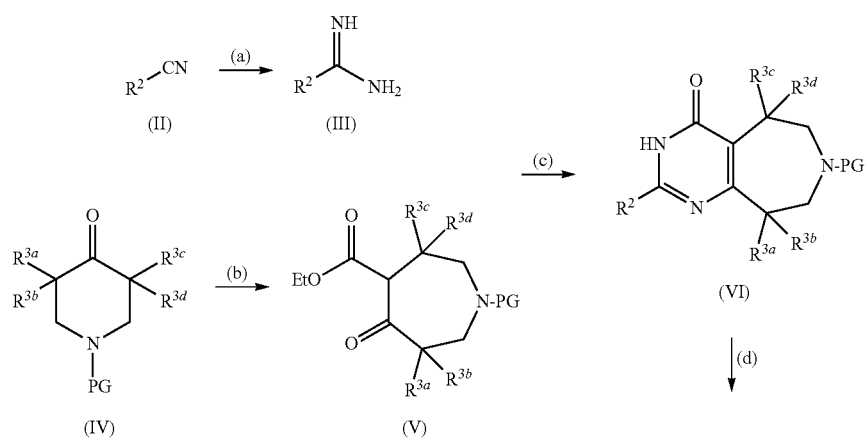

Scheme 1

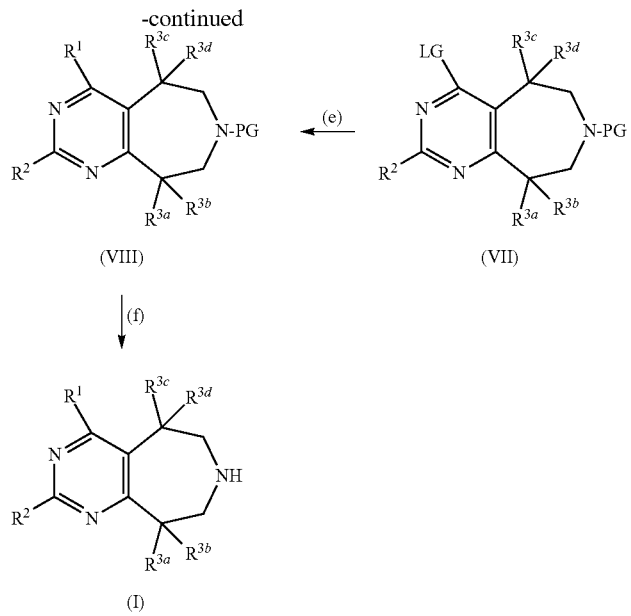

PG is a suitable protecting group, preferably benzyl, boc, benzyl carbamoyl or ethyl carbamoyl. LG is a suitable leaving group, preferably triflate, mesityl, mesylate and, more preferably, chloro.

Compounds of general formula (IV) are available commercially or according to methods known to one skilled in the at For example, compounds of general formula (IV) where PG=Boc and $R^{3a}$=H or Me are available commercially (Acros, Fluka, Pharmabridge, Maybridge). When PG=Benzyl and $R^{3a}$=H or Me, compounds of general formula (IV) are available commercially (Appallo, Aldrich, Fluorochem). When PG=benzyl carbamoyl and $R^{3a}$=H or Me, compounds of general formula (IV) are available commercially (Aldrich, ASDI) or can be prepared by protection of the corresponding commercial piperidone, using standard methodology as described in "Protecting Groups in Organic Synthesis" by T. W. Greene and P. Wutz. Typical conditions comprise reaction of the piperidone with a suitable base such as triethylamine and benzyl chloroformate in a suitable organic solvent such as dichloromethane. When PG=ethyl carbamoyl and $R^{3a}$=H or Me, compounds of general formula (IV) are available commercially (ASDI, Aldrich, Apollo) or can be prepared by the methodology described in International Patent Application WO2002085886.

Compounds or general formula (II) are either available commercially (Aldrich, Lancaster, ASDI) or known in the literature.

Step (a)

Compounds of the general formula (III) can be prepared from compounds of the general formula (II) by methodology described in the literature (See Eur. J. Med. Chem (1981), 16, 175 or Tet. Lett. (1985), 36, 8761). Typically, compound (II) is stirred in a saturated ethanolic hydrogen chloride solution and the resulting mixture treated with a saturated ethanolic ammonia solution.

Alternatively compounds of the general formula (III) can be prepared from compounds of the general formula (II) in the presence of trimethylaluminium and ammonium chloride in a suitable organic solvent such as toluene at 0° C. then at elevated temperature for 18 hours.

Step (b)

Compounds of the general formula (V) can be prepared from compounds of the general formula (IV) using the methodology described in Synth. Comm. (1992), 22(9), 1249. Typical conditions comprise the simultaneous addition of separate solutions of boron trifluoride diethyl etherate in diethyl ether and ethyl diazoacetate in diethyl ether to a solution of piperidone (IV) in diethyl ether at −20° C. then at ambient temperature for 18 hours.

Step (c)

Compounds of the general formula (VI) can be prepared by reaction of compound (V) and compound (III), for example, in the presence of a suitable base such as sodium ethoxide or sodium methoxide in an organic solvent such as ethanol or methanol. Typically, 1.0 equivalent of amidine (III) is reacted with 1.0 equivalent of compound (V) and 1-3 equivalents of sodium methoxide in methanol at ambient temperature for 18 hours.

Step (d)

Compounds of the general formula (VII) can be prepared from compounds of the general formula (VI) using methods known to one skilled in the art. For example, halopyrimidines where LG is chloride or bromide may be obtained by treatment of compounds (VI) with $POCl_3$, $PCl_3$, $PCl_5$, $PBr_3$ or $POBr_3$. Typically, compound (VI) is reacted with an excess of phosphorous oxychloride and a suitable additive such as N,N-dimethylalanine or tetraethyl ammonium chloride in a solvent such as proprionitrile or acetonitrile at elevated temperature for 4 hours.

Alternatively, compounds of general formula (VII) where LG is triflyl can be prepared from compounds of general formula (VI) in the presence of a triflating agent such as triflic anhydride and a suitable base such as pyridine in a suitable solvent such as dichloromethane. Typically, compound (VI) is reacted with triflic anhydride and pyridine in dichloromethane at 0° C. then at ambient temperature for 4 hours.

Alternatively, compounds of general formula (VII) where LG is mesyl or mesityl can be prepared from compounds of general formula (VI) in the presence of a sulfonyl chloride such as mesyl chloride or mesityl chloride, a suitable base such as triethylamine in a suitable organic solvent such as dichloromethane. Typically, compound (VI) is reacted with 1.0 equivalent of mesyl chloride, 2.0 equivalents of triethylamine in dichloromethane.

Step (e)

Compounds of the general formula (VIII) can be prepared from compounds of the general formula (VII). Preferable conditions where $R^1$=H include addition of a suitable metal catalyst (preferably, palladium acetate) and a suitable phosphorous containing ligand preferably, 1,1'-Bis(diphenylphosphino)ferrocene) (dppf). The reaction may be carried out in a solvent such as N,N-dimethylformamide in the presence of formic acid and a suitable base such a triethylamine. Alternatively, the reaction may be carried out in the presence of a suitable metal catalyst, such as palladium on carbon, with ammonium formate in a solvent such as methanol at elevated temperature.

Alternatively, compounds of the general formula (VIII) may be prepared in the presence of a suitable metal such as zinc and a suitable base such as ammonium hydroxide. The reaction may be carried out in a solvent such as tetrahydrofuran at elevated temperature.

Where $R^1$ contains an amine group, compounds of formula (VIII) may be prepared by addition of the required primary or secondary amine (HNR$^4$R$^5$) in a suitable solvent as tetrahydrofuran, acetonitrile, N,N-dimethylacetamide or 1-methyl-2-pyrrolidinone at either ambient or elevated temperatures. A microwave oven may be used to increase reaction rates. Typically, an excess solution of amine is added to compounds of general formula (VII) in acetonitrile at ambient temperature.

Where $R^1$ is an alkoxy group, compounds of formula (VIII) may be prepared by reacting the compound (VII) with the relevant alcohol in the presence of a suitable base such as cesium carbonate in a solvent such as acetonitrile or methanol. Typically, compound (VII) is reacted with sodium methoxide in methanol at elevated temperature for 18 hours.

Treatment of alkyl boronic acids, or their boronic ester counterparts, with the triflates, bromides or chlorides or halides of formula (VII), in the presence of a catalyst such as palladium acetate and a suitable phosphorous containing ligand such as tricyclohexyl phosphine provides compounds of formula (VIII) where $R^1$ is a C-linked alkyl moiety. Typically, a compound of formula (VII) is reacted with an alkyl-boronic acid in a solvent such as acetonitrile or toluene in the presence of palladium acetate.

Step (f)

Compounds of general formula (I) can be prepared by deprotection of compounds (VIII) using standard methodology as described in "Protecting Groups in Organic Synthesis" by T. W. Greene and P. Wutz.

More specifically, when PG=Boc, compounds (VIII) are typically treated with a suitable acid such as 4M-6M hydrochloric acid or trifluoroacetic acid in a suitable solvent such as dichloromethane or dioxane at ambient temperatures for 1-18 hours. When PG=benzyl, typical conditions for removal of the benzyl group comprise treatment of compounds (VIII) with a suitable hydrogen transfer agent such as chloroethyl chloroformate in the presence of a suitable base such as diisopropylethylamine or 1,8-bis(dimethylamino)naphthalene) or ammonium formate with 10% palladium on charcoal (or 20% palladium hydroxide) in the presence of 1-methyl-1,4-cyclohexadiene in a suitable solvent such as dichloromethane or ethanol at ambient or elevated temperatures for 1-18 hours.

When PG=ethyl carbamoyl, compounds (VIII) are typically treated with 4M-6M hydrochloric acid, at elevated temperature for 18 hours. Alternatively, compounds of general formula (VIII) can be reacted with potassium hydroxide in a solvent such as ethylene glycol at elevated temperature for 18-72 hours.

When PG=benzylcarbamoyl, compounds (VIII) are typically reacted in a hydrogen atmosphere with a suitable palladium catalyst in a solvent such as ethanol. The compounds of general formula (I) can also be prepared from compounds of general formula (VIII) with a suitable hydrogen transfer agent such as 1-methyl-1,4-cyclohexadiene in the presence of a suitable metal catalyst such as 10% palladium on charcoal in a solvent such as ethanol. Alternatively, compounds of general formula (VIII) can be treated with 48% aqueous hydrogen bromide at ambient temperature for 3 hours.

Alternatively, embodiments of compounds of the general formula (I) where $R^1$ is $(C_1-C_4)$alkoxy, fluoro$(C_1-C_4)$alkoxy may be prepared according to Scheme 2.

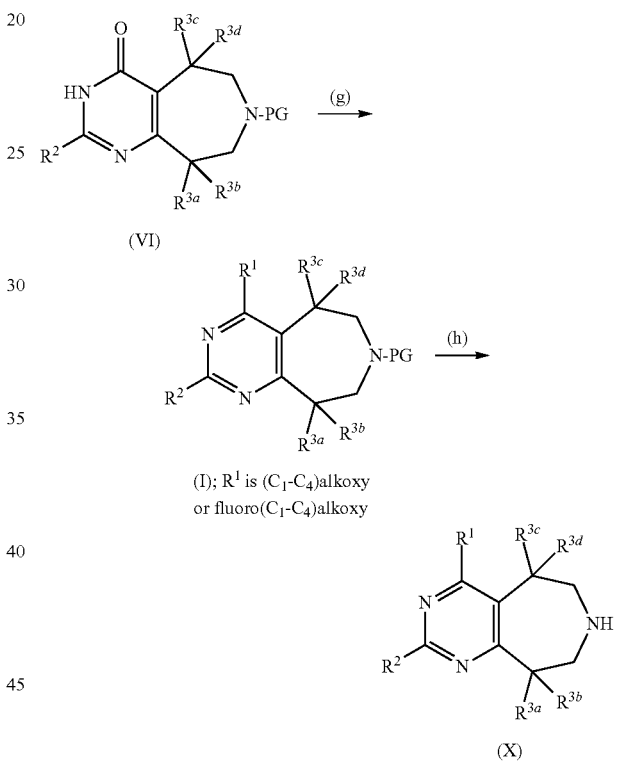

Scheme 2

Compounds of the general formula (VI) can be made in the same way as described in Scheme 1 and protecting groups may be used in exactly the same way as for Scheme 1, including their methods of removal.

Step (g)

Compounds of general formula (I) where $R^1$ is $(C_1-C_4)$ alkoxy, fluoro$(C_1-C_4)$alkoxy can be prepared from compounds of general formula (VI) on reaction with the appropriate alkyl halide, such as methyl iodide, in the presence of a base such as potassium carbonate in a suitable solvent like N,N-dimethylformamide. Typical conditions comprise treatment of compound (VI) with methyl iodide and potassium carbonate in N,N-dimethylformamide at ambient temperature for 18-72 hours. Alternatively, compounds of general formula (I) where $R^1$ is methoxy can be prepared from compounds (VI) on treatment with trimethyloxonium tetrafluoroborate in dichloromethane at ambient temperature for 2-18 hours.

Step (h)

Compounds of general formula (X) can be prepared by deprotection of compounds (VII) using standard methodology as described in "Protecting Groups in Organic Synthesis" by T. W. Greene and P. Wutz.

Alternatively, compounds of the general formula (XII) which are embodiments of compounds of the general formula (VI), where $R^2$ is $-NR^7R^8$ or $-NR^9-(CH_2)_p$-phenyl, wherein in each instance the phenyl radical is optionally substituted by up to four groups selected from amino, $-NH[(C_1-C_4)alkyl]$, $-N[(C_1-C_4)alkyl]_2$, hydroxyl, halogen, cyano, $(C_1-C_4)alkyl$, fluoro$(C_1-C_4)alkyl$, $(C_1-C_4)alkoxy$, fluoro$(C_1-C_4)alkoxy$, said alkyl and alkoxy being optionally substituted by one or more hydroxyl, may be prepared according to Scheme 3.

Scheme 3

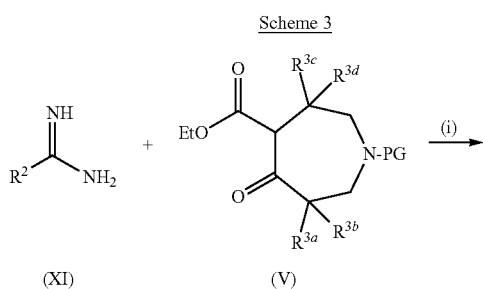

(XI)  (V)

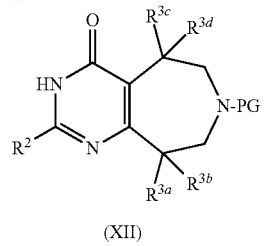

(XII)

Compounds of the general formula (V) can be made in the same way as described in Scheme 1 and protecting groups can be used in exactly the same way as for scheme 1, including their methods of removal. Guanidines of general formula (XI) are commercially available. (Aldrich, Fluorochem, TCI).

Compounds of the general formula (XII) can be prepared by reaction of compound (V) and compound (XI) in the presence of a suitable base such as sodium ethoxide or sodium methoxide in an organic solvent such as ethanol or methanol. Typical conditions comprise of 1.0 equivalent of guanidine (XI), 1.0 equivalent of compound (V) and 1-3 equivalents of sodium methoxide in methanol at ambient temperature for 18 hours.

Alternatively, embodiments of compounds of the general formula (I) where $R^1=H$ and $R^2$ is $-NR^7R^8$ or $-NR^9-(CH_2)_p$-phenyl i.e. compounds of the general formula (XV) may be prepared as shown in Scheme 4.

Scheme 4

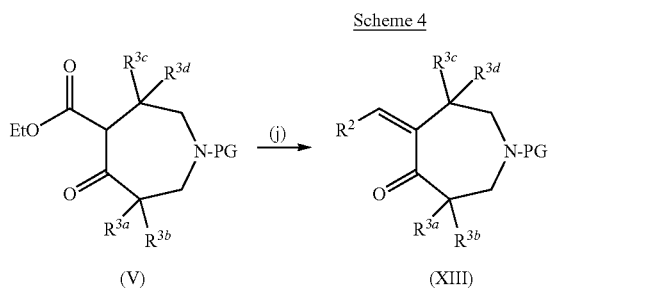

(V)  (XIII)

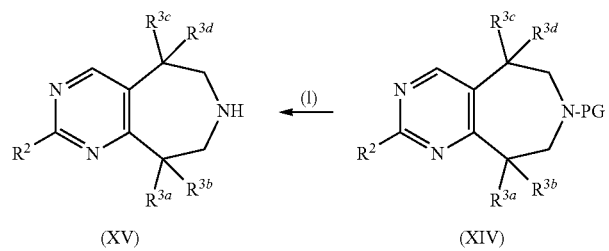

(XV)  (XIV)

Compounds of the general formula (V) can be made in the same way as described in Scheme 1 and protecting groups can be used in exactly the same way as for scheme 1, including their methods of removal.

Step (j)

Compounds of the general formula (XIII) can be prepared by reaction of compound (V) in the presence of dimethylformamide dimethyl acetal at elevated temperatures for 18 hours.

Step (k)

Compounds of the general formula (XIV) can be prepared by reaction of compound (XIII) and a suitable salt of compounds of general formula (XI) in the presence of a suitable base such as potassium carbonate in a solvent such as ethanol. Typical conditions comprise of treatment of compound (XIII) and the hydrochloride salt of compound (XI) (1.05 equivalent) in ethanol with potassium carbonate (1.05 equivalent) at elevated temperatures for 18 hours.

Step (l)

Compounds of general formula (XIV) can be prepared by deprotection of compounds (XIVI) using standard methodology as described in "Protecting Groups in Organic Synthesis" by T. W. Greene and P. Wutz.

Alternatively, embodiments of compounds of the general formula (I) where $R^1$ is —$NR^4R^5$ and $R^2$ is —$NR^7R^8$ i.e. compounds of the general formula (XX) may be prepared as shown in Scheme 5.

PG is a suitable protecting group, preferably Boc. LG is a suitable leaving group, preferably chloro.

Compounds of the general formula (V) can be made in the same way as described in Scheme 1 and protecting groups can be used in exactly the same way as for scheme 1, including their methods of removal.

Step (m)

Compounds of the general formula (XVI) can be prepared by reaction of compound (V) and thiourea, in the presence of a suitable base such as sodium ethoxide or sodium methoxide in an organic solvent such as ethanol or methanol. Typically, 1.0 equivalent of thiourea is reacted with 1.0 equivalent of compound (V) and 1-3 equivalents of sodium methoxide in methanol at room temperature for 18 hours Step (n)

Compounds of the general formula (XVII) can be prepared from compounds of the general formula (XVI) using methods known to one skilled in the art. For example, halopyrimidines where LG is chloride or bromide may be obtained by treatment of compounds (XVI) with $POCl_3$, $PCl_3$, $PCl_5$, $PBr_3$ or $POBr_3$. Typically, compound (XVI) is reacted with an excess of phosphorous oxychloride in a solvent such as dimethylformamide at elevated temperature.

Step (o)

Compounds of formula (XVIII) may be prepared from compounds (XVII) by addition of the required amine ($HNR^4R^5$), in the presence of a base such as potassium car-

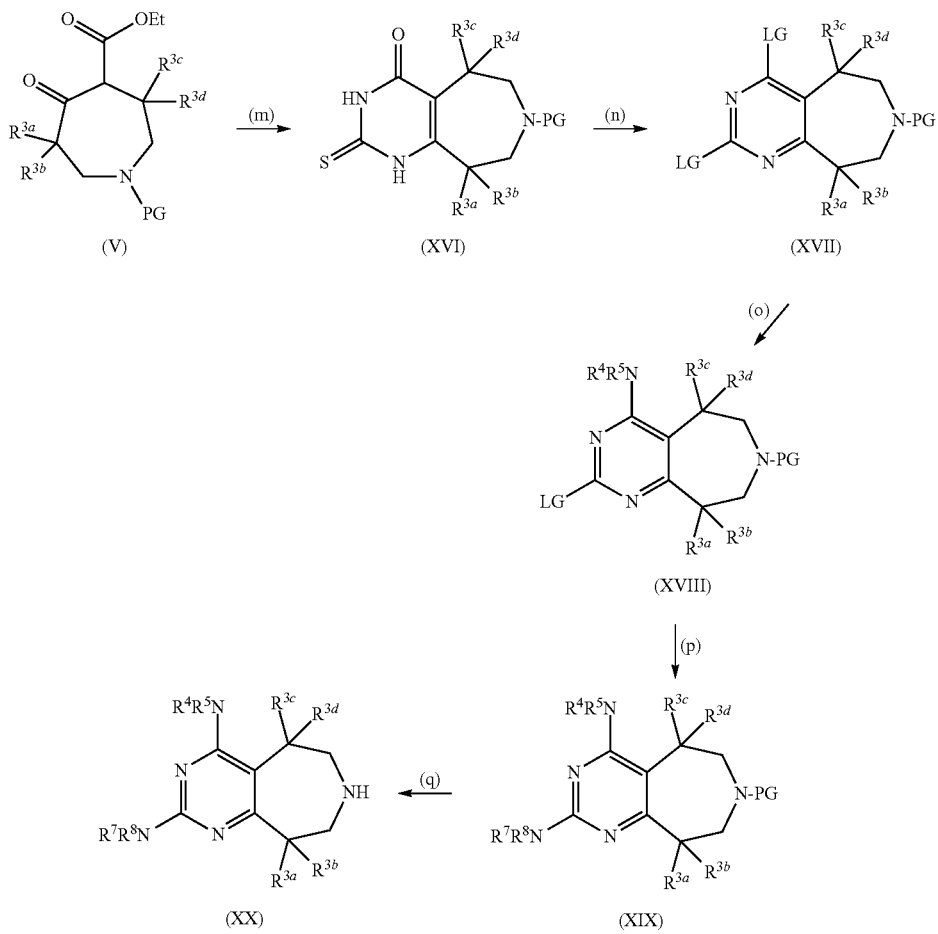

Scheme 5 bonate, in a suitable solvent such as tetrahydrofuran, acetonitrile, N,N-dimethylacetamide or 1-methyl-2-pyrrolidinone. Typical conditions comprise treatment of compound (XVII) with an excess of amine and potassium carbonate in tetrahydrofuran at elevated temperature.

Step (p)

Compounds of formula (XIX) can be prepared from compounds (XVIII) by addition of the required amine ($HNR^7R^8$), in the presence of a suitable catalyst and a suitable ligand. Typical conditions comprise reaction of (XVII) with an excess of amine, a palladium containing catalyst (preferably, tris-(dibenzylideneacetone)dipalladium(0)) and a phosphorous containing ligand (preferably, 2,2'-bis(diphenylphosphino)-1,1'-binaphthyl). The reaction may be carried out in a solvent such as toluene in the presence of a suitable base such a sodium t-butoxide at elevated temperature.

Step (q)

Compounds of general formula (XX) can be prepared by deprotection of compounds (XIX) using standard methodology as described in scheme 1. More specifically, compounds (XIX) are typically treated with a suitable acid such as 4M-6M hydrochloric acid or trifluoroacetic acid in a suitable solvent such as dichloromethane or dioxane at ambient temperatures for 1-18 hours.

The present invention also encompasses any one or more of these processes for preparing the compounds of formula (I), in addition to any novel intermediates used therein. According to a further aspect the present invention provides novel intermediate compounds of general formula (VI), (VII), (VIII), (XVI), (XVII), (XVIII) and (XIX), all salts, solvates and complexes thereof and all solvates and complexes of salts thereof as defined hereinbefore for compounds of formula (I). The invention includes all polymorphs of the aforementioned species and crystal habits thereof.

Biological Assays

The compounds of the invention were evaluated for biological activity by measuring the agonist affinity ($EC_{50}$) and efficacy ($E_{max}$) at the human recombinant 5-$HT_{2c}$ receptor expressed in CHO K1 cells, using a fluorescent based $Ca^{2+}$ mobilisation assay format compatible with FLIPR technology (Method 1). Additionally, the binding activity of a compound was determined by measuring its affinity for the human recombinant 5-$HT_{2c}$ receptor membranes from Swiss 3T3 cells (Method 2).

Method 1

The agonist affinity of the compounds were tested by measuring their ability to induce a fluorescent based $Ca^{2+}$ mobilization signal in a FLIPR assay using CHO K1 cells expressing recombinant human 5-$HT_{2c}$ receptor. Both agonist affinity ($EC_{50}$) and efficacy ($E_{max}$) were determined.

Cell Culture

Chinese hamster ovary cells (CHO K1) stably transfected with the 5-$HT_{2c}$ receptor were cultured under standard cell culture techniques. Specifically, cells were grown at 37° C. and 5% $CO_2$ in Dulbecco's Modified Eagle's Medium (DMEM) culture media supplemented with 10% dialysed foetal calf serum (FCS), 1% non-essential amino acids, 1 mM sodium pyruvate, 800 µg/mL geneticin and 50 µg/ml zeocin. Cells were harvested for passaging and storage using trypsin-EDTA, centrifugation and resuspension in culture medium. Cells were grown to 60-80% confluency, harvested and adjusted to 15-20×10⁶ cells/ml/vial in medium/10% DMSO and stored long-term at −80° C.

Preparation of Cell Plates

Cells were seeded into black-walled clear-bottomed 384 well plates 24 h before use. Frozen cells were defrosted in a 37° C. water bath and immediately transferred into 1 mL/vial 37° C. culture medium, diluted to 10 ml and DMSO removed by centrifugation. The cells were resuspended in 15 ml/vial of cell culture medium, counted and adjusted to give 500,000 cells/mL (10,000 cells/well). 200 µL/well of cell suspension was added to the 384 well plates which were then incubated overnight at 37° C.

Preparation of Compound Plates

Test compounds were prepared at 4 mM in 100% dimethyl sulphoxide (DMSO) and diluted in Dulbeccos PBS (+$CaCl_2$, +$MgCl_2$) with 0.9% DMSO and 0.05% pluronic F-127 to give appropriate test concentrations. The maximum agonist response was determined with 5-HT at a final assay concentration of 10 µM in the diluent above. The minimum response was determined with Dulbeccos PBS (+$CaCl_2$, +$MgCl_2$) with 0.9% DMSO and 0.05% pluronic F-127. Test compounds, maximum and minimum controls were added to a 384 well polypropylene plate.

Preparation of FLIPR Dye

The FLIPR calcium assay reagent was diluted with assay buffer (Hank's Balanced Salt Solution (HBSS))/20 mM HEPES and 2.5 mM probenecid (diluted with 1M Sodium hydroxide and DPBS (+$CaCl_2$, +$MgCl_2$)).

Running the Assay Using FLIPR

20 µl/well FLIPR calcium assay reagent was added to the cell plates, which were incubated for 1 h at 37° C. Cell plates and compound plates were then transferred onto the FLIPR. The assay was run using the appropriate FLIPR program, which initiates the reaction by transferring 15 µL compound into the corresponding, well of the cell plate.

Data Analysis

The statistical parameter exported from each well was the max peak height of the response. The mean minimum was subtracted from all values and then the activity was expressed as a percentage of the mean maximal response to 10 µM 5-HT and dose-response curves plotted from which both agonist affinity ($EC_{50}$) and efficacy ($E_{max}$) were determined.

Method 2

The compounds were tested for biological activity by their ability to inhibit binding of the radioligand $^3$H-meselurgine at the human recombinant 5-$HT_{2c}$ receptor expressed in the Swiss 3T3 cells using a scintillation proximity assay (SPA) technology.

Cell Culture

Swiss 3T3 stably transfected with the 5-$HT_{2c}$ receptor were cultured under standard cell culture techniques. Specifically, cells were grown in 50 mL growth medium (Dulbecco's Modified Eagle's Medium (DMEM) culture media supplemented with 10% dialysed foetal calf serum (FCS), 2 mM penicillin/streptomycin and 20 µg/mL geneticin) in 225 cm² flasks at 37° C. and 5% $CO_2$. Cells were grown to 60-80% confluency, harvested using trypsin-EDTA and pelleted by centrifugation for long-term storage at −80° C.

Cell Membrane Preparation

Cell pellets were thawed on ice and resuspended in 3 mL of membrane preparation buffer (see Media and Buffers for composition) per 1 mL of packed cell. The suspension was homogenised on ice for several 5 s intervals using a hand-held homogeniser. The homogenate was then centrifuged at 1,000 rpm for 5 min at 4° C.

The supernatants were then collected and retained. Initial cell & nuclei pellets (P1) were subsequently rehomogenised and centrifuged using the conditions cited above, and the supernatants collected and pooled with those retained from the first spin.

The pooled supernatants were centrifuged at 19,500 rpm for 45 min at 4° C., and the supernatants discarded. The pellets (P2) were then resuspended in 3 mL of membrane preparation buffer per 1 mL of the original packed cell volume. Protein concentrations were subsequently measured and the membrane suspension was finally frozen in aliquots of set volume and stored at −80° C. prior to use in assays.

Determination of Optimal Assay Conditions for Individual Membranes

For each batch of membrane used, optimal concentrations of Polylysine YSi SPA beads and membrane were determined. The assay free radioligand concentration was expressed as a percentage of the total free radioligand concentration to give an estimate of the radioligand depletion. The radioligand depletion in the assay was less than 10% to ensure that there was sufficient radioligand available for binding.

The affinity of $^3$H-meselurgine for the human recombinant 5-HT$_{2C}$ receptor was determined for each membrane batch at the selected protein and bead concentrations. This was achieved by the determination of the $K_D$, the concentration of free radioligand at which 50% of the receptor binding sites were occupied. The mean $K_D$ for $^3$H-meselurgine at a batch of membranes was determined from data from a minimum of three separate assays. The mean $K_D$ was subsequently used for all assays using the membrane batch profiled to enable determination of $K_i$ values of compounds studied using the method determined by Cheng and Prussoff (Cheng Y C and Prusoff W H. Relationship between the inhibition constant ($K_i$) and the concentration of inhibitor which causes 50% inhibition of an enzymatic reaction. Biochem Pharmacol 1973; 22:2099-3108.)

Assay Protocol

Bead/Receptor Membrane Complex Preparation

The required amount of membrane, was thawed on ice and added to a pre-determined volume of bead suspension in 50 mM HEPES buffer, pH 7.4. The beads were then pre-coupled by incubating the predetermined protein quantity per mg of bead on a roller 4° C. for 1 h. Subsequently, the bead/membrane complex was spun down at 1000 rpm for 5 min. The resulting pellet was resuspended in assay buffer at the specific concentration required for the final assay.

Ligand Preparation

An aliquot of [$^3$H]-meselurgine stock was diluted in binding assay buffer to give a pre-determined final assay concentration less than the equilibrium dissociation constant ($K_D$) value.

Compound Plate Preparation

All test compounds were prepared at a concentration of 4 mM in 100% dimethyl sulphoxide (DMSO) from dry samples. Compounds were diluted in 2.5% DMSO in Dulbeccos PBS with 0.05% Pluronic F-127 to give appropriate test concentrations in a 384 well plate to give a final volume of 5 μL.

The same volume of assay buffer was added to specific wells of the plate to enable subsequent measurement of total radioligand binding. Furthermore, 5 μL of Mianserin at 25 μM (2.5 μM final assay concentration was subsequently added to pre-determined wells to determine non-specific binding (NSB).

For the assay, 20 μL of the corresponding bead/membrane complex was added to each well of the final assay plate, ensuring that the suspension was mixed well. 25 μL of $^3$H-meselurgine was added to each well of the final assay plates (containing compound solutions). Subsequently, 25 μL of $^3$H-meselurgine was added to each well of the final assay plates (containing compound solutions). The plates were then sealed and incubated, with shaking, for 2 h 30 min at room temperature. The plates were subsequently left to settle for 10 min with dark adaptation, prior to reading.

Data Analysis

The assay window (specific binding) per plate was calculated by subtracting the mean NSB readings (in counts per minute, or cpm) from the mean of total binding readings. Subsequently the cpm read per well (with mean NSB subtracted) were expressed as a percentage of the plate window to determine the amount of radioligand bound to the receptor-bead complex.

These values were plotted against the concentration of the compound tested and a sigmoidal inhibitory concentration effect curve was fitted to the data using a four-parameter logisitic equation and free-fitting parameters to give an IC$_{50}$ value (the concentration of compound required to inhibit 50% of the specific binding at the 5-HT$_{2C}$ receptor).

The inhibitory dissociation constant ($K_i$) value was then calculated from the IC$_{50}$ value using the Cheng-Prusoff equation.

Following determination of individual $K_i$ values for compounds tested, an overall geometric mean was calculated together with 95% confidence intervals and n values, where n is the total number of individual $K_i$ values.

Buffers

Membrane Preparation Buffer 50 mM HEPES, pH 7.4 at room temperature, stored at 4° C. Prior to use, one complete protease inhibitor tablet was dissolved per 50 mL of buffer.

Binding Assay Buffer 50 mM HEPES pH 7.4

10 mM CaCl$_2$ 0.1 mM Pargyline 0.1% Ascorbic Acid 0.05% Pluronic

Sexual Dysfunction

FSAD Method

Female New Zealand rabbits (~2.5 kg) are pre-medicated with a combination of Medetomidine (Domitor®) 0.5 mL/kg intramuscularly (i.m.), and Ketamine (Vetalar®) 0.25 mL/kg i.m. while maintaining oxygen intake via a face mask. The rabbits are tracheotomised using a Portex™ uncuffed endotracheal tube 3 ID (internal diameter), connected to ventilator and maintained at a ventilation rate of 30-40 breaths per minute, with an approximate tidal volume of 18-20 mL, and a maximum airway pressure of 10 cm H$_2$O. Anaesthesia is then switched to Isoflurane® and ventilation continued with O$_2$ at 2 l/min. The right marginal ear vein is cannulated using a 23 G or 24 G catheter, and Lactated Ringer solution perfused at 0.5 mL/min. The rabbit is maintained at 3% Isoflurane® during invasive surgery, dropping to 2% for maintenance anaesthesia.

The left groin area of the rabbit is shaved and a vertical incision is made approximately 5 cm in length along the thigh. The femoral vein and artery are exposed, isolated and then cannulated with a PVC catheter (17 G) for the infusion of drugs and compounds. Cannulation is repeated for the femoral artery, inserting the catheter to a depth of 10 cm to ensure that the catheter has reached the abdominal aorta. This arterial catheter is linked to a Gould system to record blood pressure. Samples for blood gas analysis are also taken via the arterial catheter. Systolic and diastolic pressures are measured, and the mean arterial pressure calculated using the formula (diastolic×2+systolic)÷3. Heart rate is measured via the pulse oxymeter and Po-ne-mah data acquisition software system (Ponemah Physiology Platform, Gould Instrument Systems Inc).

A ventral midline incision is made into the abdominal cavity. The incision is about 5 cm in length just above the pubis. The fat and muscle is bluntly dissected away to reveal the hypogastric nerve which runs down the body cavity. It is essential to keep close to the side curve of the pubis wall in order to avoid damaging the femoral vein and artery, which lie above the pubis. The sciatic and pelvic nerves lie deeper and are located after further dissection on the dorsal side of the rabbit. Once the sciatic nerve is identified, the pelvic nerve is easily located. The term pelvic nerve is loosely applied; anatomy books on the subject fail to identify the nerves in sufficient detail. However, stimulation of the nerve causes an increase in vaginal and clitoral blood flow, and innervation of the pelvic region. The pelvic nerve is freed away from surrounding tissue and a Harvard bipolar stimulating electrode is placed around the nerve. The nerve is slightly lifted to give some tension, then the electrode is secured in position. Approximately 1 mL of light paraffin oil is placed around the nerve and electrode. This acts as a protective lubricant to the nerve and prevents blood contamination of the electrode. The electrode is connected to a Grass S88 Stimulator. The pelvic nerve is stimulated using the following parameters: −5V pulse width 0.5 ms, duration of stimulus 10 s and a frequency range of 2 to 16 Hz. Reproducible responses are obtained when the nerve is stimulated every 15-20 min. A frequency response curve is determined at the start of each experiment in order to determine the optimum frequency to use as a submaximal response, normally 4 Hz. A ventral midline incision is made, at the caudal end of the pubis, to expose the pubic area. Connective tissue is removed to expose the tunica of the clitoris, ensuring that the wall is free from small blood vessels. The external vaginal wall is also exposed by removing any connective tissue. One laser Doppler flow probe is inserted 3 cm into the vagina, so that half the probe shaft is still visible. A second probe is positioned so that it lay just above the external clitoral wall. The position of these probes is then adjusted until a signal is obtained. A second probe is placed just above the surface of a blood vessel on the external vaginal wall. Both probes are clamped in position.

Vaginal and clitoral blood flow is recorded either as numbers directly from the Flowmeter using Po-ne-mah data acquisition software (Ponemah Physiology Platform, Gould Instrument Systems Inc), or indirectly from Gould chart recorder trace. Calibration is set at the beginning of the experiment (0-125 mL/min/100 g tissue). All data are reported as mean±standard error of the mean (s.e.m.). Significant changes are identified using Student's t-tests.

MED Method

The antidepressant trazodone and its non-selective 5-HT$_2$ agonist metabolite, m-CPP, are associated with proerectile activity in man. Studies have shown that m-CPP, a non selective 5-HT$_2$ receptor agonist and the selective 5-HT$_2$ agonist, Ro-60-0175 enhance penile erection in conscious rats and monkeys following i.v., i.p., s.c. or i.m. administration. These responses are blocked by 5-HT$_{2B/2C}$ antagonists but not by 5-HT$_{2B}$ or 5-HT$_{2A}$ antagonists. Further data from Nortran Pharmaceuticals demonstrates that centrally-acting non selective 5-HT$_{2C}$ agonists (e.g. RSD992) induced erection and facilitated male copulatory behaviour in rodents and primates, with little effect in the absence of a female. Therefore, it is reasonable to believe that the compounds of formula (I) would be useful for treatment of male erectile dysfunction.

The compounds of formula (I) may be screened for effect of penile intracavernosal pressure (ICP) in the conscious male rat according to the methods described hereinbelow.

ICP Protocol: Intra cavernosal pressure (ICP) can be measured in the conscious rat by means of telemetric recording. A catheter is surgically implanted into the corpus cavernosum. The end of the catheter is linked to a device, which senses, processes, and transmits information digitally from within the animal. A receiver converts the radio-frequency signal from the implant to a digital pulse stream that is readable by a data collection system. The PC-based system collects telemetred data from the animal.

Surgery: Induce and maintain general anaesthesia using 5% Isoflurane® in a carrier gas of 0.5 liter/minute oxygen and 1 liter/minute nitrous oxide to induce anaesthesia, reducing to 2% Isoflurane for maintenance anaesthesia. Administer 5 mg/kg sub cutaneously (s.c.) Carprofen (Rimadyl® Large Animal Injection, 50 mg/mL, Pfizer Animal Health) at induction of anaesthesia, at end of day of surgery and on the morning of first day post-surgery to minimize pain and discomfort.

Implantation of corpus cavernosal probe: Shave the skin of the ventral abdomen and extend to include the area around the penis and ventral scrotum. Clean and disinfect the shaved area. Place the rat in dorsal recumbency. Make a mid-line incision from the external base of the penis, running caudally for approximately 2 cm. Locate and expose the internal structure of the penis and identify the corpus cavernosum. Make a mid-line laparotomy, approximately 4 cm in length to access the abdominal cavity. Pierce the abdominal wall via the caudal incision with a suitable trocar and cannula, taking care not to damage any internal organs. Place the implant body in the abdominal cavity with the catheter orientated caudally and pass the catheter tip through the body wall via the preplaced cannula. A model TA11PA-C40, 8 mm catheter implant may be used with a modified 3 mm tip (Data Sciences International Inc.). Secure the implant body to the abdominal wall using non-absorbable sutures and partially close the abdominal incision. Reflect the tip of the penis cranially and retract the caudal incision to optimize the surgical field. Carefully isolate approximately 10 mm of the internal structure of the penis from the surrounding tissue. Carefully reflect the corpus spongiosum to one side to give access to the corpus cavernosum. Access the corpus cavernosum using a modified over-the-needle catheter to puncture the tunica. Introduce the catheter tip via the preplaced catheter and advance until fully inserted. Carefully remove the access catheter and apply a suitable tissue adhesive to the insertion site. Observe for leakage. Close the subcutaneous fat layer in the caudal incision before closing with an appropriate absorbable suture. Instil approximately 5 mL of warm saline through the abdominal incision and complete closure of the mid-line incision. Close the skin incision with an appropriate absorbable suture.

Postoperative care: Measure food and water intake and monitor bodyweight daily for at least 7 days post surgery, then 2-3 times weekly. Give Lectade® (Pfizer Animal Health) in drinking water for 3 days post surgery. House rats singly, and transfer to reverse light/dark conditions 5 days post surgery. Named Veterinary Surgeon (or Deputy) to issue a certificate of fitness to continue 2 days post surgery. Start using rats experimentally 7 days post surgery.

Experimental Procedure: Perform experiment in room with reverse light/dark conditions. On day of experiment, place rat in home cage on receiver pad (PhysioTel® Model RPC-1, Data Sciences International Inc.) and leave to acclimatize for approximately one hour. Ensure that the rat has food and water ad lib. Take baseline reading of intra cavernosal pressure (ICP) for approximately 5 minutes. Transfer the data via a floppy disk to an Excel spreadsheet. Inject the rat with compound subcutaneously or via the jugular vein catheter (JVC). If using the JVC, flush through with sterile saline after dosing and seal with a saline/glucose lock solution. The interval between administration of compound and ICP measurement will vary with the compound to be tested. An interval of 30-60 min post s.c. injection is a good guide. The test compounds are dissolved in 50% β-cyclodextrin in saline. They are administered at a dose of 5-10 mg/kg subcutaneously (s.c.). Apomorphine hydrochloride hemihydrate (Sigma™ A-4393) at 60 μg/kg s.c. is used as a positive control as it has pro-erectile properties. Record ICP over a 15 min period, starting at 30 min post injection i.e. from 30 to 35 minutes and repeat for two further 15 min periods commencing at 60 min post injection and 120 minutes post injection respectively. Record ICP for 15 min: A signal from the receiver pad feeds through to the Data Exchange Matrix® and hence to the software (Dataquest ART® acquisition system, Data Sciences International Inc.). Transfer the data via a floppy disk to an Excel spreadsheet for analysis.

Combination with PDE51 for Treatment of MED

The effects of concomitant administration of a compound of formula (I) in combination with a PDE5 inhibitor on the penile intracavernosal pressure (ICP) in an anaesthetised rabbit model of erection can be measured according to the following protocol.

Experimental Protocol

Male New Zealand rabbits (~2.5kg) are pre-medicated with a combination of Medetomidine (Domitor®) 0.5 mL/kg inramuscularly (i.m.), and Ketamine (Vetalar®) 0.25 mL/kg i.m. whilst maintaining oxygen intake via a face mask. The rabbits are tracheotomised using a Portex™ uncuffed endotracheal tube 3 ID (internal diameter), connected to ventilator and maintained at a ventilation rate of 30-40 breaths per minute, with an approximate tidal volume of 18-20 mL, and a maximum airway pressure of 10 cm $H_2O$. Anaesthesia is then switched to Isoflurane® and ventilation continued with $O_2$ at 2 litres/min. The right marginal ear vein is cannulated using a 23 G or 24 G catheter, and Lactated Ringer solution perfused at 0.5 mL/min. The rabbit is maintained at 3% Isoflurane during invasive surgery, dropping to 2% for maintenance anaesthesia. The left jugular vein is exposed, isolated and then cannulated with a PVC catheter (17 gauge/17 G) for the infusion of drugs and the test compounds.

The left groin area of the rabbit is shaved and a vertical incision is made approximately 5 cm in length along the thigh. The femoral vein and artery are exposed, isolated and then cannulated with a polyvinylchloride (PVC) catheter (17 G) for the infusion of drugs and compounds. Cannulation is repeated for the femoral artery, inserting the catheter to a depth of 10 cm to ensure that the catheter reaches the abdominal aorta. This arterial catheter is linked to a Gould system to record blood pressure. Samples for blood gas analysis are also taken via the arterial catheter. Systolic and diastolic pressures are measured, and the mean arterial pressure calculated using the formula (diastolic×2+systolic)÷3. Heart rate is measured via the pulse oxymeter and a Po-ne-mah data acquisition software system (Ponemah Physiology Platform, Gould Instrument Systems Inc).

A ventral midline incision is made into the abdominal cavity. The incision is about 5 cm in length just above the pubis. The fat and muscle is bluntly dissected away to reveal the hypogastric nerve which runs down the body cavity. It is essential to keep close to the side curve of the pubis wall in order to avoid damaging the femoral vein and artery which lie above the pubis. The sciatic and pelvic nerves lie deeper and are located after further dissection on the dorsal side of the rabbit. Once the sciatic nerve is identified, the pelvic nerve is easily located. The term pelvic nerve is loosely applied; anatomy books on the subject fail to identify the nerves in sufficient detail. However, stimulation of the nerve causes an increase in intracavernosal pressure and cavernosal blood flow, and innervation of the pelvic region. The pelvic nerve is freed away from surrounding tissue and a Harvard bipolar stimulating electrode is placed around the nerve. The nerve is slightly lifted to give some tension, then the electrode is secured in position. Approximately 1 mL of light paraffin oil is placed around the nerve and electrode. This acts as a protective lubricant to the nerve and prevents blood contamination of the electrode. The electrode is connected to a Grass S88 Stimulator. The pelvic nerve is stimulated using the following parameters: −5V, pulse width 0.5 ms, duration of stimulus 20 s with a frequency of 16 Hz. Reproducible responses are obtained when the nerve is stimulated every 15-20 min. Several stimulations using the above parameters are performed to establish a mean control response. The compounds to be tested are infused, via the jugular vein, using a Harvard 22 infusion pump allowing a continuous 15 min stimulation cycle. The skin and connective tissue around the penis is removed to expose the penis. A catheter set (Insyte-W, Becton-Dickinson 20 Gauge 1.1×48 mm) is inserted through the tunica albica into the left corpus cavernosal space and the needle removed, leaving a flexible catheter. This catheter is linked via a pressure transducer (Ohmeda 5299-04) to a Gould system to record intracavernosal pressure (ICP). Once an intracavernosal pressure is established, the catheter is sealed in place using Vetbond (tissue adhesive, 3M). Heart rate is measured via the pulse oxymeter and a Po-ne-mah data acquisition software system (Ponemah Physiology Platform, Gould Instrument Systems Inc).

Intracavernosal blood flow is recorded either as numbers directly from the Flowmeter using Po-ne-mah data acquisition software (Ponemah Physiology Platform, Gould Instrument Systems Inc), or indirectly from Gould chart recorder trace. Calibration is set at the beginning of the experiment (0-125 mL/min/100 g tissue).

All data is reported as mean±s.e.m. (standard error of the mean). Significant changes are identified using Student's t-tests. The test compounds are dissolved in 50% β-cyclodextrin in saline. They are administered at a dose of 5-10 mg/kg subcutaneously (s.c.).

Obesity and Related Disorders

The practice of the present invention for treating obesity or related eating disorders (including promoting weight loss or reducing weight gain) can be evidenced by activity in one or both of the protocols described hereinbelow.

Spontaneous Food Intake

Male Sprague-Dawley rats may be obtained from Charles River Laboratories, Inc. (Wilmington, Mass.). The rats are individually housed and fed powdered chow. They are maintained on a 12 h light/dark cycle and receive food and water ad libitum. The animals are acclimated to the vivarium for a period of one week before, testing is conducted. Rats are transferred to individual test cages 30 h before the study. The rats are administered test compound or vehicle alone (no compound) 15-30 min prior to the onset of the dark cycle. The test compounds are dosed at ranges between 0.1 and 100 mg/kg depending upon the compound. The standard vehicle is 0.5% (w/v) methylcellulose or 30% β-cyclodextrin in water and the standard route of administration is oral. However, different vehicles and routes of administration are used to accommodate various compounds when required.

Food intake is monitored using an automated Columbus Instruments system (Columbus, OH). Individual rat food intake is recorded continuously at 10 min intervals, starting at the time of dosing, for a period of at least 12 h. Compound efficacy is determined by comparing the food intake pattern of compound-treated rats to vehicle.

Oxygen Consumption

Whole body oxygen consumption is measured using an indirect calorimeter (Oxymax from Columbus Instruments, Columbus, OH) in male Sprague Dawley rats (if another rat strain or female rats is used, it will be specified). Rats (300-380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 min for 2.5 to 3 h. At the end of the basal pre-dosing period, the chambers are opened and the animals are administered a single dose of compound (the usual dose range is 0.001 to 10 mg/kg) by oral gavage (or other route of administration as specified, i.e. s.c., i.p., i.v.). Drugs are prepared in methylcellulose, water or other specified vehicle (examples include PEG400, 30% beta-cyclo dextran and propylene glycol). Oxygen consumption and ambulatory activity are measured every 10 min for an additional 1-6 h post-dosing.

The Oxymax calorimeter software calculates the oxygen consumption (mL/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre- and post-dosing, is calculated by averaging the 10-min $O_2$ consumption values, excluding periods of high ambulatory activity (ambulatory activity count>100) and excluding the first 5 values of the pre-dose period and the first value from the post-dose period. Change in oxygen consumption is reported as percent and is calculated by dividing the post-dosing resting oxygen consumption by the pre-dose oxygen consumption×100. Experiments will typically be done with n=4-6 rats and results reported are mean±SEM.

An increase in oxygen consumption of >10% is considered a positive result. Historically, vehicle-treated rats have no change in oxygen consumption from pre-dose basal.

Schizophrenia and Related Disorders

The practice of the present invention for treating schizophrenia and related disorders can be evidenced by activity in the protocol described hereinbelow. For example, the compounds of formula (I) may be assessed in a number of standard behavioral tests predictive of antipsychotic activity. For example, apomorphine-induced climbing behavior and hypothermia in mice (see, e.g., Moore, N. A. et al. *Psychopharmacology* 94 (2), 263-266 (1988), and 96, 539 (1988)). Conditioned Avoidance Responding (inhibition of CAR) has been a classic and effective test used for the detection of drugs with potential antipsychotic activity, primarily developed to test neuroleptics acting through dopamine receptor blockade). Similarly, d-Amphetamine locomotor (antagonism of the increased activity produced by d-amphetamine to show dopamine receptor blockade) and PCP locomotor (antagonism of the increased activity produced by the activation of dopamine neuronal function by the non-competitive N-methyl-D-aspartate (NMDA) receptor antagonist; phencyclidine (PCP)) assays can be used to predict anti-psychotic activity.

Locomotor Activity

The locomotor activity boxes consist of 48 individual plexiglass behavioral chambers (30 cm×30 cm) enclosed in sound attenuating cabinets. A single 10 watt bulb in each cabinet is controlled by a 24 h timer, which allows the behavioral to be maintained on any light/dark cycle desired. The plexiglass chambers are fitted with grid floors which are divided into quadrants and a metal touchplate positioned 7 cm from the floor on all four walls of the chamber. Horizontal locomotor activity is measured as the number of cross-avers an animal makes from one quadrant to another within its chamber. When the animal stands up (rears) and makes contact with the metal touchplate it is recorded by the computer as vertical locomotor activity. Subjects are placed in the chambers overnight (approx. 15 h) prior to the experiment. The next day each animal is weighed and treated with the test compound and then immediately returned to the test chamber. At a set pretreatment time, subjects are removed from the test chamber and treated with phencyclidine hydrochloride (3.2 mg/kg, s.c.), or d-Amphetamine sulphate (1 mg/kg, s.c.) and then immediately returned to the test chamber. Horizontal movements (cross-overs) are recorded by a computer for a three-hour test period.

In order to measure spontaneous locomotor activity, each animal is weighed and treated with the test compound one hour prior to being placed in the activity box. The test is always started as soon after the dark cycle (4 pm) as possible so that the effects of the compound can be observed during the animals' most active time. The apparatus is programmed to collect data overnight for a 12 h period.

The computer is programmed to perform statistical analysis at given intervals. A one-way ANOVA is used to determine whether a difference due to treatment exists and is followed by Dunnett's multiple range test to determine differences between the control and experimental groups. Timed intervals of data (cross-avers) are analyzed individually and cumulatively for the duration of the experiment.

Conditioned Avoidance Response

Male CF rats (Charles River, Fisher-344 strain) are used in all experiments. Weights are approximately 350-400 g at the time of testing. Animals are housed 2 per cage in environmentally controlled animal quarters (light/dark-4 am/4 pm). The conditioned avoidance shuttle chambers consist of 8 individual Plexiglas behavior chambers (Coulbourn Instruments™) each divided by a guillotine door into two sides, enclosed in sound attenuating cabinets. The Plexiglas chambers are fitted with metal grid floors, which are equipped with scrambled/constant current shockers.

Rats are trained to avoid the onset of footshock (1.5 mA, preceded for 5 s by activation of house lights, que lights, and the opening of the guillotine door) by moving to the opposite side of the chamber. Thirty trials are completed per daily session, and the number of avoidance's (max 30), escapes (max 30), escape failures (max 30), latency to avoid (max 5 s.), latency to escape (max. 10 s.), and adaptation crossovers (number of crossovers for a 5 min period before the onset of trials, dark chamber) are recorded by the computer program. Inter-trial intervals are 15 s with the guillotine door closed. Drug treatment begins (30 min prior to session, s.c.) when rats have reached criteria of 80% avoidances for a session. Testing is performed during the lights on period of the light/dark cycle, typically between 8 am and 10 am.

Vehicle treatment is performed one day every week and statistical analysis is done comparing each drug treatment on separate days vs. the vehicle treatment that week. Testing is performed during the lights on period of the light/dark cycle, typically between 8 am and 10 am. The data is analyzed following importation into a spreadsheet using a t-test.

Anxiety and Related Disorders

Activity of compounds of the present invention for the treatment of anxiety and related disorders can be demonstrated in models using well-established procedures. For example, the following model may be used.

Acute Stress-Related Cerebellar cGMP Assay

Acute Stress Procedure: CF-1 mice (Charles River Laboratories) weighing 19-22 g are ordered one week prior to testing and are handled for two days before the experiment to reduce stress-related changes in basal cGMP levels. Animals are housed on a 12 hr light:dark schedule (6 a-6 p) in a temperature and humidity controlled room with free access to food and water.

After dosing (typically 30-60 min depending on drug), animals to be stressed are placed into a Coulbourn chamber with a steel grid floor and shocked at 1 mA for 10 seconds. Immediately following the stressor mice are placed into a plastic restraint tube and sacrificed using a beam of microwave irradiation focused on the head (2.0 kW for 0.9 sec) using a Gerling-Moore Metabostat. The cerebellum is then rapidly removed, snap frozen in liquid nitrogen, and stored at −80 C prior to the cGMP assay. Non-stressed animals are taken directly from their home cages, sacrificed by microwave irradiation and processed the same.

cGMP Assay: Whole cerebella are weighed and then homogenized in 1 ml of 1% perchloric acid in dd-water using a Brinkman Polytron at 15,000 rpm for about 15 sec each and placed on ice until all samples are homogenized.

Samples are then placed into an 85 C water bath for 5 min, centrifuged at 2500×g for 15 min at 4 C, and about 0.5 ml of the supernatant is collected for analysis.

Supernatants are diluted 1:5 in 0.05M sodium acetate buffer (pH 5.8). All other assay steps proceed according to the directions of the manufacturer of the cGMP EIA kits (Amersham Biosciences). Diluted samples are incubated overnight in treated 96-well plates and processed the following day. Samples are read at 450 nm optical wavelength and converted to pmol cGMP/mg tissue using a standard curve generated in the same experiment.

Lower Urinary Tract Symptoms

Known $5-HT_{2c}$ agonists (e.g., m-CPP, Ro 60-0175, YM348) have shown doses related increases in bladder capacity and urethral EMG activity in the anaesthetized guinea-pg cystometry and urethral EMG models. These effects were dose dependently abolished by a selective $5-HT_{2c}$ antagonist. In the anaesthetized dog urethral pressure model, which has been validated for stress urinary incontinence (SUI) with duloxetine, the $5-HT_{2c}$ agonist Ro60-0175 increased urethral pressure in a dose-dependent manner, with at least similar efficacy to duloxetine. Hence, it is reasonable to believe that the compounds of formula (I) would be useful for the treatment of conditions involving lower urinary tract dysfunction.

Activity of the compounds of formula (I) for lower urinary tract function, and thus their potential usefulness in treating conditions involving lower urinary tract dysfunction, can be investigated and assessed utilizing a number of standard in vivo models known to those skilled in the art and frequently described in the literature (Morrison, J., et al., Neurophysiology and Neuropharmacology. In: Incontinence, Ed. Abrams, P., Cardozo, C., Khoury, S. and Wein, A. Report of the World Health Organisation Consensus Conference. Paris, France: Health Publications Ltd., 2002: 83-163; Brune M E et al. Comparison of alpha 1-adrenoceptor agonists in canine urethral pressure profilometry and abdominal leak point pressure models. J Urol. 2001, 166:1555-9). As an example the compounds of formula (I) can be tested for such effects in the models described herein below.

Investigation of Bladder Capacity and External Urethral Sphincter (EUS) Function in the Guinea-Pig Experiments are performed in adult female guinea pigs, weighing approx 500 g. All animals are initially anaesthetised with halothane (4%), carried in oxygen (3-4 L min$^{-1}$) and maintained at an appropriate surgical plane with urethane (25% w/v; 0.5 mL 100 g$^{-1}$ body weight). The trachea, a jugular vein and a carotid artery are cannulated for respiratory ventilation, injection of test compound and monitoring of blood pressure, respectively. A midline laporatomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilization period, the bladder is filled at a rate of 150 μl min$^{-1}$ with physiological saline (room temperature), until initiation of a micturition reflex is observed. Following micturition, the bladder is drained via the externalised cystometry tube. Bladder filling is then repeated at least 3 times (or until repeatable filling cycles are achieved) in order to establish a mean bladder threshold capacity for initiation of micturition. EUS EMG activity and intravesical (bladder) pressure are recorded throughout bladder filling. Subsequently, test compound or vehicle is injected intravenously utilizing either a bolus dose or constant infusion and bladder filling re-initiated (150 μl min$^{-1}$) until micturition occurs, the bladder is then drained as before and the process repeated with addition of increasing doses of test compound (2 micturition responses are measured at each compound concentration). Changes in threshold bladder capacity initiating micturition and/or in EUS EMG activity are indicative of compound activity on lower urinary tract function.

Investigation of Abdominal Leak Point Pressure in the Guinea-Pig

Experiments are performed in adult female guinea pigs, weighing approx 500 g. All animals are initially anaesthetized with halothane (4%), carried in oxygen (3-4 L min$^{-1}$) and maintained at an appropriate surgical plane with urethane (25% w/v; 0.5 mL 100 g$^{-1}$ body weight). The trachea, a jugular vein and a carotid artery are cannulated for respiratory ventilation, injection of test compound and monitoring of blood pressure, respectively. A midline laporatomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilization period, the bladder is filled at a rate of 150 μl min$^{-1}$ with physiological saline (room temperature), until initiation of a micturition reflex is observed. Following micturition, the bladder is drained via the externalized cystometry tube. Bladder filling is then repeated at least 3 times (or until repeatable filling cycles are achieved) in order to establish a mean bladder threshold capacity for initiation of micturition. EUS EMG activity and intravesical (bladder) pressure are recorded throughout bladder filling. Subsequently, the bladder is filled (150 µl min$^{-1}$) to 75% of this threshold volume with physiological saline and, through the use of a specially constructed frame, increasing weight is applied to the ventral surface of the abdomen of the animal just rostral to the position of the bladder until leakage of fluid is observed at the urethral meatus. This process is repeated at least 3 times in order to establish control responses; EUS EMG activity and intravesical pressure being recorded throughout. Subsequently increasing concentrations of test compound or vehicle is injected intravenously utilizing either a bolus dose or constant infusion and weight induced leak responses re-investigated at each concentration. Changes in the abdominal weight required to induce leak and/or the maximum EUS EMG activity recorded immediately prior to leak are indicative of compound activity on lower urinary tract function.

Investigation of Guinea-Pig Urethral Pressure Profilometry:

Experiments are performed in adult female guinea pigs, weighing approx 500 g. All animals are initially anaesthetized with halothane (4%), carried in oxygen (3-4 L min$^{-1}$) and maintained at an appropriate surgical plane with urethane (25% w/v; 0.5 mL 100 g$^{-1}$ body weight). The trachea, a jugular vein and a carotid artery are cannulated for respiratory ventilation, injection of test compound and monitoring of blood pressure, respectively. A midline laporatomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilization period, the bladder is filled at a rate of 150 µl min$^{-1}$ with physiological saline (room temperature), until initiation of a micturition reflex is observed. Following micturition, the bladder is drained via the externalized cystometry tube. Bladder filling is then repeated at least 3 times (or until repeatable filling cycles are achieved) in order to establish a mean bladder threshold capacity for initiation of micturition. Subsequently, the bladder is filled (150 µl min$^{-1}$) to 75% of this threshold volume and urethral tone (peak urethral pressure (PUP), functional urethral length (FUL) and closing pressure (CP)) assessed with the aid of a 3F Millar pressure transducer (Millar Instruments, Texas, US) inserted into the bladder through the external meatus. The urethral Millar pressure transducer is then retracted along the length of the urethra (urethral pull through) at a rate of 1 cm/min enabling the determination of PUP, FUL and CP. Urethral pull throughs are repeated every 2 min until 4 reproducible urethral profiles are observed. Subsequently increasing concentrations of test compound or vehicle is injected intravenously utilising either a bolus dose or constant infusion and a further 4 urethral pull throughs carried out at each concentration investigated. Changes in the PUP, FUL, CP or EUS EMG activity are indicative of compound activity on lower urinary tract function.

Investigation of Dog Urethral Pressure Profilometry

Female beagle dogs (10-15 kg) are anaesthetized with sodium pentobarbitone (60 mg/mL solution) administered intravenously (IV) at 0.5 mL/kg via the right cephalic vein. Immediately following induction of anaesthesia the dog is intubated and respiration supported by artificial ventilation with oxygen. End tidal $CO_2$ is monitored continuously, using a Datex $CO_2/O_2$ monitor and maintained between 4.5 and 4.8% and body temperature maintained between 37° C. and 38° C. An incision is made in the right medial thigh and a polyethylene catheter (6F) inserted into the right femoral vein for administration of compounds and fluid maintenance; immediately venous access is achieved a bolus IV dose of α-chloralose (1% w/v) is administered at 35 mg/kg. A polyethylene catheter (4F) is inserted into the right femoral artery for blood sampling. An incision is made in the right foreleg and the brachial vein and artery isolated, maintenance of anaesthesia is achieved with α-chloralose/borax administered IV at the rate of 10 mg/kg/h via a polyethylene catheter (6F) inserted into the right brachial vein. A laparotomy is performed from the umbilicus to the top of the pubic symphysis via the midline to expose the peritoneum in order to expose the bladder. Both ureters are cannulated towards the kidneys with polyethylene catheters (6F) and urine collected externally; the bladder is catheterized through the dome with a polyethylene catheter (6F), which is in turn connected to a pressure transducer. In order to maintain constant bladder pressure at 10-15 mmHg, urine is removed and ambient temperature saline infused into the bladder. Immediately following the completion of the surgical procedures a further bolus dose of α-chloralose/borax solution is administered IV at 35 mg/kg and the animal allowed to stabilise for a period period ca. 1 h, during which time haemodynamic and urological parameters were monitored.

Urethral tone (peak urethral pressure (PUP), functional urethral length (FUL) and closing pressure (CP)) is assessed with the aid of an 8F Millar pressure transducer (Millar Instruments, Texas, US) inserted into the bladder through the external meatus. The urethral Millar pressure transducer is then retracted along the length of the urethra (urethral pull through) at a rate of 1 cm/min enabling the determination of PUP, FUL and CP. Urethral pull throughs are repeated every 6 min until 4 reproducible urethral profiles are observed. Subsequently increasing concentrations of test compound or vehicle is injected intravenously utilising either a bolus dose or constant infusion and a further 4 urethral pull throughs carried out at each concentration investigated. Changes in the PUP, FUL or CP are indicative of compound activity on lower urinary tract function.

Investigation of Bladder Capacity and External Urethral Sphincter (EUS) Function in the Spontaneously Hypertensive Rat Experiments are performed in adult female spontaneously hypertensive rats (SHRs), weighing approx 250-300 g. All animals are initially anaesthetized with isoflurane (4%), carried in oxygen (3-4 L min$^{-1}$) and maintained at an appropriate surgical plane with urethane (25% w/v; 0.5 mL 100 g$^{-1}$ body weight). The trachea, a jugular vein and a carotid artery are cannulated for respiratory ventilation, injection of test compound and monitoring of blood pressure, respectively. A midline laporatomy is performed to expose the urinary bladder and a cystometry tube inserted through a small incision in the dome of the bladder and secured in place. The abdominal wound is then closed tightly around the externalised cystometry tube, which, in turn, is connected to an infusion pump and pressure transducer, for filling the bladder and recording intravesical pressure, respectively. Electromyographic (EMG) wire leads are inserted into the EUS striated muscle layer opposed to the dorsal surface of the symphysis pubis. The EMG leads are connected to an appropriate amplification and electrical filter system and changes in EUS electrical activity displayed on an oscilloscope and recorded through appropriate computer software.

Following a 30 min post surgery stabilization period, the bladder is filled at a rate of between 45 and 100 μl $min^{-1}$ with physiological saline (room temperature), until initiation of a micturition reflex is observed. Following micturition, the bladder is drained via the externalized cystometry tube. Bladder filling is then repeated at least 3 times (or until repeatable filling cycles are achieved) in order to establish a mean bladder threshold capacity for initiation of micturition. EUS EMG activity and intravesical (bladder) pressure are recorded throughout bladder filling. Subsequently, test compound or vehicle is injected intravenously utilizing either a bolus dose or constant infusion and bladder filling re-initiated until micturition occurs, the bladder is then drained as before and the process repeated with addition of increasing doses of test compound (2 micturition responses are measured at each compound concentration). Changes in threshold bladder capacity initiating micturition and/or in EUS EMG activity are indicative of compound activity on lower urinary tract function.

Investigation of Voided Volume in Conscious Ovariectomised Mice

Ovariectomised adult female mice are dosed (either orally or sub-cutaneously) with vehicle or increasing concentrations of compound and placed in individual metaboles with free access to water for 3 h. Urine voided by each mouse is captured on a conical sponge within a container placed beneath each metabole, this sponge also deflects faecal pellets. The total volume of urine voided within the 3 h period and the volume of urine per void is measured by a balance placed directly beneath the collection container. The average volume of urine per void and the frequency of voiding events are compared between vehicle and compound treated groups (up to n=16 per group), changes in these parameters in the absence of changes in the total urine output are indicative of compound activity on lower urinary tract function.

Investigation of Voided Volume and Bladder Activity in Conscious Telemeterized Spontaneously Hypertensive Rats Adult female spontaneously hypertensive rats are dosed (either orally or sub-cutaneously) with vehicle or increasing concentrations of compound and placed in individual metaboles with free access to water for 3 h. Urine voided by each rat is captured on a conical sponge within a container placed beneath each metabole, this sponge also deflects faecal pellets. The total volume of urine voided within the 3 h period and the volume of urine per void is measured by a balance placed directly beneath the collection container. The average volume of urine per void and the frequency of voiding events are compared between vehicle and compound treated groups (up to n=16 per group), changes in these parameters in the absence of changes in the total urine output are indicative of compound activity on lower urinary tract function.

Other aspects of the invention are enumerated in the claims.

Biological Data

Biological activity of the compounds of the invention is illustrated in the table below. Preferred compounds of the invention exhibit an efficacy ($E_{max}$) of greater than 30% and an agonist activity (EC50) of less than 1 μM. Particularly preferred compounds of the invention exhibit an efficacy ($E_{max}$) of greater than 30%, and an agonist activity (EC50) of less than 500 nM.

| Example No. | Structure | Emax % | EC50 (nM) | Binding Affinity Ki (nM) |
|---|---|---|---|---|
| 1 | 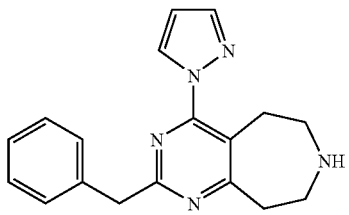 | 83.50 | 224 | 72.0 |
| 2 | 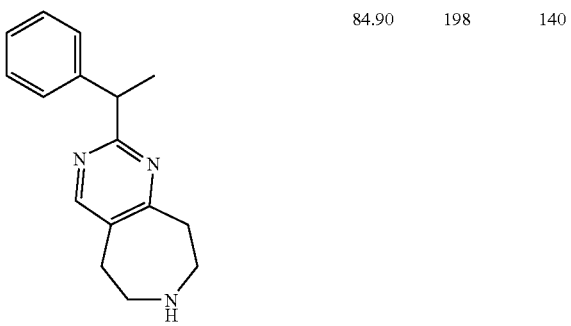 | 84.90 | 198 | 140 |

-continued

| Example No. | Structure | Emax % | EC50 (nM) | Binding Affinity Ki (nM) |
| --- | --- | --- | --- | --- |
| 3 | 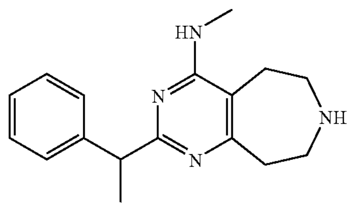 | 60.80 | 804 | 23.2 |
| 8 | 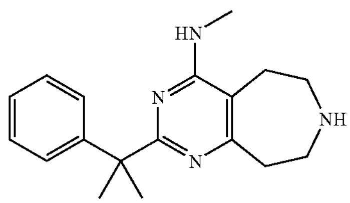 | 54.30 | 128 | 44.5 |
| 9 | 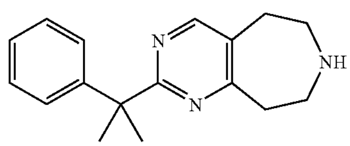 | 52.60 | 732 | 401 |
| 11 | 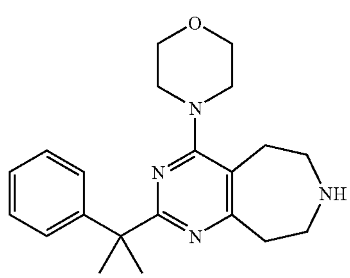 | 75.20 | 884 | 73.5 |
| 13 | 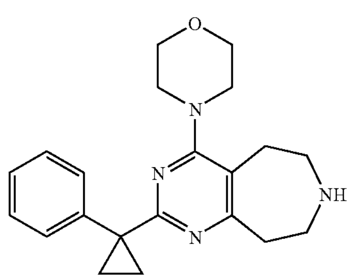 | 64.40 | 499 | 2300 |
| 14 | 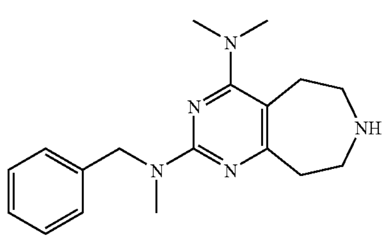 | 50.80 | 279 | 144 |

-continued

| Example No. | Structure | Emax % | EC50 (nM) | Binding Affinity Ki (nM) |
|---|---|---|---|---|
| 15 | 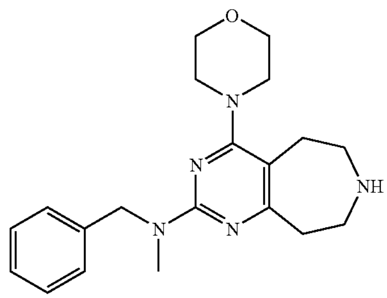 | 64.10 | 202 | 181 |
| 16 | 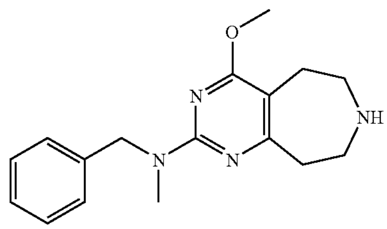 | 41.40 | 526 | 54.7 |
| 17 | 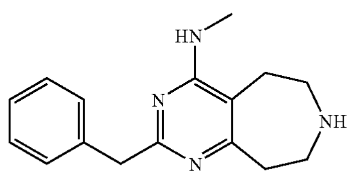 | 29.30 | 39.4 | 30.9 |
| 18 | 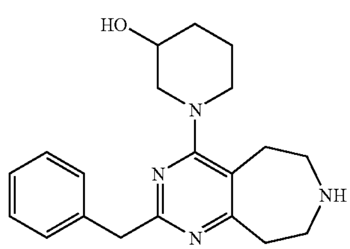 | 51.30 | 558 | 243 |
| 19 | 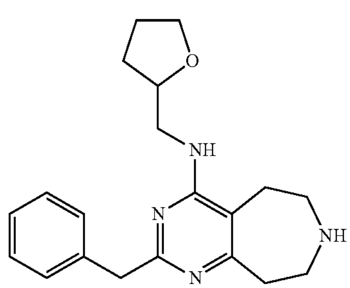 | 36.30 | 344 | 52.4 |
| 23 | 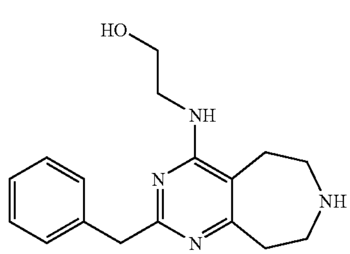 | 72.60 | 159 | 107 |

-continued
| Example No. | Structure | Emax % | EC50 (nM) | Binding Affinity Ki (nM) |
|---|---|---|---|---|
| 24 | 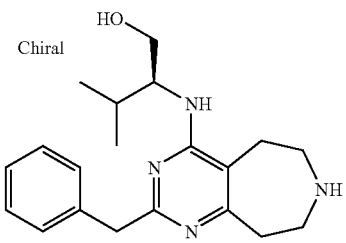 | 69.90 | 119 | 91.4 |
| 26 | 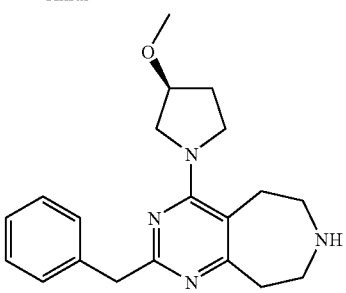 | 60.90 | 417 | 229 |
| 27 | 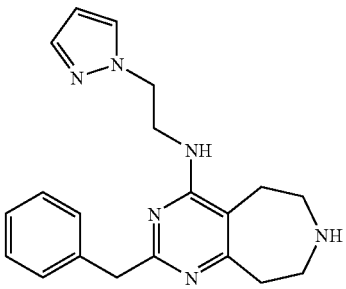 | 35.00 | 57.2 | 25.4 |
| 29 | 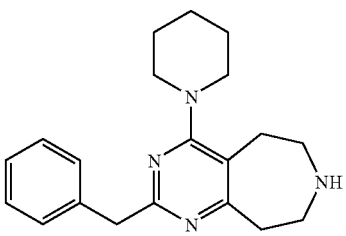 | 37.70 | 962 | 177 |
| 30 | 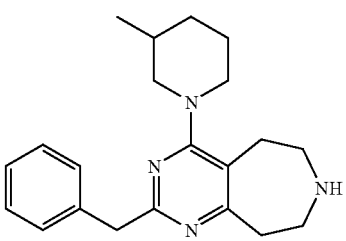 | 54.80 | 984 | 99.1 |

-continued

| Example No. | Structure | Emax % | EC50 (nM) | Binding Affinity Ki (nM) |
|---|---|---|---|---|
| 33 | 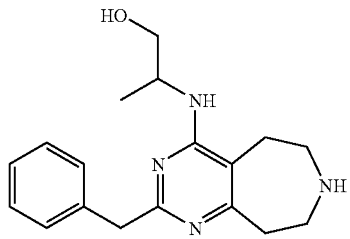 | 58.50 | 424 | 125 |
| 37 | 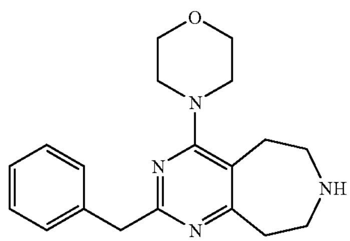 | 92.30 | 33.3 | 19.8 |
| 38 | 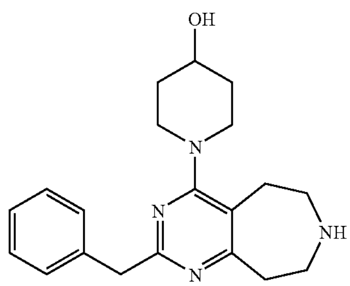 | 66.00 | 336 | 514 |
| 39 | 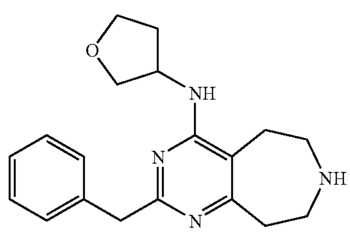 | 30.60 | 516 | 696 |
| 40 | 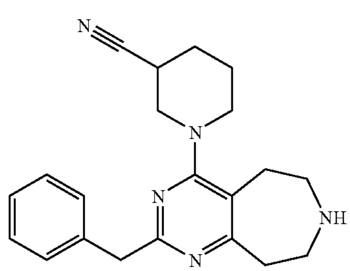 | 40.60 | 309 | 413 |
| 41 | 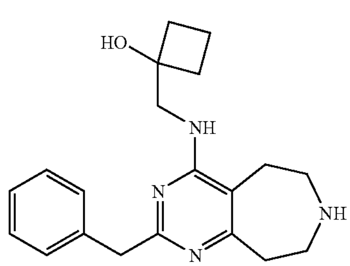 | 74.70 | 57 | 86.9 |

-continued

| Example No. | Structure | Emax % | EC50 (nM) | Binding Affinity Ki (nM) |
|---|---|---|---|---|
| 42 | 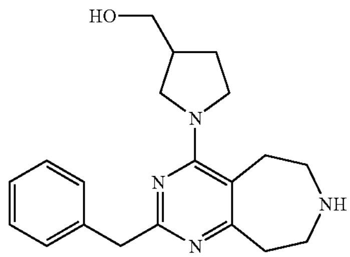 | 75.40 | 67 | 102 |
| 43 | 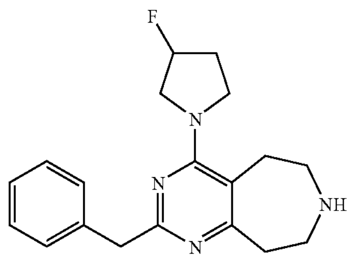 | 52.60 | 190 | 61.0 |
| 44 | 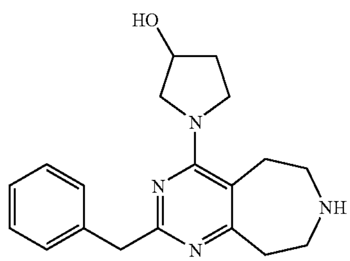 | 75.50 | 136 | 139 |
| 45 | Chiral | 88.40 | 69.5 | 28.4 |
| 46 | 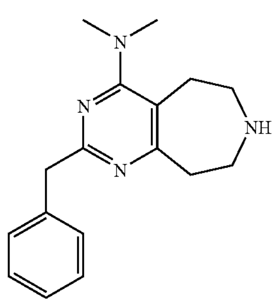 | 55.70 | 154 | 232 |
| 47 (Peak 2) | 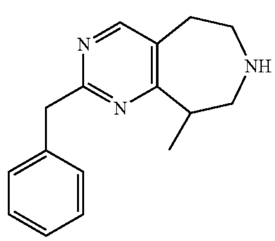 | 76.60 | 233 | 218 |

-continued

| Example No. | Structure | Emax % | EC50 (nM) | Binding Affinity Ki (nM) |
|---|---|---|---|---|
| 47 (Peak 1) | 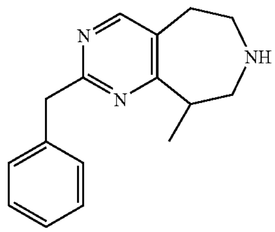 | 96.40 | 453 | 133 |
| 48 (Peak 2) | 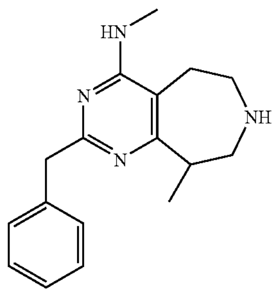 | 63.70 | 36 | 18.6 |
| 49 | 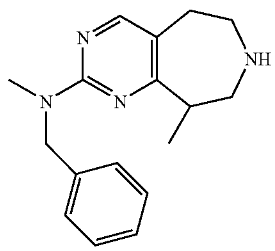 | 71.20 | 182 | — |
| 50 | 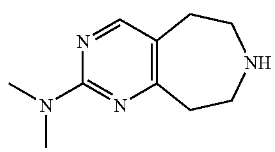 | 100 | 481 | 552 |
| 52 | 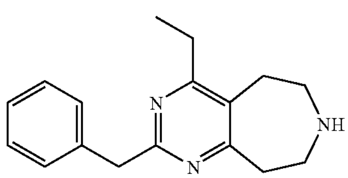 | 71.60 | 314 | 142 |
| 53 | 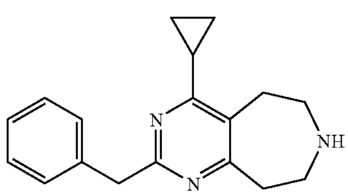 | 49.60 | 293 | 105 |
| 54 | 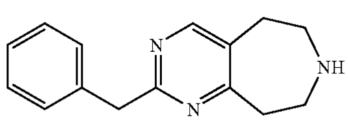 | 75.60 | 194 | 174 |

-continued

| Example No. | Structure | Emax % | EC50 (nM) | Binding Affinity Ki (nM) |
|---|---|---|---|---|
| 55 | 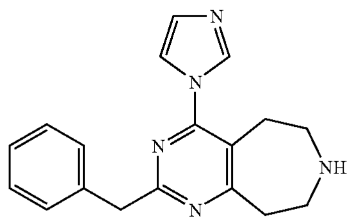 | 72.60 | 263 | 380 |
| 56 | 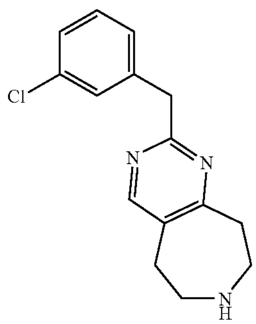 | 55.90 | 180 | 83.9 |
| 57 | 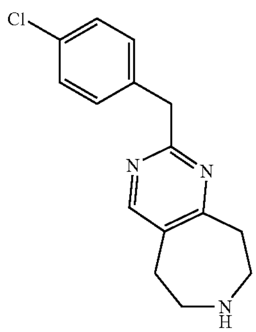 | 64.70 | 192 | — |
| 59 | 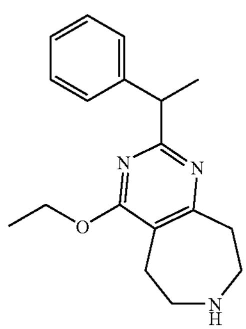 | 33.10 | 107 | 49.3 |
| 60 | 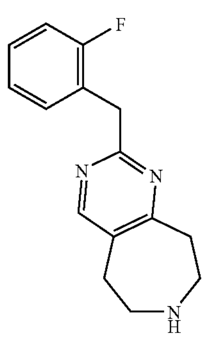 | 65.10 | 194 | — |

-continued

| Example No. | Structure | Emax % | EC50 (nM) | Binding Affinity Ki (nM) |
|---|---|---|---|---|
| 61 | (3-fluorobenzyl-pyrimido-azepine) | 67.10 | 125 | — |
| 62 | (4-fluorobenzyl-pyrimido-azepine) | 59.60 | 309 | 471 |
| 63 | (3-trifluoromethylbenzyl-pyrimido-azepine) | 44.10 | 298 | 308 |
| 64 | (4-methylbenzyl-pyrimido-azepine) | 63.10 | 100 | — |
| 65 | (3-methylbenzyl-pyrimido-azepine) | 83.90 | 211 | 244 |
| 66 | (2-methylbenzyl-pyrimido-azepine) | 70.50 | 332 | 304 |

-continued

| Example No. | Structure | Emax % | EC50 (nM) | Binding Affinity Ki (nM) |
|---|---|---|---|---|
| 67 | 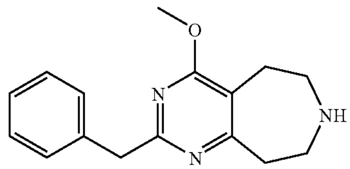 | 31.00 | 86.5 | — |
| 68 | 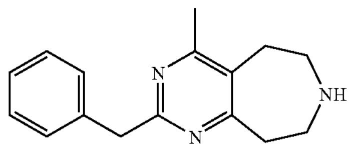 | 71.40% | 179 | 421 |
| 69 | 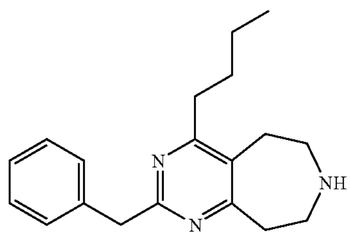 | 77.10 | 274 | 153 |
| 70 | 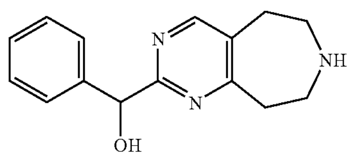 | 76.00 | 643 | 978 |
| 71 | 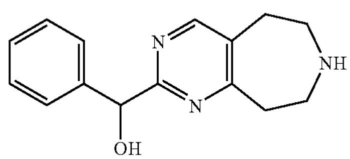 | >10,000 | | |
| 72 | 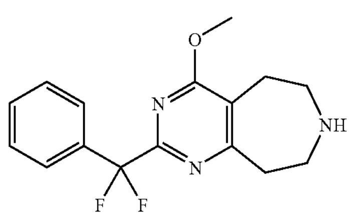 | 41.1 | 80 | 77.7 |
| 72A | 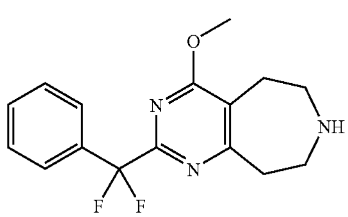 | 31.9 | 35.6 | 15 |

| Example No. | Structure | Emax % | EC50 (nM) | Binding Affinity Ki (nM) |
|---|---|---|---|---|
| 73 | 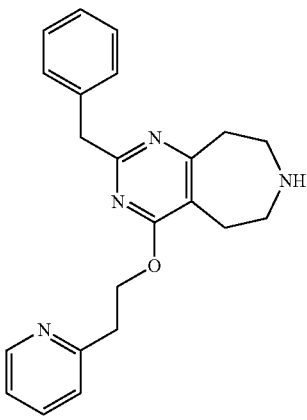 | 83.3 | 8.61 | — |
| 74 | 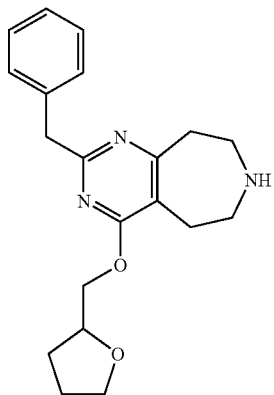 | 86.7 | 17.1 | — |
| 75 | 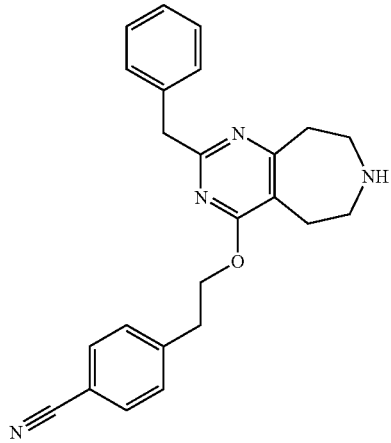 | 90.1 | 58.1 | — |

-continued

| Example No. | Structure | Emax % | EC50 (nM) | Binding Affinity Ki (nM) |
|---|---|---|---|---|
| 76 | 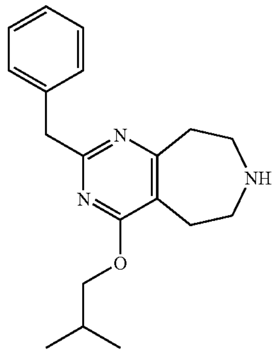 | 34 | 127 | — |
| 77 | 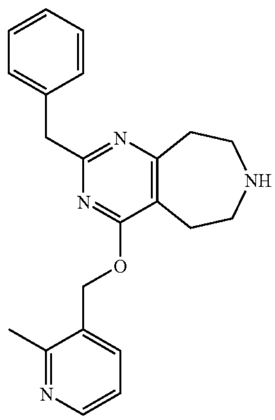 | 70.3 | 130 | — |
| 78 | Chiral | 69.5 | 138 | — |

-continued

| Example No. | Structure | Emax % | EC50 (nM) | Binding Affinity Ki (nM) |
|---|---|---|---|---|
| 79 | 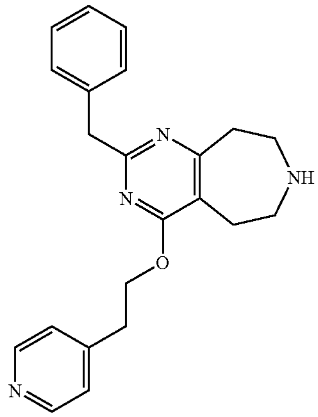 | 67.3 | 154 | — |
| 80 | 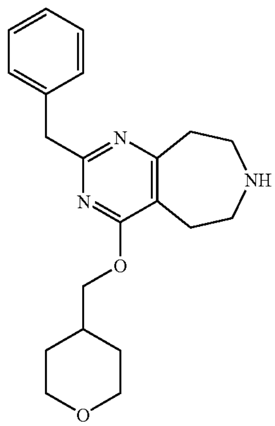 | 74.2 | 184 | — |
| 81 | 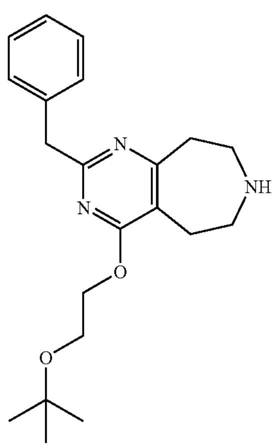 | 60.3 | 195 | — |

-continued

| Example No. | Structure | Emax % | EC50 (nM) | Binding Affinity Ki (nM) |
|---|---|---|---|---|
| 82 | 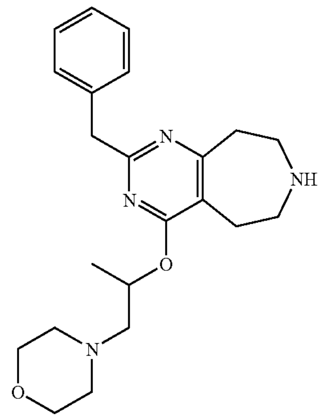 | 71.9 | 304 | — |
| 83 | 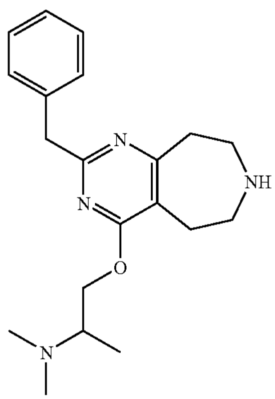 | 45.7 | 338 | — |
| 84 | 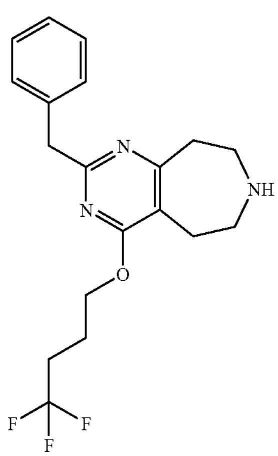 | 36.4 | 395 | — |

-continued
| Example No. | Structure | Emax % | EC50 (nM) | Binding Affinity Ki (nM) |
|---|---|---|---|---|
| 85 | 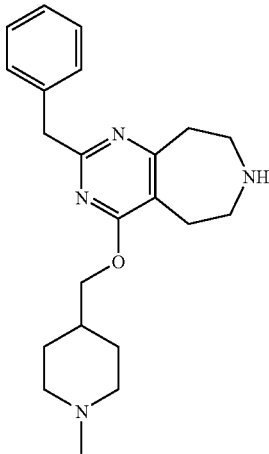 | 86.3 | 421 | — |
| 86 | 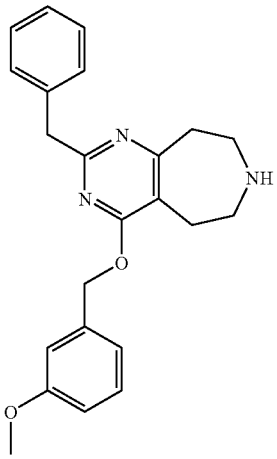 | 82.3 | 541 | — |
| 87 | 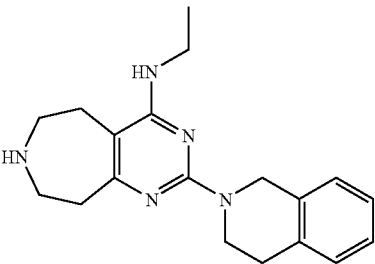 | 57.1 | 48.3 | — |
| 88 | 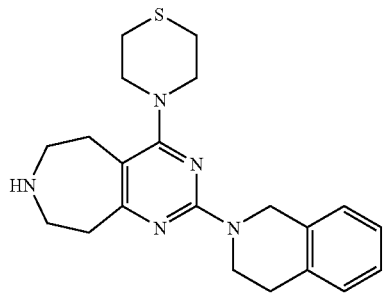 | 67.6 | 838 | — |

| Example No. | Structure | Emax % | EC50 (nM) | Binding Affinity Ki (nM) |
|---|---|---|---|---|
| 89 | 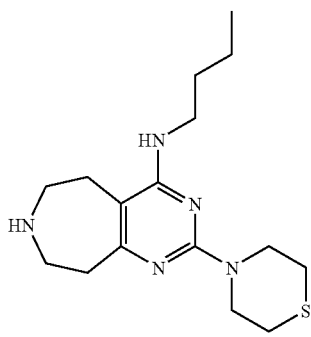 | 48.2 | 33.6 | — |
| 90 | 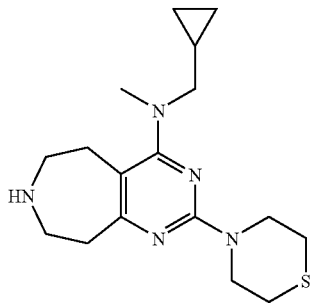 | 87.3 | 75.9 | 24.7 |
| 91 | 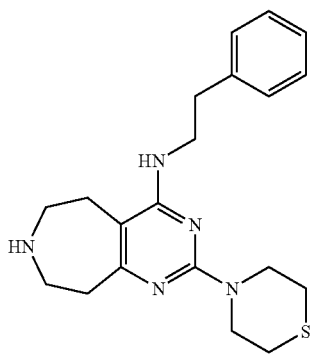 | 69.6 | 186 | — |
| 92 | 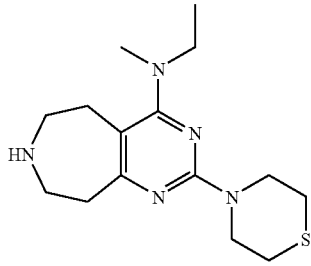 | 77.3 | 90 | — |
| 93 | 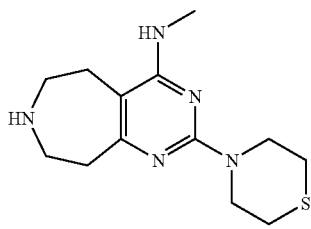 | 77 | 11.5 | — |

-continued
| Example No. | Structure | Emax % | EC50 (nM) | Binding Affinity Ki (nM) |
|---|---|---|---|---|
| 94 | 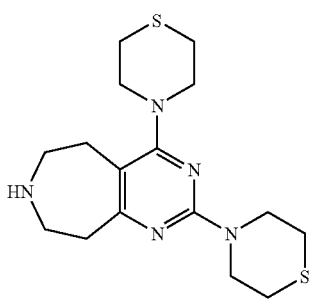 | 80.8 | 261 | — |
| 95 | 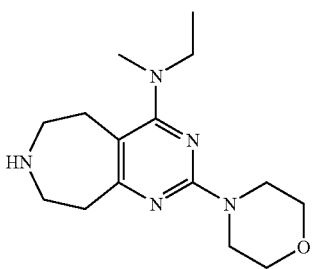 | 88.4 | 229 | — |
| 96 | 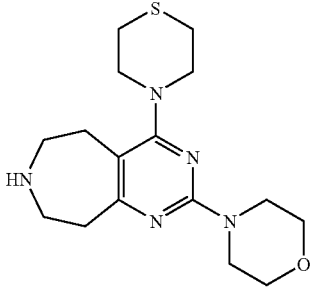 | 66.9 | 311 | — |
| 97 | 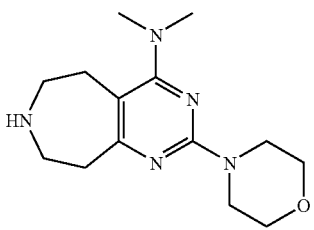 | 84.6 | 67.6 | — |
| 98 | 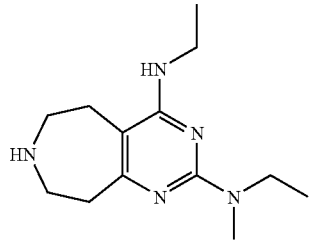 | 61.7 | 77 | 16.3 |

-continued
| Example No. | Structure | Emax % | EC50 (nM) | Binding Affinity Ki (nM) |
|---|---|---|---|---|
| 99 | 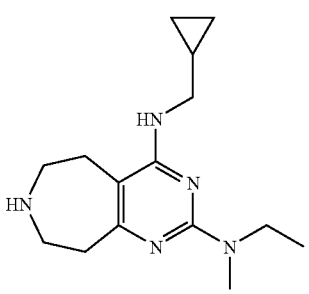 | 69.5 | 103 | — |
| 100 | 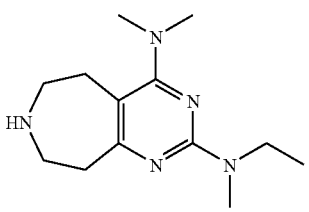 | 51.2 | 122 | — |
| 101 | 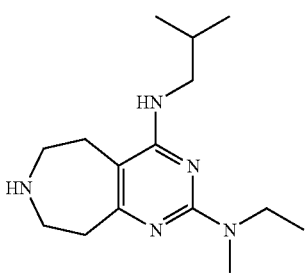 | 49.9 | 326 | — |
| 102 | 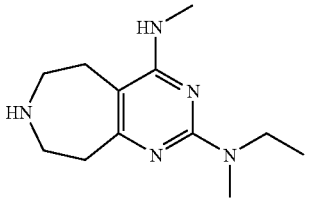 | 74.3 | 173 | — |
| 103 | 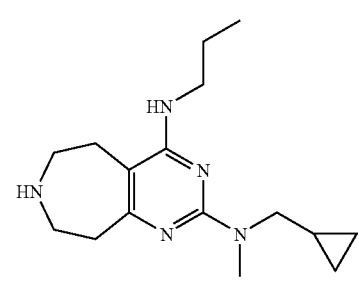 | 32.7 | 449 | — |
| 104 | 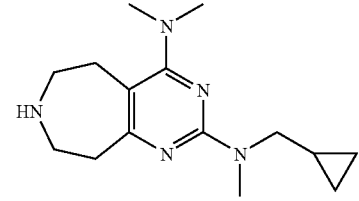 | 69 | 282 | 90.3 |

-continued
| Example No. | Structure | Emax % | EC50 (nM) | Binding Affinity Ki (nM) |
|---|---|---|---|---|
| 105 | 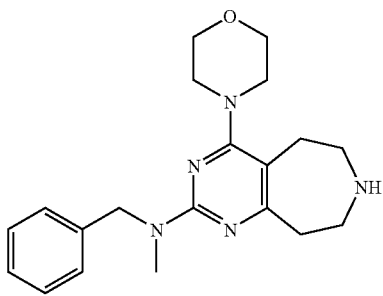 | 64.1 | 202 | — |
| 106 | 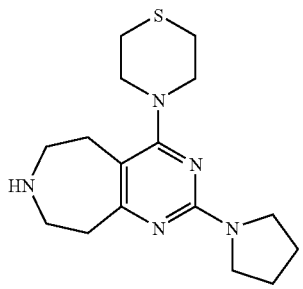 | 78.4 | 100 | 41.6 |
| 107 | 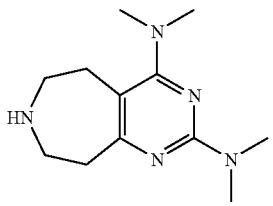 | 43.2 | 363 | — |
| 108 | 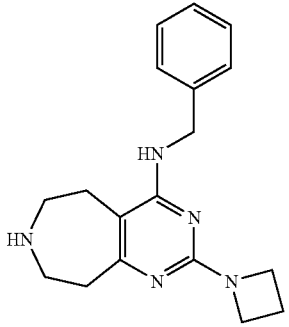 | 44.4 | 149 | — |
| 109 | 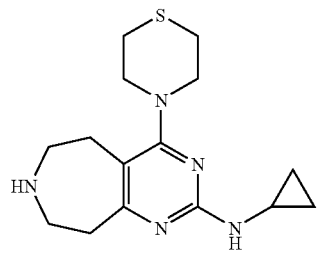 | 87.7 | 247 | — |

-continued

| Example No. | Structure | Emax % | EC50 (nM) | Binding Affinity Ki (nM) |
|---|---|---|---|---|
| 110 | 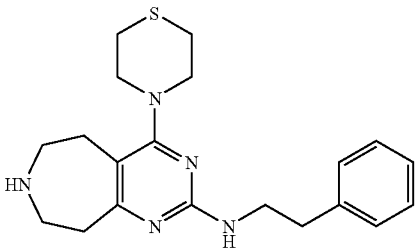 | 38.8 | 604 | — |
| 111 | 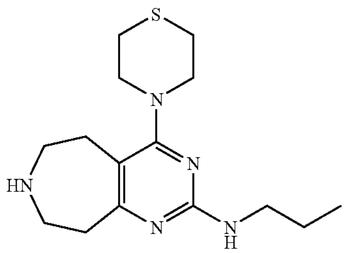 | 64.3 | 141 | — |
| 112 | 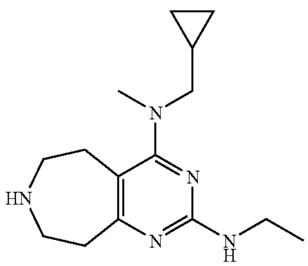 | 42.8 | 543 | — |
| 113 | 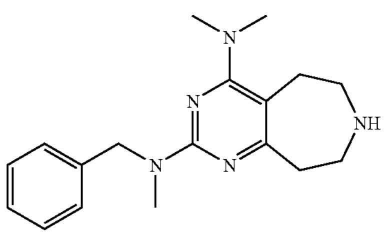 | 50.8 | 279 | — |

EXAMPLES

The invention is illustrated by the following non-limiting examples in which the following abbreviations and definitions are used:

| | |
|---|---|
| Arbocel ® | Filtration agent |
| APCI+ | Atmospheric Pressure Chemical Ionisation (positive scan) |
| BINAP | 2,2'-bis(diphenylphosphino)-1,1'-binaphthyl |
| CDCl$_3$ | Chloroform-d1 |
| d | Doublet |
| DCM | Dichloromethane |
| dd | Doublet of doublets |
| dt | Doublet of triplets |
| DMA | N,N-Dimethylacetamide |
| DMF | N,N-Dimethylformamide |
| DMSO | Dimethylsulfoxide |
| ES+ | Electrospray ionisation positive scan. |

-continued

| | |
|---|---|
| eq | Equivalent |
| h | Hour |
| $^1$H NMR | Proton Nuclear Magnetic Resonance Spectroscopy |
| HRMS | High resolution mass spectrum |
| LCMS | Liquid chromatography-mass spectroscopy |
| LRMS | Low resolution mass spectrum |
| MS | (Low Resolution) Mass Spectroscopy |
| m | Multiplet |
| MeOH | Methanol |
| min | Minute |
| mp | Melting point |
| m/z | Mass spectrum peak |
| NMP | 1-methyl-2-pyrrolidinone |
| Pd$_2$dba$_3$ | tris-(dibenzylideneacetone)dipalladium(0) |
| PXRD | Powder X-Ray Diffraction |
| q | Quartet |
| s | Singlet |
| t | Triplet |
| Tf | (Trifluoromethyl)sulfonyl |
| THF | Tetrahydrofuran |

| δ | Chemical shift |
|---|---|
| 0.880NH$_3$ | Concentrated aqueous ammonia solution (sp.gr.0.880) |

The melting point was measured using a Gallenkamp MPD350 apparatus.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (m/z) were recorded using either electrospray ionisation (ESI) or atmospheric pressure chemical ionisation (APCI). The following abbreviations have been used for common solvents: CDCl$_3$, deuterochloroform; D$_6$-DMSO, deuterodimethylsulphoxide; CD$_3$OD, deuteromethanol; THF, tetrahydrofuran. 'Ammonia' refers to a concentrated solution of ammonia in water possessing a specific gravity of 0.88. Where thin layer chromatography (TLC) has been used, it refers to silica gel TLC using silica gel 60 F$_{254}$ plates, R$_f$ is the distance travelled by a compound divided by the distance travelled by the solvent front on a TLC plate. The term "Catalyst 1" refers to a catalyst (available from ASDI) of the following structure:

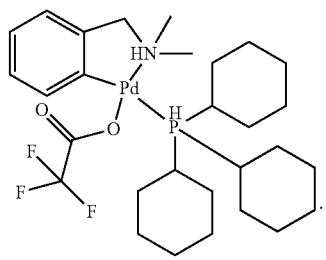

HPLC, unless otherwise indicated, was performed as follows:
Method A: Column: Sunfire C18 4.6×50 mm id; Mobile Phase A: 0.05% formic acid in water; Mobile Phase B: 0.05% formic acid in acetonitrile.
Method B: Column: Xterra 4.6×50 mm id; Mobile Phase A: 0.05% ammonia in water; Mobile Phase B: 0.05% ammonia in acetonitrile
Method C: Column: Luna C8 4.6×50 mm id; Mobile Phase A: 10 mM ammonium acetate in water; Mobile Phase B: 10 mM ammonium acetate in acetonitrile
Method D: Column: C18 4.6×50 mm id; Mobile Phase A: 0.1% formic acid in water; Mobile Phase B: 0.1% formic acid in acetonitrile.

Example 1

2-Benzyl-4-(1H-pyrazol-1-yl)-6,7,8,9-tetrahydro-5H-pyrimido[4,5-d]azepine and 2-benzyl-4-(1H-pyrazol-1-yl)-6,7,8,9-tetrahydro-5H-pyrimido[4,5-d]azepine hydrochloride

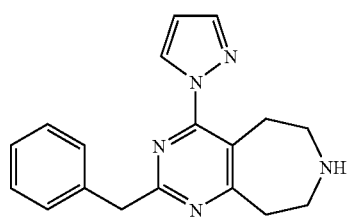

Pyrazole (192 mg, 2.80 mmol) was added to a solution of the triflate of Preparation 1, step B (686 mg, 1.40 mmol) in MeCN (5.0 mL) at room temperature with stirring. The mixture was heated to 80° C. and stirred for 20 h. The reaction was cooled to room temperature and a solution of HCl in dioxane (2.0 mL, 4M, 8.0 mmol) was added and the resulting solution was stirred at room temperature for 1 h. The reaction was quenched by addition of saturated sodium bicarbonate and extracted into CH$_2$Cl$_2$. The combined organics were dried over magnesium sulfate, filtered and concentrated in vacuo to provide the crude product as a brown gum. The product was purified by flash column chromatography eluting with ethyl acetate:MeOH:NH$_3$ (85:15:2) to yield the title compound as a yellow gum (353 mg, 82% yield). This was taken up in methanol and a solution of HCl in diethyl ether added to convert the product to the HCl salt. The resulting solution was concentrated to yield a yellow solid. Recrystallisation from MeOH provided the hydrochloride salt as a white solid.

$^1$H NMR (400 MHZ, CDCl$_3$) free base δ: 2.99-3.08 (m, 4H); 3.19-325 (m, 2H); 3.39-3.42 (m, 2H); 4.20 (s, 2H); 6.42 (dd, 1H); 7.19-7.33 (m, 3H); 7.39 (d, 2H); 7.75 (dd, 1H); 8.34 (d, 1H).

$^1$H NMR (400 MHZ, CDCl$_3$) HCl salt δ: 3.42-3.48 (m, 6H); 3.69-3.73 (m, 2H); 4.23 (s, 2H); 6.58 (dd, 1H); 7.19-7.24, (m, 1H); 7.26-7.32 (m, 2H); 7.35-7.39. LCMS Rt=2.04 min; ES+ AP+ m/z 306 [MH]$^+$.

Example 2

2-(1-Phenylethyl)-6,7,8,9-tetrahydro-5H-pyrimido[4,5-d]azepine

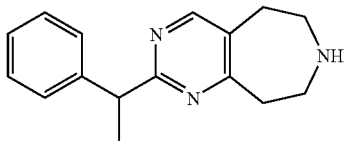

A solution of HCl in dioxane (1.0 mL, 4M, 4.0 mmol) was added to a solution of tert-butyl 2-(1-phenylethyl)-5,6,8,9-tetrahydro-7H-pyrimido[4,5-d]azepine-7-carboxylate of Preparation 2, Step D, (150 mg, 0.40 mmol) in CH$_2$Cl$_2$ (2.0 mL). The mixture was stirred at room temperature for 2 h. The reaction was quenched by addition of sat sodium bicarbonate and extracted into CH$_2$Cl$_2$. The combined organics were dried over magnesium sulfate, filtered and concentrated in vacuo to provide the crude product as a brown gum (45 mg). The title compound was purified by reverse phase HPLC.

LCMS Rt=1.70 min; ES+ AP+ m/z 254 [MH]$^+$.

Example 3

N-methyl-2-(1-phenylethyl)-6,7,8,9-tetrahydro-5H-pyrimido[4,5-d]azepin-4-amine

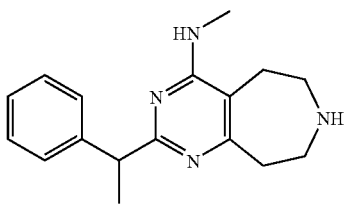

A similar method to that of Example 2, starting from tert-butyl 4-(methylamino)-2-(1-phenylethyl)-5,6,8,9-tetrahydro-7H-pyrimido[4,5-d]azepine-7-carboxylate of Preparation 3 provided the crude product as a brown gum (45 mg), which was purified by reverse phase HPLC.

LCMS Rt=0.57 min; ES+ AP+ m/z 283 [MH]$^+$.

Example 4

(R,S)-2-Benzyl-4-(2-methyl-pyrrolidin-1-yl)-6,7,13,9-tetrahydro-5H-pyrimido[4,5-d]azepine dihydrochloride

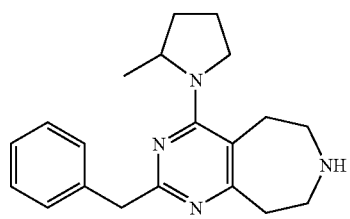

A similar method to that of Example 2, followed by conversion to the hydrochloride salt as described in Example 1, starting from (R,S)-2-Benzyl-4-(2-methyl-pyrrolidin-1-yl)-5,6,8,9-tetrahydro-pyrimido[4,5-d]azepine-7-carboxylic acid tert-butyl ester of Preparation 4, Step B, provided 53 mg of the title compound in 68% yield.

$^1$H-NMR (400 MHz, DMSO-$d_6$) δ 1.14 (d, 3H), 1.56 (m, 1H), 1.70 (m, 1H), 1.98 (m, 1H), 2.09 (m, 1H), 3.04 (m, 1H) 3.18 (m, 1H), 3.27 (m, 2H), 3.34 (m, 2H), 3.39 (m, 2H), 3.59 (m, 1H), 3.81 (m, 1H), 4.16 (m, 2H), 4.25 (m, 1H), 7.27 (m, 1H), 7.35 (m, 2H), 7.42 (m, 2H), 9.47 (m, 2H); LRMS ESI m/z 323 [MH]+.

Example 5

2-(4-Fluorobenzyl)-N-methyl-6,7,8,9-tetrahydro-5H-pyrimido[4,5,d]azepine-4-amine

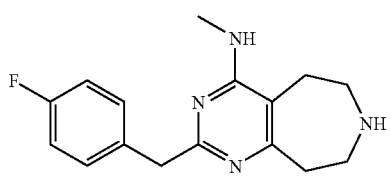

A similar method to that of Example 2, starting from the product of Preparation 5, Step D, provided 54 mg of the title compound as a brown oil.
LCMS Rt=3.05 min; ES+ m/z 287 [MH]+.

Example 6

2-(4-Fluorobenzyl)-N,N-dimethyl-6,7,8,9-tetrahydro-5H-pyrimido[4,5,d]azepine-4-amine

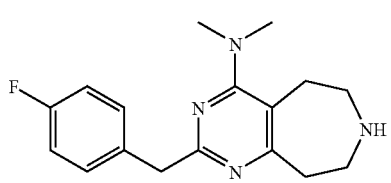

The title compound was prepared in a manner identical to Example 2, starting from tert-butyl 4-(dimethylamino)-2-(4-fluorobenzyl)-5,6,8,9-tetrahydro-7H-pyrimido[4,5,d]azepine-7-carboxylate of Preparation 6, to give the title compound as a brown oil (70 mg).
LCMS Rt=3.36 min; ES+ AP+ m/z 301 [MH]+.

Example 7

2-(4-Fluorobenzyl)-4-pyrrolidin-1-yl-6,7,8,9-tetrahydro-5H-pyrimido[4,5,d]azepine-4-amine

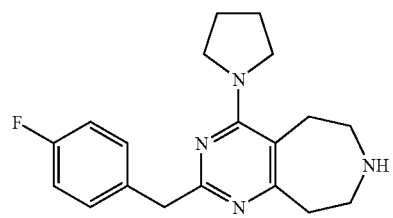

The title compound was prepared by a similar method to that of Example 2 starting from tert-butyl 2-(4-fluorobenzyl)-4-pyrrolidin-1-yl-5,6,8,9-tetrahydro-7H-pyrimido[4,5,d]azepine-7-carboxylate of Preparation 7.
LCMS Rt=3.60 min; ES+ AP+ m/z 327 [MH]+.

Example 8

2-[Difluoro(phenyl)methyl]-N-methyl-6,7,8,9-tetrahydro-5H-pyrimido[4,5-d]azepin-4-amine

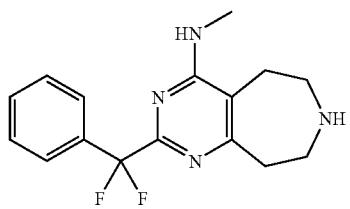

A similar method to that of Example 6, starting from tert-butyl 2-[difluoro(phenyl)methyl]-4-(methylamino)-5,6,8,9-tetrahydro-7H-pyrimido[4,5-d]azepine-7-carboxylate of Preparation 8, Step D, provided the crude product as a brown gum (40 mg) which was purified by reverse phase HPLC.
$^1$H NMR (400 MHZ, CDCl$_3$) δ: 2.90-3.15 (m, 8H); 2.98 (s, 3H); 7.38-7.42 (m, 3H); 7.68-7.78 (m, 2H). LCMS Rt=1.95 min; ES+ AP+ m/z 305 [MH]+.

Example 9

2-(1-Methyl-1-phenylethyl)-6,7,8,9-tetrahydro-5H-pyrimido[4,5-d]azepine

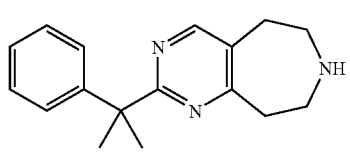

A similar method to that of Example 2, starting from the product of Preparation 10, provided the crude product as a brown gum (30 mg) which was purified by reverse phase HPLC.

LCMS Rt=2.09 min; ES+ AP+ m/z 268 [MH]+.

Example 10

N-methyl-2-(1-methyl-1-phenylethyl)-6,7,8,9-tetrahydro-5H-pyrimido[4,5-d]azepin-4-amine

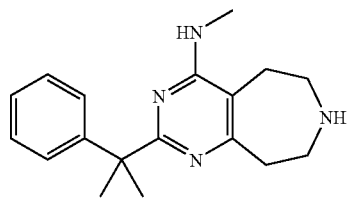

A similar method to that of Example 2, starting the product of Preparation 11, provided the crude product as a brown gum (25 mg) which was purified by reverse phase HPLC.

LCMS Rt=1.41 min; AP+ m/z 295 [MH]+.

Example 11

2-(1-Methyl-1-phenylethyl)-4-morpholin-4-yl-6,7,8,9-tetrahydro-5H-pyrimido[4,5-d]azepine

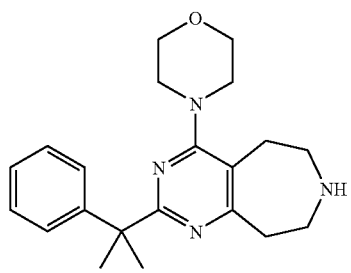

A similar method to that of Example 2, starting from the product of Preparation 12 provided the crude product as a brown gum (34 mg) which was purified by reverse phase HPLC.

LCMS Rt=1.81 min; ES+ AP+ m/z 353 [MH]+.

Example 12

2-(1-Methyl-1-phenylethyl)-4-pyrrolidin-1-yl-6,7,8,9-tetrahydro-5H-pyrimido[4,5-d]azepine

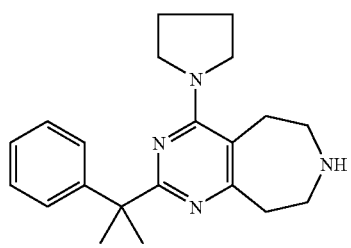

A similar method to that of Example 2, starting from the product of Preparation 13 provided the crude product as a brown gum (35 mg) which was purified by reverse phase HPLC.

LCMS Rt=1.75 min; ES+ AP+ m/z 337 [MH]+.

Example 13

4-Morpholin-4-yl-2-(1-phenylcyclopropyl)-6,7,8,9-tetrahydro-5H-pyrimido[4,5-d]azepine

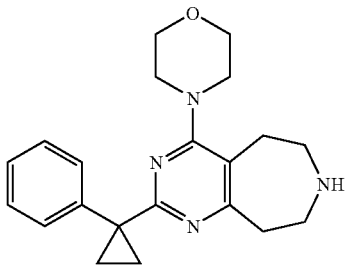

A similar method to that of Example 2, starting from the product of Preparation 15 provided the crude product as a brown gum (60 mg) which was purified by reverse phase HPLC.

LCMS Rt=1.76 min; ES+ AP+ m/z 351 [MH]+.

Example 14

N-2-benzyl-N-2,N-4,N-4-trimethyl-6,7,8,9-tetrahydro-5H-pyrimido[4,5,d]azepin-2-amine

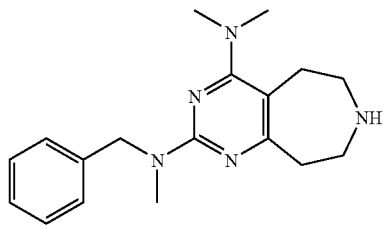

A similar method to that of Example 2, starting the product of Preparation 16, Step C provided the crude product as a yellow oil (43 mg) which was purified by reverse phase HPLC.

LCMS Rt=5.39 min; ES+ AP+ m/z 312 [MH]+.

Example 15

N-benzyl-N-methyl-4-morpholin-4-yl-6,7,8,9-tetrahydro-5H-pyrimido[4,5,d]azepin-2-amine

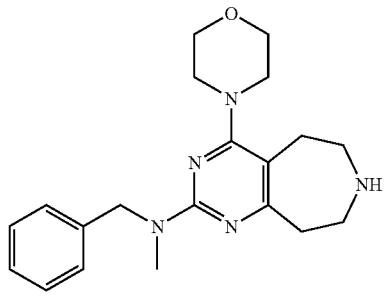

The title compound was prepared by a similar method to example 2, starting from the product of Preparation 17.
LCMS Rt=0.53 min; ES+ AP+ m/z 354 [MH]+.

Example 16

N-benzyl-4-methoxy-N-methyl-6,7,8,9-tetrahydro-5H-pyrimido[4,5,d]azepin-2-amine

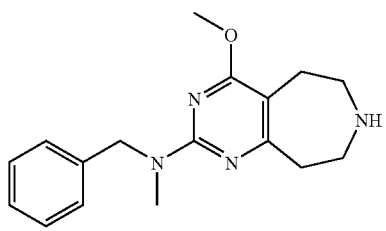

A similar method to that of Example 2, starting from the product of Preparation 18, afforded the title compound as a colourless oil (15 mg, 65%).

¹HNMR 400 MHz CDCl₃ δ: 2.76-2.80 (m, 2H), 2.86-2.95 (m, 4H), 2.96-3.02 (m, 2H), 3.11 (s, 3H), 3.85 (s, 3H), 4.87 (s, 2H), 7.22-7.33 (m, 5H). LRMS ES+ and AP+ m/z 299 [MH]+.

Examples 17 to 46

The compounds of general formula

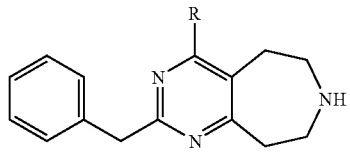

were prepared using the following method.

To a solution of tert-butyl 2-benzyl-4-{[(trifluoromethyl)sulfonyl]oxy}-5,6,8,9-tetrahydro-7H-pyrimido[4,5-d]azepine-7-carboxylate of Preparation 1, Step B (1 mmol) in DMA (15 ml) was added the required amine (6 mmol). The reaction mixture was stirred at room temperature for 16 h. The solvent was removed under reduced pressure and the crude taken on for deprotection without further purification. The crude was taken up in dioxane (2 ml) and 4 N HCl in dioxane (2 eq) added. The reaction mixture was stirred at room temperature for 2 h. The reaction mixture was concentrated in vacuo. The resulting solid was triturated with ether to yield the product as HCl salt.

| Ex. No. | R | Data | Name |
|---|---|---|---|
| 17 | HN-CH₃ | δ: 3.05 (m, 2H), 3.12 (m, 3H), 3.34 (m, 2H), 3.47 (m, 2H), 3.53 (m, 2H), 4.18 (s, 2H), 7.29 (m, 1H), 7.35 (m, 2H), 7.42 (m, 2H). APCl m/z 269 [MH]+; 100% | 2-benzyl-N-methyl-6,7,8,9-tetrahydro-5H-pyrimido[4,5-d]azepin-4-amine hydrochloride |
| 18 | piperidin-3-ol | LCMS Rt = 3.13 min; ES+ m/z 339 [MH]+. | 1-(2-benzyl-6,7,8,9-tetrahydro-5H-pyrimido[4,5-d]azepin-4-yl)piperidin-3-ol hydrochloride |
| 19 | HN-CH₂-(tetrahydrofuran-2-yl) | LCMS Rt = 1.86 min; ES+ m/z 339 [MH]+. | 2-benzyl-N-(tetrahydrofuran-2-ylmethyl)-6,7,8,9-tetrahydro-5H-pyrimido[4,5-d]azepin-4-amine hydrochloride |
| 20 | 2-methylpyrrolidin-1-yl | δ: 1.14 (d, 3H), 1.56 (m, 1H), 1.70 (m, 1H), 1.98 (m, 1H), 2.09 (m, 1H), 3.04 (m, 1H) 3.18 (m, 1H), 3.27 (m, 2H), 3.34 (m, 2H), 3.39 (m, 2H), 3.59 (m, 1H), 3.81 (m, 1H), 4.16 (m, 2H), 4.25 (m, 1H), 7.27 (m, 1H), 7.35 (m, 2H), 7.42 (m, 2H), 9.47 (m, 2H); LRMS ESI m/z 323 [MH]+ | 2-benzyl-4-(2-methylpyrrolidin-1-yl)-6,7,8,9-tetrahydro-5H-pyrimido[4,5-d]azepine hydrochloride |
| 21 | (3S,4R)-4-aminotetrahydrofuran-3-ol | LCMS Rt = 2.67 min; ES+ m/z 341 [MH]+. | (3S,4R)-4-[(2-benzyl-6,7,8,9-tetrahydro-5H-pyrimido[4,5-d]azepin-4-yl)amino]tetrahydrofuran-3-ol hydrochloride |

| Ex. No. | R | Data | Name |
|---|---|---|---|
| 22 | (3R)-3-methoxypyrrolidine | LCMS Rt = 3.30 min; ES+ m/z 339 [MH]+. | 2-benzyl-4-[(3R)-3-methoxypyrrolidin-1-yl]-6,7,8,9-tetrahydro-5H-pyrimido[4,5-d]azepine hydrochloride |
| 23 | HO-CH2CH2-NH | LCMS Rt = 2.83 min; ES+ m/z 299 [MH]+. | 2-[(2-benzyl-6,7,8,9-tetrahydro-5H-pyrimido[4,5-d]azepin-4-yl)amino]ethanol hydrochloride |
| 24 | HO-CH2-CH(iPr)-NH | LCMS Rt = 3.20 min; ES+ m/z 341 [MH]+. | (2S)-2-[(2-benzyl-6,7,8,9-tetrahydro-5H-pyrimido[4,5-d]azepin-4-yl)amino]-3-methylbutan-1-ol hydrochloride |
| 25 | 2-methylpiperidine | LCMS Rt = 3.84 min; ES+ m/z 337 [MH]+. | 2-benzyl-4-(2-methylpiperidin-1-yl)-6,7,8,9-tetrahydro-5H-pyrimido[4,5-d]azepine hydrochloride |
| 26 | (3S)-3-methoxypyrrolidine | LCMS Rt = 3.36 min; ES+ m/z 339 [MH]+. | 2-benzyl-4-[(3S)-3-methoxypyrrolidin-1-yl]-6,7,8,9-tetrahydro-5H-pyrimido[4,5-d]azepine hydrochloride |
| 27 | pyrazol-1-yl-ethyl-NH | LCMS Rt = 2.93 min; ES+ m/z 349 [MH]+. | 2-benzyl-N-[2-(1H-pyrazol-1-yl)ethyl]-6,7,8,9-tetrahydro-5H-pyrimido[4,5-d]azepin-4-amine hydrochloride |
| 28 | N,N-diethylamino | LCMS Rt = 3.75 min; ES+ m/z 311 [MH]+. | 2-benzyl-N,N-diethyl-6,7,8,9-tetrahydro-5H-pyrimido[4,5-d]azepin-4-amine hydrochloride |
| 29 | piperidine | LCMS Rt = 3.73 min; ES+ m/z 323 [MH]+. | 2-benzyl-4-piperidin-1-yl-6,7,8,9-tetrahydro-5H-pyrimido[4,5-d]azepine hydrochloride |
| 30 | 3-methylpiperidine | LCMS Rt = 3.98 min; ES+ m/z 337 [MH]+. | 2-benzyl-4-(3-methylpiperidin-1-yl)-6,7,8,9-tetrahydro-5H-pyrimido[4,5-d]azepine hydrochloride |
| 31 | N-isopropyl-N-methylamino | LCMS Rt = 3.83 min; ES+ m/z 311 [MH]+. | 2-benzyl-N-isopropyl-N-methyl-6,7,8,9-tetrahydro-5H-pyrimido[4,5-d]azepin-4-amine hydrochloride |

-continued

| Ex. No. | R | Data | Name |
|---|---|---|---|
| 32 | (2-methoxy-1-methylethyl)amino | LCMS Rt = 3.28 min; ES+ m/z 327 [MH]+. | 2-benzyl-N-(2-methoxy-1-methylethyl)-6,7,8,9-tetrahydro-5H-pyrimido[4,5-d]azepin-4-amine hydrochloride |
| 33 | (1-hydroxymethyl-ethyl)amino | LCMS Rt = 2.78 min; ES+ m/z 313 [MH]+. | 2-[(2-benzyl-6,7,8,9-tetrahydro-5H-pyrimido[4,5-d]azepin-4-yl)amino]propan-1-ol hydrochloride |
| 34 | 4-methylpiperidin-1-yl | LCMS Rt = 3.97 min; ES+ m/z 337 [MH]+. | 2-benzyl-4-(4-methylpiperidin-1-yl)-6,7,8,9-tetrahydro-5H-pyrimido[4,5-d]azepine, hydrochloride |
| 35 | (2-methoxyethyl)amino | LCMS Rt = 3.00 min; ES+ m/z 313 [MH]+. | 2-benzyl-N-(2-methoxyethyl)-6,7,8,9-tetrahydro-5H-pyrimido[4,5-d]azepin-4-amine hydrochloride |
| 36 | ethylamino | LCMS Rt = 3.30 min; ES+ m/z 283 [MH]+. | 2-benzyl-N-ethyl-6,7,8,9-tetrahydro-5H-pyrimido[4,5-d]azepin-4-amine hydrochloride |
| 37 | morpholin-4-yl | LCMS Rt = 3.05 min; ES+ m/z 325 [MH]+. | 2-benzyl-4-morpholin-4-yl-6,7,8,9-tetrahydro-5H-pyrimido[4,5-d]azepine hydrochloride |
| 38 | 4-hydroxypiperidin-1-yl | LCMS Rt = 2.91 min; ES+ m/z 339 [MH]+. | 1-(2-benzyl-6,7,8,9-tetrahydro-5H-pyrimido[4,5-d]azepin-4-yl)piperidin-4-ol hydrochloride |
| 39 | (tetrahydrofuran-3-yl)amino | LCMS Rt = 2.85 min; ES+ m/z 325 [MH]+. | 2-benzyl-N-(tetrahydrofuran-3-yl)-6,7,8,9-tetrahydro-5H-pyrimido[4,5-d]azepin-4-amine hydrochloride |
| 40 | 3-cyanopiperidin-1-yl | LCMS Rt = 3.15 min; ES+ m/z 348 [MH]+. | 1-(2-benzyl-6,7,8,9-tetrahydro-5H-pyrimido[4,5-d]azepin-4-yl)piperidine-3-carbonitrile hydrochloride |

| Ex. No. | R | Data | Name |
|---|---|---|---|
| 41 | 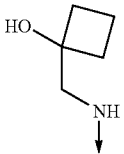 | LCMS Rt = 3.07 min; ES+ m/z 339 [MH]+. | 1-{[(2-benzyl-6,7,8,9-tetrahydro-5H-pyrimido[4,5-d]azepin-4-yl)amino]methyl}cyclobutanol hydrochloride |
| 42 |  | LCMS Rt = 3.21 min; ES+ m/z 339 [MH]+. | [1-(2-benzyl-6,7,8,9-tetrahydro-5H-pyrimido[4,5-d]azepin-4-yl)pyrrolidin-3-yl]methanol hydrochloride |
| 43 | 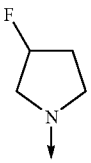 | LCMS Rt = 3.08 min; ES+ m/z 327 [MH]+. | 2-benzyl-4-(3-fluoropyrrolidin-1-yl)-6,7,8,9-tetrahydro-5H-pyrimido[4,5-d]azepine hydrochloride |
| 44 | 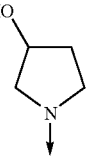 | LCMS Rt = 3.07 min; ES+ m/z 325 [MH]+. | 1-(2-benzyl-6,7,8,9-tetrahydro-5H-pyrimido[4,5-d]azepin-4-yl)pyrrolidin-3-ol hydrochloride |
| 45 | 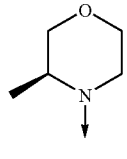 | LCMS Rt = 3.22 min; ES+ m/z 339 [MH]+. | 2-benzyl-4-[(3S)-3-methylmorpholin-4-yl]-6,7,8,9-tetrahydro-5H-pyrimido[4,5-d]azepine hydrochloride |
| 46 |  | LCMS Rt = 3.29 min; ES+ m/z 283 [MH]+. | 2-benzyl-N,N-dimethyl-6,7,8,9-tetrahydro-5H-pyrimido[4,5-d]azepin-4-amine hydrochloride |

Example 47

2-Benzyl-9-methyl-6,7,8,9-tetrahydro-5H-pyrimido[4,5-d]azepine

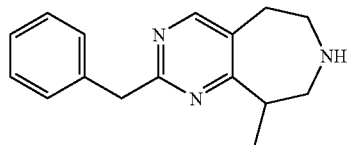

A similar method to that of Example 2, starting from the product of Preparation 19, Step D, gave the title compound as two enantiomers which were subsequently separated by chiral purification.

$^1$H NMR (400 MHz, CD$_3$OD) δ: 1.40 (d, 3H), 3.05 (m, 2H), 3.36 (m, 1H), 3.51 (m, 4H), 4.19 (2H, s), 7.18 (1H, m), 7.24 (2H, m), 7.32 (2H, m), 8.43 (1H, s).

LRMS APCI m/z 254 [MH]+.

Example 48

2-Benzyl-N,9-dimethyl-6,7,8,9-tetrahydro-5H-pyrimido[4,5-d]azepin-4-amine

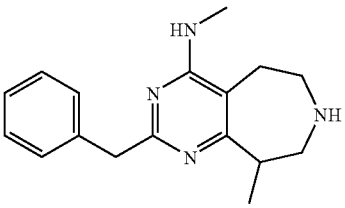

The title compound was prepared by a similar method to that of Examples 17 to 46, starting from the triflate of Preparation 19, Step C. Chiral purification on Chiracel OD-H column eluting with Heptane/IPA/DEA (85/15/0.1) afforded two enantiomers (Peak 1, Rt=9.95 min) and (Peak 2, Rt=11.81 min).

¹H NMR (400 MHz, CD₃OD) δ: 1.50 (d, 3H), 3.06 (m, 2H), 3.08 (s, 3H), 3.35 (m, 1H), 3.50 (m, 4H), 4.18 (s, 2H), 7.26 (m, 1H), 7.27 (m, 2H), 7.41 (m, 2H)
LRMS APCI m/z 283 [MH]⁺

Example 49

N-benzyl-N-methyl-6,7,8,9-tetrahydro-5H-pyrimido[4,5-d]azepin-2-amine hydrochloride

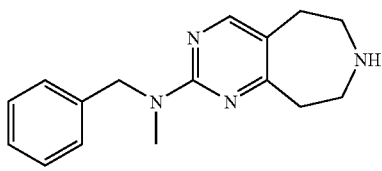

To a solution of the product of Preparation 21 (2 mmol) in dioxane (3 ml) was added 4 N HCl in dioxane. The reaction mixture was stirred at room temperature for 2 h. The reaction mixture was concentrated in vacuo. The resulting solid was triturated with diethyl ether to yield the pure product in 12% yield
¹H NMR (400 MHz, CD₃OD) δ: 2.73 (m, 2H), 2.88 (m, 2H), 2.95 (m, 4H), 3.07 (s, 3H), 4.86 (s, 2H), 7.21-7.35 (m, 5H), 7.99 (s, 2H). LRMS APCI m/z 269 [MH]

Example 50

N,N-dimethyl-6,7,8,9-tetrahydro-5H-pyrimido[4,5-d]azepin-2-amine hydrochloride

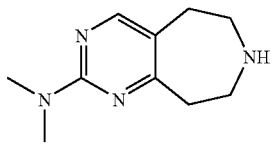

The title compound was prepared from the product of Preparation 22 in 18% yield using a similar method to that of Example 49.
¹H NMR (400 MHz, CD₃OD) δ: 2.96 (m, 4H), 3.11 (m, 4H), 3.15 (s, 6H), 7.98 (s, 1H).
LRMS APCI m/z 193 [MH]⁺.

Example 51

(2-Benzyl-6,7,8,9-tetrahydro-5H-pyrimido[4,5-d]azepin-4-yl)-(1-methyl-1H-pyrazol-4-ylmethyl)-amine

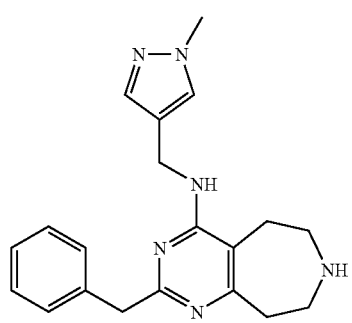

The ethyl ester of Preparation 23 (55 mg, 0.14 mmol) was dissolved in ethylene glycol (0.5 ml), treated with 10 M KOH (2.5 ml) and heated at reflux for 18 h. The reaction solution was poured into water (50 ml) and the product was extracted into CH₂Cl₂, dried over MgSO₄, concentrated and submitted to AP3 purification. LRMS APCI m/z 349 [MH]+.

Example 52

2-Benzyl-4-ethyl-6,7,8,9-tetrahydro-5H-pyrimido[4,5-d]azepine and 2-benzyl-4-ethyl-6,7,8,9-tetrahydro-5H-pyrimido[4,5-d]azepine hydrochloride

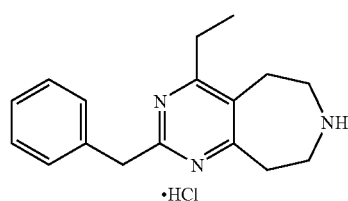

A suspension of the ethyl ester of Preparation 24 (96.0 mg, 0.28 mmol) in 4M hydrochloric acid (2.0 mL) was heated under reflux with stirring overnight. Concentrated hydrochloric acid (12M, 0.84 mL) and water (0.16 mL) was added in order to bring the concentration of the reaction mixture to 6M HCl and the mixture heated under reflux overnight. The reaction mixture was allowed to cool to room temperature, basified carefully with 1M sodium hydroxide (20 mL) and extracted with dichloromethane (3×10 mL). The combined extracts were dried over magnesium sulphate and evaporated in a vacuo to yield a yellow gum. Purification by flash column chromatography on silica (12 g) using the ISCO autopurification system with an eluant gradient of dichloromethane to 95:5:0.5 dichloromethane:methanol:ammonia afforded 2-benzyl-4-ethyl-6,7,8,9-tetrahydro-5H-pyrimido[4,5-d]azepine as a colourless oil in 65% yield, 49.0 mg. The free base was dissolved in dichloromethane (2.0 mL) and 2M hydrogen chloride in diethyl ether (2.0 mL) added. The resulting suspension was evaporated in vacuo and dried to afford the monohydrochloride salt as a white solid in 100% yield, 57 mg.
¹HNMR (400 MHz, CD₃OD) δ: 1.32 (t, 3H), 3.09 (q, 2H), 3.36 (m, 2H), 3.47 (m, 6H), 4.39 (s, 2H), 7.27 (m, 1H), 7.34 (t, 2H), 7.39 (d, 2H); LRMS APCI m/z 268 [MH]⁺

Example 53

2-Benzyl-4-cyclopropyl-6,7,8,9-tetrahydro-5H-pyrimido[4,5-d]azepine and 2-benzyl-4-cyclopropyl-6,7,8,9-tetrahydro-5H-pyrimido[4,5-d]azepine monohydrochloride

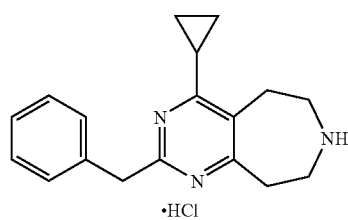

The title compounds were prepared according to the method of Example 52, starting from the product of Preparation 25 (94.0 mg, 0.27 mmol).

$^1$H NMR (400 MHz, CD$_3$OD) δ: 0.92 (m, 2H), 1.35 (m, 2H), 2.55 (m, 1H), 3.51 (m, 8H), 4.33 (s, 2H), 7.29 (m, 5H); LRMS APCI m/z 280 [MH]$^+$

Example 54A

2-Benzyl-6,7,8,9-tetrahydro-5H-pyrimido[4,5-d]azepine

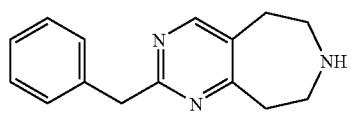

Benzyl 2-benzyl-4-chloro-5,6,8,9-tetrahydro-7H-pyrimido[4,5-d]azepine-7-carboxylate (5.00 g, 12.26 mmol) of Preparation 26, Step B, and Pd—C (250 mg) were added to ethanol (40 mL). The solution was stirred under and atmosphere of hydrogen at (50° C., 50 psi) for 4 h. The solution was then filtered through Arborcel and the solvent removed to give the crude HCl salt. The products were partitioned between 1M HCl (20 mL) and ethyl acetate (20 mL) and the ethyl acetate layer was discarded. The aqueous layer was basified with 2M NaOH and then extracted with ethyl acetate (3×30 mL). The organic layers were combined, washed with brine and dried over Na$_2$SO$_4$. The solvent removed under vacuum to give 1.945 g of 2-benzyl-6,7,8,9-tetrahydro-5H-pyrimido[4,5-d]azepine in 66% yield.

$^1$HNMR (400 MHz, DMSO) δ: 2.95-2.90 (m, 2H), 3.05-2.95 (m, 4H), 3.10-3.05 (m, 2H), 4.20 (s, 2H) 6.50 (1.5H, s), 7.20-7.15 (m, 1H), 7.30-7.10 (m, 4H), 8.40 (s, 1H); APCI m/z 240 [MH]$^+$

The title compound can also be prepared as described in Example 54B.

Example 54B

2-Benzyl-6,7,8,9-tetrahydro-5H-pyrimido[4,5-d]azepine

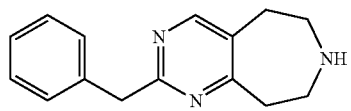

Step A

Benzyl 2-benzyl-4-oxo-3,4,5,6,8,9-hexahydro-7H-pyrimido[4,5-d]azepine-7-carboxylate

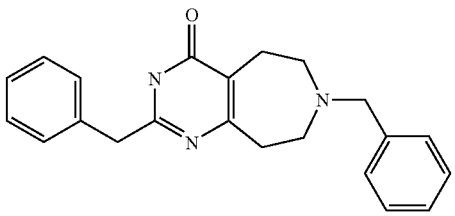

To a stirring slurry of N-(benzyloxycarbonyl)-4-piperidone (100.0 g, 0.429 mol) in tert-butylmethyl ether (700 ml) at −25° C. was added borontrifluoride diethyletherate (67.0 g, 58.3 ml, 0.472 mol, 1.1 eq) dropwise over 10 min, maintaining the temperature of the reaction below −20° C. On complete addition the mixture was stirred at −20° C. for 15 min. To this was added a solution of ethyl diazoacetate (63.6 g, 0.557 mol, 1.3 eq) in tert-butylmethyl ether (70 ml) dropwise over 60 min maintaining the temperature of the reaction below −20° C. On complete addition the mixture was stirred at −20° C. for 60 min. The reaction mixture was allowed to warm to 0° C. over 45 min, whereupon an aqueous solution of potassium carbonate (1M, 1070 ml, 2.5 mol) was added over 30 min, maintaining the temperature of the reaction between 0° C. and 10° C. The organic layer was separated and the solvent (400 ml) was removed by distillation under atmospheric pressure. Methanol (400 ml) was added and again the solvent (400 ml) was removed by distillation under atmospheric pressure, this step was repeated to leave a methanolic solution which was then added, dropwise, to a solution of sodium methoxide (69.5 g, 1.287 mol, 3.0 eq) in methanol (550 ml) at 25° C. The mixture was stirred at room temperature for 15 min then phenylacetamide hydrochloride (80.5 g, 0.472 mol, 1.1 eq) was added. The reaction mixture was stirred for 60 min. The solution was heated to reflux and 400 ml of solvent was distilled under atmospheric pressure. Ethyl acetate (400 ml) was added to the solution at reflux. The solution was heated back to reflux and 400 ml of solvent was distilled under atmospheric pressure. This was repeated. The reaction mixture was cooled to 60° C. and water (685 ml) was added, and the reaction mixture was stirred overnight. The resulting slurry was filtered, and the cake washed with cold ethyl acetate (3×100 ml). The solid was dried at 50° C. overnight to yield the desired product (136.9 g, 82%).

Step B

Benzyl 2-benzyl-4-chloro-5,6,8,9-tetrahydro-7H-pyrimido[4,5-d]azepine-7-carboxylate

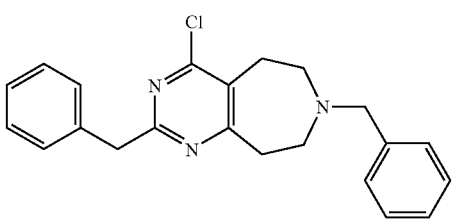

To a slurry of the compound from the previous step (25.0 g, 0.064 mol) in acetonitrile (500 ml) was added N,N-diisopropylethylamine (12.3 ml, 0.07 mol, 1.1 eq). To this was added phosphoryl chloride (47 ml, 0.524 mol, 8.0 eq) dropwise over 30 min. The resultant dark solution was heated to 70° C. and stirred for 60 min. The reaction mixture was cooled to 20° C. and concentrated to ~250 ml on rotaevaporator. To this was added acetonitrile (250 ml), and again the mixture was concentrated to ~250 ml on rotaevaporator (repeated twice). This mixture was then added dropwise to a stirred solution of 1M HCl (375 ml) and acetonitrile (125 ml), maintaining the temperature of the reaction mixture below 5° C. The resultant slurry was stirred at room temperature overnight, then at 5° C. for 2 h, before filtering. The cake was washed with a cold, premixed water/acetonitrile solution (2×100 ml), then dried at 50° C. overnight to give the desired product (21.2 g, 81%).

Step C

To a solution of the compound from the previous step (19.8 gm, 48.5 mmol) in ethanol (200 ml), was added triethylamine (13.5 ml, 97.1 mmol, 2.0 eq), followed by Pd/C (10% w/w, 2.0 gm). The reaction mixture was hydrogenated at 50 psi/50° C. overnight. The mixture was filtered over Arbocel and the cake washed with ethanol (2×50 ml). The solid was dried at 50° C. overnight to afford the title compound in quantitative yield (11.6 gm, 100%).

Example 54C

2-Benzyl-6,7,8,9-tetrahydro-5H-pyrimido[4,5-d] azepine, fumarate salt

The fumarate salt was prepared by warming a methanolic solution of the compound of Example 54A with 1 equivalent of fumaric acid. The hot solution was filtered and then allowed to cool to room temperature and crystals of the 0.75× (as determined by the integration of the peaks in the ¹HNMR spectrum) fumarate salt formed slowly. The fumarate salt can also be prepared as described in Example 54D.

Example 54D

2-Benzyl-6,7,8,9-tetrahydro-5H-pyrimido[4,5-d] azepine, fumarate salt

2-Benzyl-6,7,8,9-tetrahydro-5H-pyrimido[4,5-d]azepine (792 mg, 3.30 mmol) in hot ethyl acetate (35 ml) was added a solution of fumaric acid (1.0 eq, 384 mgs, 3.30 mmol) in hot methanol (12 ml). The resultant solution was stirred overnight. The solid was collected and recrystallised from ethyl acetate/methanol (30 ml/10 ml). The solid from this was collected by filtration then dried in vacuo to afford the title compound as a colourless solid (982 mg, 91%).

mp 205° C.

¹HNMR 400 MHz, DMSO$_{d6}$, δppm: 2.86-2.92 (m, 2H), 2.94-3.04 (m, 4H), 3.10-3.15 (m, 2H), 4.11 (s, 2H), 6.49 (s, 2H), 7.14-7.21 (m, 1H), 7.23-7.33 (m, 4H), 8.44 (s, 1H).

Example 54E

2-Benzyl-6,7,8,9-tetrahydro-5H-pyrimido[4,5-d] azepine hydrochloride

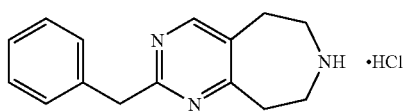

2-Benzyl-6,7,8,9-tetrahydro-5H-pyrimido[4,5-d]azepine of Example 54 (415 mg, 1.73 mmol) was dissolved in dioxane (5 ml) and treated with 4 M HCl in dioxane (1 ml) and stirred overnight. The dioxane was decanted off and the residue washed with ether and then dried in vacuo to give the pure product as a colourless solid. (430 mgs, 74.7%)

¹HNMR 400 MHz, DMSO$_{d6}$, δppm: 2.95-3.04 (m, 2H), 3.04-3.21 (m, 6H), 4.12 (s, 2H), 7.15-7.20 (m, 1H), 7.23-7.37 (m, 4H), 8.46 (s, 1H).

Example 54F (Crystallisation of Example 54E)

Single Crystal X-Ray Diffraction Experimental

The crystal structure was determined by Single Crystal X-Ray diffraction at room temperature and ambient relative humidity using a Bruker SMART APEX Single Crystal X-Ray diffractometer and Mo Kα radiation. Intensities were integrated (SMART v5.622 (control) and SAINT v6.02 (integration) software, Bruker AXS Inc., Madison, Wis. 1994) from several series of exposures where each exposure covered 0.3° in ω, with an exposure time of 60 s and the total data set was more than a sphere. Data were corrected for absorption using the multiscans method (SADABS, Program for scaling and correction of area detector data, G. M. Sheldrick, University of Göttingen, 1997 (based on the method of R. H. Blessing, Acta Cryst. 1995, A51, 33-38)).

The crystal structure was successfully solved by direct methods using SHELXS-97 (SHELXS-97, Program for crystal structure solution. G. M. Sheldrick, University of Göttingen, Germany, 1997, release 97-2), in Space Group P2$_1$/c and refined by the method of least-squares using SHELXL-97 (SHELXL-97, Program for crystal structure refinement. G. M. Sheldrick, University of Göttingen, Germany, 1997, release 97-2), to a final refined R-Factor of 7.30% (I>3σI).

Calculation of the Powder X-Ray Diffraction Pattern from the Crystal Structure

2θ angles and relative intensities (see Table below) were calculated from the single crystal structure of example 72 using the "Reflex Powder Diffraction" module of Accelrys MS Modelling™ [version 3.0]. Pertinent simulation parameters were:

Wavelength=1.5406 Å (Cu Kα)

Polarisation Factor=0.5

Pseudo-Voigt Profile (U=0.01, V=−0.001, W=0.002)

The calculated pattern represents that of a pure phase of example 72 since it is derived from a single crystal structure.

| 2θ (/°) | Relative Intensity (%) |
|---|---|
| 12.2 | 10.8 |
| 12.8 | 11.8 |
| 12.8 | 11.8 |
| 15.7 | 100 |
| 15.9 | 23.1 |
| 16.5 | 21.4 |
| 16.8 | 12.9 |
| 16.8 | 12.9 |
| 19.0 | 44.5 |
| 20.7 | 34.3 |
| 22.0 | 24.8 |
| 22.2 | 11 |
| 22.6 | 15.1 |
| 23.7 | 77.1 |
| 24.2 | 40.8 |
| 24.7 | 11.5 |
| 25.4 | 35.8 |
| 26.2 | 30.9 |
| 28.1 | 10.4 |
| 28.7 | 15.9 |
| 29.9 | 10 |
| 33.1 | 19.2 |
| 37.2 | 10.1 |

Example 55

2-Benzyl-4-imidazol-1-yl-6,7,8,9-tetrahydro-5H-pyrimido[4,5-d]azepine

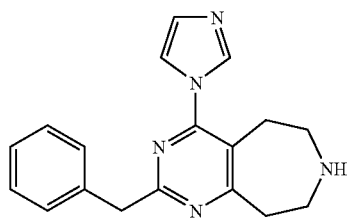

The product of Preparation 27 (130 μmol) was suspended in ethyl acetate (6 ml), 10% Pd/C (13 μmol) and 1-methyl-1, 4-cyclohexadiene were then added. The reaction mixture was heated at reflux for 2 h, filtered through a pad of Arbocel. The filter cake was washed with methanol. The filtrate was concentrated in vacuo to furnish 54 mg in 65% yield, which was submitted to AP3 purification. LRMS APCI m/z 306 [MH]+.

Example 56

2-(3-Chlorobenzyl)-6,7,8,9-tetrahydro-5H-pyrimido[4,5-d]azepine

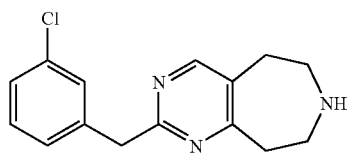

1,8-Bis-(dimethylamino)naphthalene (80 mg, 0.37 mmol) was added to a solution of 7-benzyl-2-(3-chlorobenzyl)-6,7,8,9-tetrahydro-5H-pyrimido[4,5-d]azepine of Preparation 28, Step C, (135 mg, 0.37 mmol) in dichloromethane (5 ml). Then 1-chloroethyl chloroformate (80.9 μl, 0.74 mmol) was added and stirred at room temperature for 16 h. The reaction mixture was diluted with dichloromethane (10 ml) then washed with 5% aqueous citric acid (15 ml). The organic phase was dried over magnesium sulphate and concentrated in vacuo. The residue was dissolved in methanol (5 ml) then heated to reflux, under nitrogen, for 1.5 h. The reaction mixture was concentrated in vacuo then the residue was partitioned between dichloromethane (10 ml) and 1N NaOH (10 ml). The organic phase was dried over magnesium sulphate and concentrated in vacuo. The residue was purified by column chromatography on silica gel, eluting with DCM:MeOH:0.880NH$_3$ (100:0:0 to 90:10:1), to afford the title compound as a yellow oil in 18% yield, 18 mg.

$^1$HNMR (400 MHz, CD$_3$OD) δ: 3.11 (m, 2H), 3.28 (m, 6H), 4.19 (s, 2H), 7.20-7.25 (m, 3H), 7.32 (m, 1H), 8.50 (s, 1H).

LRMS APCI m/z 274 [MH]+

Example 57

2-(4-Chlorobenzyl)-6,7,8,9-tetrahydro-5H-pyrimido[4,5-d]azepine

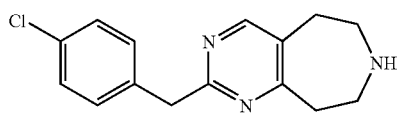

The title compound was obtained as a yellow oil in 26% yield, 13 mg, according to a similar method to that of Example 56, starting from 7-benzyl-2-(4-chlorobenzyl)-6,7,8,9-tetrahydro-5H-pyrimido[4,5-d]azepine of Preparation 29, Step B.

$^1$HNMR (400 MHz, CD$_3$OD) δ: 2.96 (m, 6H), 3.13 (m, 2H), 4.15 (s, 2H), 7.26 (m, 4H), 8.39 (s, 1H); LRMS APCI m/z 274 [MH]+

Example 58

2-(1-Phenylethyl)-6,7,8,9-tetrahydro-5H-pyrimido[4,5-d]azepine

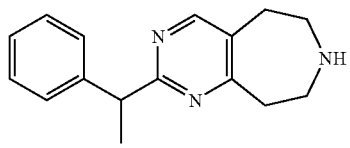

Palladium (10% on carbon) (40 mg) was added to a solution of 7-benzyl-4-chloro-2-(1-phenylethyl)-6,7,8,9-tetrahydro-5H-pyrimido[4,5-d]azepine (368 mg, 0.97 mmol) of Preparation 30, Step B, in ethyl acetate (5 ml) and hydrogenated at 50° C., 60 psi for 41 h. The reaction mixture was filtered through Arbocel then the filtrate was concentrated in vacuo. The residue was purified by HPLC (Phenomenex column, acetonitrile:water:formic acid gradient) to afford the title compound as an oil in 2% yield, 5 mg.

¹HNMR (400 MHz, CD₃OD) δ: 1.68 (d, 3H), 2.90 (m, 6H), 3.11 (m, 2H), 4.31 (q, 1H), 7.15 (m, 1H), 7.22 (m, 2H), 7.32 (m, 2H), 8.37 (s, 1H); LRMS ESCI m/z 254 [MH]⁺

Example 59

4-Ethoxy-2-(1-phenylethyl)-6,7,8,9-tetrahydro-5H-pyrimido[4,5-d]azepine

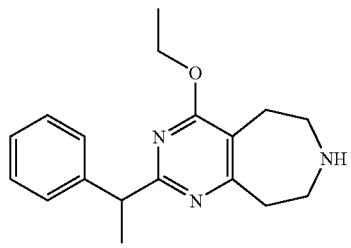

Palladium hydroxide (20% on carbon) (43 mg, 0.3 mmol) and 1-methyl-1,4-cyclohexadiene (3.42 ml, 30.5 mmol) was added to a solution of 7-benzyl-4-chloro-2-(1-phenylethyl)-6,7,8,9-tetrahydro-5H-pyrimido[4,5-d]azepine of preparation 30, Step B, (1.15 g, 3.04 mmol) in ethanol (30 ml) and refluxed, under nitrogen, for 16 h. The reaction mixture was filtered through Arbocel then the filtrate was concentrated in vacuo. The residue was purified by column chromatography on Biotage 40S cartridge, eluting with DCM:MeOH (100:0 to 90:10), to afford the title compound as a solid in 69% yield, 629 mg.

¹HNMR (400 MHz, CD₃OD) δ: 1.38 (t, 3H), 1.68 (d, 3H), 3.15 (m, 2H), 3.32 (m, 4H), 4.01 (m, 2H), 4.27 (q, 1H), 4.54 (q, 2H), 7.18 (m, 1H), 7.26 (m, 2H), 7.39 (m, 2H);
LRMS ESCI m/z 298 [MH]⁺

Example 60

2(2-Fluorobenzyl)-6,7,8,9-tetrahydro-5H-pyrimido[4,5-d]azepine

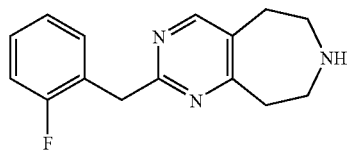

Ammonium formate (112 mg, 1.78 mmol) and 10% palladium on carbon (27 mg, 0.27 mmol) was added to a solution of 7-benzyl-4-chloro-2-(2-fluorobenzyl)-6,7,8,9-tetrahydro-5H-pyrimido[4,5-d]azepine the product of Preparation 31, Step B, (136 mg, 0.36 mmol) in methanol (12 ml) and heated to reflux for 5 h. The reaction mixture was filtered through Arbocel, the filtrate concentrated in vacuo and the residue purified by HPLC (Phenomenex column, acetonitrile:water: formic acid gradient) to afford the title compound as a colourless oil in 11.5% yield, 10.5 mg.

¹HNMR (400 MHz, CD₃OD) δ: 3.13 (m, 2H), 3.31 (m, 6H), 4.26 (s, 2H), 7.07 (m, 2H), 7.26 (m, 2H), 8.49 (s, 1H). LRMS APCI m/z 258 [MH]⁺

Example 61

2-(3-Fluorobenzyl)-6,7,8,9-tetrahydro-5H-pyrimido[4,5-d]azepine

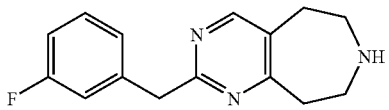

The title compound was prepared according to a similar method to that of Example 60, starting from 7-benzyl-4-chloro-2-(3-fluorobenzyl)-6,7,8,9-tetrahydro-5H-pyrimido[4,5-d]azepine of Preparation 32, Step B, except that the reaction was heated to reflux for 48 h. The title compound was obtained as a colourless oil in 7.8% yield, 8.2 mg.

¹HNMR (400 MHz, CD₃OD) δ: 3.12 (m, 2H), 3.31 (m, 6H), 4.21 (s, 2H), 7.06 (m, 2H), 7.25 (m, 2H), 8.52 (s, 1H). LRMS APCI m/z 258 [MH]⁺

Example 62

2-(4-Fluorobenzyl)-6,7,8,9-tetrahydro-5H-pyrimido[4,5-d]azepine

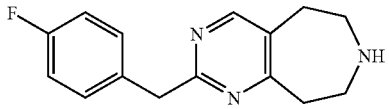

The title compound was obtained by a similar method to that of Example 60, starting from 7-benzyl-4-chloro-2-(4-fluorobenzyl)-6,7,8,9-tetrahydro-5H-pyrimido[4,5-d]azepine of Preparation 33, Step B, as a colourless oil in 27% yield, 38 mg, except that the reaction was heated to reflux for 48 h and purification was carried out on a 2 g silica cartridge eluting with DCM:MeOH:0.880NH₃ (100:0:0 to 90:10:1).

¹HNMR (400 MHz, CD₃OD) δ: 3.02 (m, 2H), 3.23 (m, 6H), 4.16 (s, 2H), 6.97 (m, 2H), 7.30 (m, 2H), 8.45 (s, 1H). LRMS APCI m/z 258 [MH]⁺

Example 63

2-[3-(Trifluoromethyl)benzyl]-6,7,8,9-tetrahydro-5H-pyrimido[4,5-d]azepine

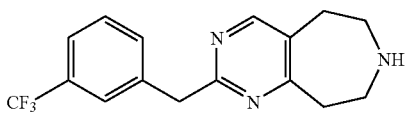

The title compound was obtained by a similar method to that of Example 60, starting from 7-benzyl-4-chloro-2-[3-(trifluoromethyl)benzyl]-6,7,8,9-tetrahydro-5H-pyrimido[4,5-d]azepine of Preparation 34, Step B, except that the reaction was heated to reflux for 17 h and was purified on a 5 g silica cartridge eluting with DCM:MeOH:NH₃ (100:0:0 to 90:10:1), yielding a colourless oil in 17% yield, 26 mg.

¹HNMR (400 MHz, CD₃OD) δ: 2.93 (m, 6H), 3.14 (m, 2H), 4.25 (s, 2H), 7.45-7.62 (m, 4H), 8.40 (s, 1H).

LRMS APCI m/z 308 [MH]⁺

Example 64

2-(4-Methylbenzyl)-6,7,8,9-tetrahydro-5H-pyrimido[4,5-d]azepine

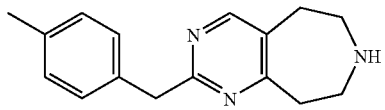

Under nitrogen, a mixture of 7-benzyl-4-chloro-2-(4-methylbenzyl)-6,7,8,9-tetrahydro-5H-pyrimido[4,5-d]azepine of Preparation 35, Step B, (150 mg, 0.40 mmol), ammonium formate (250 mg, 4.0 mmol) and 20% palladium on charcoal (15 mg) in ethanol (5 ml) was heated at 75° C. for 1 h. After returning to room temperature, the mixture was filtered through a pad of Arbocel, washing the pad with ethanol. The combined eluates were concentrated in vacuo and the residue purified by column chromatography on silica gel, eluting with dichloromethane:methanol:0.880NH3, 95:5:0.5 then 90:10:1, to afford the title compound as an oil in 85% yield, 85 mg.

¹HNMR (400 MHz, CD₃OD) δ: 2.27 (s, 3H), 2.90 (m, 4H), 2.95 (m, 2H), 3.12 (m, 2H), 4.11 (s, 2H), 7.07 (d, 2H), 7.15 (d, 2H), 8.38 (s, 1H); LRMS m/z 254 [MH]⁺

Example 65

2-(3-Methylbenzyl)-6,7,8,9-tetrahydro-5H-pyrimido[4,5-d]azepine

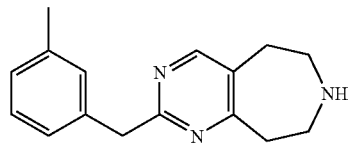

The title compound was obtained as a white solid in 24% yield, 56 mg, by a similar method to that of Example 64, starting from 7-benzyl-4-chloro-2-(3-methylbenzyl)-6,7,8,9-tetrahydro-5H-pyrimido[4,5-d]azepine of Preparation 36, Step B.

¹HNMR (400 MHz, CD₃OD) δ: 2.28 (s, 3H), 2.90 (m, 4H), 2.94 (m, 2H), 3.12 (m, 2H), 4.12 (s, 2H), 6.99-7.15 (m, 4H), 8.38 (s, 1H); LRMS m/z 254 [MH]⁺

Example 66

2-(2-Methylbenzyl)-6,7,8,9-tetrahydro-5H-pyrimido[4,5-d]azepine

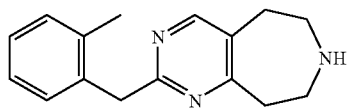

The title compound was obtained by a similar method to that of Example 64, starting from 7-benzyl-4-chloro-2-(2-methylbenzyl)-6,7,8,9-tetrahydro-5H-pyrimido[4,5-d] azepine of Preparation 37, Step B. The residue was purified by column chromatography on silica gel, eluting with ethyl acetate:methanol:0.880NH3, 90:10:1 to 80:20:2, to afford the title compound as an oil in 87% yield, 85 mg.

¹HNMR (400 MHz, CD₃OD) δ: 2.31 (s, 3H), 2.91 (m, 4H), 2.94 (m, 2H), 3.10 (m, 2H), 4.20 (s, 2H), 7.05-7.14 (m, 4H), 8.36 (s, 1H); LRMS m/z 254 [MH]⁺

Example 67

2-Benzyl-4-methoxy-6,7,8,9-tetrahydro-5H-pyrimido[4,5-d]azepine

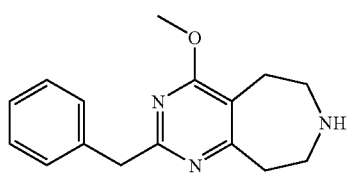

2,7-Dibenzyl-4-methoxy-6,7,8,9-tetrahydro-5H-pyrimido[4,5-d]azepine of Preparation 38, Step C, (75 mg, 0.2 mmol) was dissolved in 10 ml of methanol and ammonium formate (66 mg, 1.04 mmol) and 10% palladium on carbon (20 mg) was added. The reaction was refluxed under nitrogen for 2 h. The reaction mixture was filtered through Arbocel and concentrated in vacuo. The residue was purified by column chromatography on Biotage 40S cartridge, eluting with DCM:MeOH:0.880NH₃ (95:5:0.5 to 90:10:1), to afford the title compound as a colourless oil in 100% yield, 56 mg.

¹HNMR (400 MHz, CD₃OD) δ: 2.90 (m, 6H), 3.04 (t, 2H), 3.94 (s, 3H), 4.05 (s, 2H), 7.17 (t, 1H), 7.25 (t, 2H), 7.32 (d, 2H); LRMS APCI m/z 270 [MH]⁺

Example 68

2-Benzyl-4-methyl-6,7,8,9-tetrahydro-5H-pyrimido[4,5-d]azepine

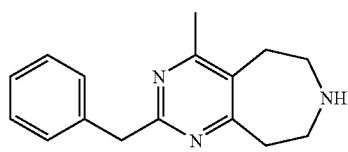

The title compound was prepared according to a similar method to that of Example 64, except that 10% palladium on carbon was used, starting from 2,7-dibenzyl-4-methyl-6,7,8,9-tetrahydro-5H-pyrimido[4,5-d]azepine of Preparation 39, and obtained as a pale yellow solid in 90% yield (44 mg).

¹HNMR (400 MHz, CD₃OD) δ: 2.50 (s, 3H), 2.94 (m, 6H), 3.09 (t, 2H), 4.11(s, 2H), 7.15-7.28 (m, 5H); LRMS ESI m/z 254 [MH]⁺

Example 69

2-Benzyl-4-butyl-6,7,8,9-tetrahydro-5H-pyrimido[4,5-d]azepine

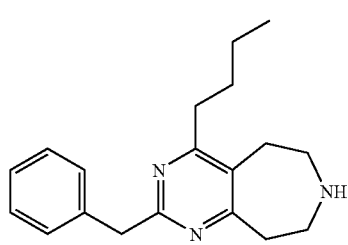

The title compound was prepared according to a similar method to that of Example 68, starting from 2,7-dibenzyl-4-butyl-6,7,8,9-tetrahydro-5H-pyrimido[4,5-d]azepine of Preparation 40, and obtained as a yellow oil in 99% yield (94 mg).

¹HNMR (400 MHz, CD₃OD) δ: 0.94 (t, 3H), 1.39 (m, 2H), 1.59 (m, 2H), 2.8o (t, 2H), 2.92 (m, 4H), 2.97 (m, 2H), 3.08 (m, 2H), 4.13 (s, 2H), 7.16 (t, 1H), 7.26 (m, 4H); LRMS ESI m/z 296 [MH]⁺

Example 70

Phenyl-(6,7,8,9-tetrahydro-5H-pyrimido[4,5-d]azepin-2-yl)-methanol dihydrochloride (Stereoisomer 1)

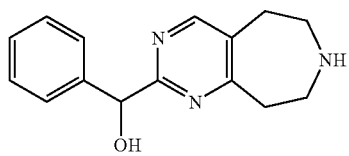

A similar method to that of Example 4, starting from stereoisomer 1, 2-(hydroxy-phenyl-methyl)-5,6,8,9-tetrahydropyrimido[4,5-d]azepine-7-carboxylic acid Tert-butyl ester of preparation 41, furnished 22 mg of the title compound in 99% yield.

¹H-NMR (400 MHz, DMSO-d₆) δ: 3.04 (m, 2H), 3.22 (m, 2H), 3.48 (m, 4H), 5.71 (s, 1H), 7.20 (m, 1H), 7.28 (m, 2H), 7.43 (m, 2H), 8.54 (s, 1H), 9.22 (s, 2H); LRMS ESI m/z 256 [MH]+.

Example 71

Phenyl-(6,7,8,9-tetrahydro-5H-pyrimido[4,5-d]azepin-2-yl)-methanol dihydrochloride (Stereoisomer 2)

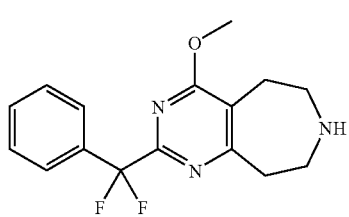

A similar method to that of Example 4, starting from stereoisomer 2, 2-(hydroxy-phenyl-methyl)-5,6,8,9-tetrahydropyrimido[4,5-d]azepine-7-carboxylic acid Tert-butyl ester of preparation 41, furnished 2 mg of the title compound in 80% yield.

¹H-NMR (400 MHz, DMSO-d₆) δ: 3.04 (m, 2H), 3.22 (m, 2H), 3.48 (m, 4H), 5.71 (s, 1H), 7.20 (m, 1H), 7.28 (m, 2H), 7.43 (m, 2H), 8.54 (s, 1H), 9.22 (s, 2H); LRMS ESI m/z 256 [MH]+.

Example 72

2-(Difluoro-phenyl-methyl)-4-methoxy-6,7,8,9-tetrahydro-5H-pyrimido[4,5-d]azepine To a solution of tert-butyl 2-[difluoro(phenyl)methyl]-4-oxo-3,4,5,6,8,9-hexahydro-7H-pyrimido[4,5-d]azepine-7-carboxylate of Preparation 8, Step A (535 mg, 1.37 mmol) was added trimethyloxonium tetrafluoroborate (3 eq, 606 mgs 4.10 mmol) and the reaction mixture was stirred overnight at room temperature, after which time an orange solid had precipitated. The reaction mixture was quenched with saturated NaHCO₃ (aq) and stirred rapidly until a complete solution was attained. The organic layer was collected, dried over MgSO4, filtered and dried in vacuo to give a brown oil. This material was chromatographed on silica, eluting with ethyl acetate/10% methanol, then dichloromethane/methanol/ammonia, 95/5/0.5. The relevant fractions were combined and evaporated in vacuo to give a coloured oil (quantitative yield).

¹HNMR 400 MHz, CDCl₃, δppm: 2.85-3.01 (m, 6H), 3.10-3.16 (m, 2H), 3.95 (s, 3H), 7.38-7.41 (m, 3H), 7.66-7.73 (m, 2H).

LCMS Rt=2.07 min; ES+ m/z 306 [MH]⁺.

Example 72A 2-(Difluoro-phenyl-methyl)-4-methoxy-6,7,8,9-tetrahydro-5H-pyrimido[4,5-d]azepine hydrochloride

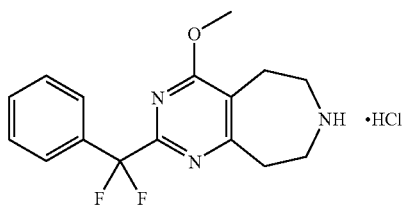

The product from Example 73 was dissolved in diethyl ether and 1N HCl in diethyl ether was added, causing the precipitation of a colourless solid. This was collected and dried in vacuo to afford the title compound (162 mg, 34%).

¹HNMR 400 MHz, DMSO_{d6}, δppm: 3.04-3.09 (m, 2H), 3.18-3.27 (m, 6H), 3.93 (s, 3H), 7.44-7.52 (m, 3H), 7.57-7.63 (m, 2H), 9.18 (bs, 2H).

LCMS Rt=2.07 min; ES+ m/z 306 [MH]⁺.

Examples 73 to 86

The compounds of the general formula

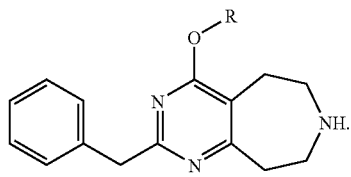

were prepared using either of the methods described below.

Method 1

To a solution of the chloride of Preparation 26, Step B (0.1 mmol) in dioxan (1.5 ml) was added ROH (0.1 mmol, 1.0 eq). To this was then added KOH (0.2 mmol, 2.0 eq) and the reaction was stirred at 100° C. overnight. The reaction mixture was filtered and the solvent removed by Speedvac. The crude product was taken on to the deprotection step without further purification.

Method 2

An 8 ml vial was charged with ROH (0.1 mmol). To a separate flask a solution of the chloride of Preparation 26, Step B (0.1 mmol) in THF, was added NaH (1.2 eq, 0.12 mmol). This was stirred together for 10 min before being added to the vial. The reaction mixture was then stirred at 60° C. overnight. The solvent was removed and water (2 ml) was added. The mixture was extracted with ethyl acetate (2×1 ml), concentrated, and the crude product was taken on to the deprotection step without further purification.

Deprotection

To each product obtained according to method 1 or method 2 was added ethyl acetate (2 ml). 1-methyl-1,4-cyclohexadiene (0.11 ml, 1 mmol, 10 eq) was added and nitrogen bubbled through the solution for 10 min. Pd/C (3 mg) was added and the reaction mixture was heated at reflux for 4 h. The solution was cooled to room temperature, filtered through celite, washing with ethyl acetate (2×1 ml). The solvent was removed by Speedvac, and the final compound was purified by preparative HPLC. All compounds were isolated as trifluoroacetic acid salts. The following conditions were used for all examples: mobile phase A—0.075% TFA in water (v/v), mobile phase B—0.075% TFA in acetonitrile (v/v). HPLC columns either, A: Ymc ODS-AQ 75×30 mm (examples 74-81 and 83-86) or B: Ymc ODS-AQ 250×21.2 mm (example 82).

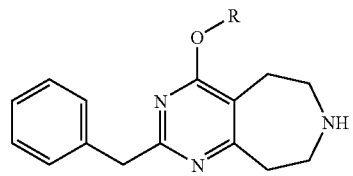

| Ex. No. | R | Data | Name |
|---|---|---|---|
| 73 | <br>N-shaped pyridinylethyl group | LCMS Rt = 2.04 min; ES+ m/z 361 [MH]⁺. | 2-benzyl-4-(2-pyridin-2-ylethoxy)-6,7,8,9-tetrahydro-5H-pyrimido[4,5-d]azepine |

-continued

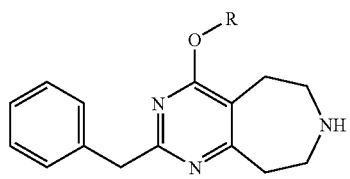

| Ex. No. | R | Data | Name |
|---|---|---|---|
| 74 | tetrahydrofuran-2-ylmethyl | LCMS Rt = 2.4 min; ES+ m/z 340 [MH]+. | 2-benzyl-4-(2-tetrahydrofuran-2-ylmethoxy)-6,7,8,9-tetrahydro-5H-pyrimido[4,5-d]azepine |
| 75 | 4-cyanophenethyl | LCMS Rt = 2.34 min; ES+ m/z 385 [MH]+. | 4-{2-[(2-benzyl-6,7,8,9-tetrahydro-5H-pyrimido-[4,5-d]azepin-4-yl)oxy]ethyl}-benzonitrile |
| 76 | isobutyl | LCMS Rt = 2.19 min; ES+ m/z 312 [MH]+. | 2-benzyl-4-isobutoxy-6,7,8,9-tetrahydro-5H-pyrimido[4,5-d]azepine |
| 77 | (2-methylpyridin-3-yl)methyl | LCMS Rt = 1.98 min; ES+ m/z 361 [MH]+. | 2-benzyl-4-[(2-methyl-pyridin-3-yl)methoxy]-6,7,8,9-tetrahydro-5H-pyrimido[4,5-d]azepine |
| 78 | (2S)-1-methylpyrrolidin-2-ylmethyl | LCMS Rt = 1.99 min; ES+ m/z 353 [MH]+. | 2-benzyl-4-{[(2S)-1-methylpyrrolidin-2-yl]methoxy}-6,7,8,9-tetrahydro-5H-pyrimido[4,5-d]azepine |
| 79 | 2-(pyridin-4-yl)ethyl | LCMS Rt = 1.95 min | 2-benzyl-4-(2-pyridin-4-ylethoxy)-6,7,8,9-tetrahydro-5H-pyrimido[4,5-d]azepine |
| 80 | tetrahydro-2H-pyran-4-ylmethyl | LCMS Rt = 2.41 min; ES+ m/z 354 [MH]+. | 2-benzyl-4-(tetrahydro-2H-pyran-4-ylmethoxy)-6,7,8,9-tetrahydro-5H-pyrimido[4,5-d]azepine |
| 81 | 2-tert-butoxyethyl | LCMS Rt = 2.34 min; ES+ m/z 356 [MH]+ | 2-benzyl-4-(2-tert-butoxyethoxy)-6,7,8,9-tetrahydro-5H-pyrimido[4,5-d]azepine |
| 82 | 1-methyl-2-morpholin-4-ylethyl | LCMS Rt = 2.00 min; ES+ m/z 383 [MH]+ | 2-benzyl-4-(1-methyl-2-morpholin-4-ylethoxy)-6,7,8,9-tetrahydro-5H-pyrimido[4,5-d]azepine |
| 83 | 2-(dimethylamino)propyl | LCMS Rt = 1.85 min | 1-[(2-benzyl-6,7,8,9-tetrahydro-5H-pyrimido-[4,5-d]azepin-4-yl)oxy]-N,N-dimethylpropan-2-amine |
| 84 | 4,4,4-trifluorobutyl | LCMS Rt = 2.29 min; ES+ m/z 366 [MH]+ | 2-benzyl-4-(4,4,4-trifluorobutoxy)-6,7,8,9-tetrahydro-5H-pyrimido[4,5-d]azepine |

-continued

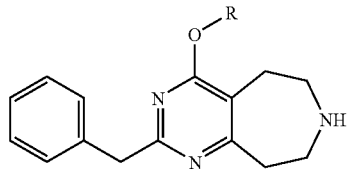

| Ex. No. | R | Data | Name |
|---|---|---|---|
| 85 | (1-methylpiperidin-4-yl)methyl | LCMS Rt = 1.99 min | 2-benzyl-4-[(1-methyl-piperidin-4-yl)methoxy]-6,7,8,9-tetrahydro-5H-pyrimido[4,5-d]azepine |
| 86 | (4-methoxyphenyl)methyl | | 2-benzyl-4-(4-methoxyphenylmethoxy)-6,7,8,9-tetrahydro-5H-pyrimido[4,5-d]azepine |

Examples 87 to 113

The compounds of the general formula

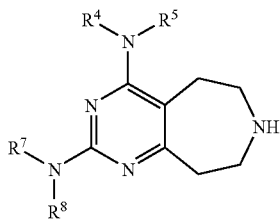

were prepared using the method described below a) To a solution of the product of Preparation 42, Step B (1.0 g) in THF (10 ml) was added $R^4R^5NH$ (1.2 eq). To this was added potassium carbonate (1.1 gm, 3.0 eq). The reaction was shaken at 80° C. for 16 h. Crude products were concentrated by Speedvac and purified by column chromatography, eluting with DCM/methanol (30/1), to give a pure product of formula:

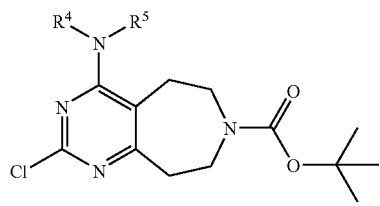

b) To a solution of the product of step a) (75 μmol) in toluene (1 ml) was added sodium tert-butoxide (20.1 mg, 90 μmol, 1.2 eq). To this was then added sequentially, $R^7R^8NH$ (90 μmol, 1.2 eq), $Pd_2dba_3$ (12.9 mg, 15 μmol, 0.2 eq) and BINAP (8.1 mg, 15 μmol, 0.2 eq). The reaction was shaken at 100° C. for 16 h. The cooled reaction was filtered and concentrated by Speedvac. The residues were purified by preparative HPLC to give the desired product of formula:

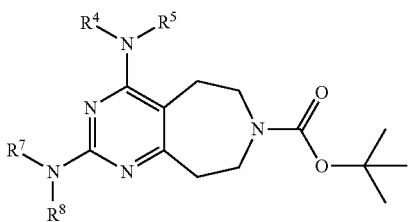

HPLC conditions: Mobile phase A- 0.075% TFA in water (v/v), Mobile phase B- 0.075% TFA in acetonitrile (v/v). HPLC columns either, A: Ymc ODS-AQ 75×30 mm (examples 87-88, 90-91, 94-96, 98, 100-102, 107-108, 110-112), Ymc ODS-AQ 250×21.2 mm (examples 89, 92-93, 97, 99, 103-104, 106, 109), or C: Fuji C18 300×25 mm (example 105).

c) The product from step b) was dissolved in DCM (1.0 ml), and to this was added a mixture of TFA/DCM (1:7 v/v, 1.5 ml) and the reaction mixture was stirred for 3 h. Without further purification, the final product was obtained after concentration by Speedvac.

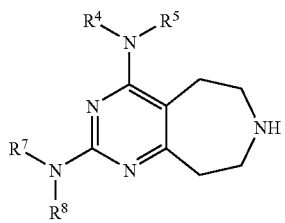

| Ex No. | NR⁴R⁵ | NR⁷R⁸ | Data | Name |
|---|---|---|---|---|
| 87 | HN–ethyl | 1,2,3,4-tetrahydroisoquinolin-2-yl | LCMS Rt = 2.83 min; ES+ m/z 324 [MH]⁺. | 2-(3,4-dihydroisoquinolin-2(1H)-yl)-N-ethyl-6,7,8,9-tetrahydro-5H-pyrimido-[4,5-d]azepin-4-amine |
| 88 | thiomorpholin-4-yl | 1,2,3,4-tetrahydroisoquinolin-2-yl | LCMS Rt = 2.01 min; ES+ m/z 382 [MH]⁺. | 2-(3,4-dihydroisoquinolin-2(1H)-yl)-4-thiomorpholin-4-yl-6,7,8,9-tetrahydro-5H-pyrimido[4,5-d]-azepin-4-amine |
| 89 | HN–butyl | thiomorpholin-4-yl | LCMS Rt = 2.90 min; ES+ m/z 322 [MH]⁺. | N-butyl-2-thiomorpholin-4-yl-6,7,8,9-tetrahydro-5H-pyrimido[4,5-d]-azepin-4-amine |
| 90 | N(CH₃)(CH₂-cyclopropyl) | thiomorpholin-4-yl | LCMS Rt = 2.95 min; ES+ m/z 334 [MH]⁺. | N-(cyclopropylmethyl)-N-methyl-2-thiomorpholin-4-yl-6,7,8,9-tetrahydro-5H-pyrimido[4,5-d]azepin-4-amine |
| 91 | HN–CH₂CH₂Ph | thiomorpholin-4-yl | LCMS Rt = 3.07 min; ES+ m/z 370 [MH]⁺. | N-(2-phenylethyl)-2-thiomorpholin-4-yl-6,7,8,9-tetrahydro-5H-pyrimido-[4,5-d]azepin-4-amine |
| 92 | N(CH₃)(ethyl) | thiomorpholin-4-yl | LCMS Rt = 2.74 min; ES+ m/z 308 [MH]⁺. | N-ethyl-N-methyl-2-thiomorpholin-4-yl-6,7,8,9-tetrahydro-5H-pyrimido-[4,5-d]azepin-4-amine |
| 93 | NH(CH₃) | thiomorpholin-4-yl | LCMS Rt = 2.40 min; ES+ m/z 250 [MH]⁺. | N-methyl-2-thio-morpholin-4-yl-6,7,8,9-tetrahydro-5H-pyrimido-[4,5-d]azepin-4-amine |
| 94 | thiomorpholin-4-yl | thiomorpholin-4-yl | LCMS Rt = 1.95 min; ES+ m/z 352 [MH]⁺. | 2,4-dithiomorpholin-4-yl-6,7,8,9-tetrahydro-5H-pyrimido[4,5-d]azepine |
| 95 | N(CH₃)(ethyl) | morpholin-4-yl | LCMS Rt = 2.32 min; ES+ m/z 292 [MH]⁺. | N-ethyl-N-methyl-2-morpholin-4-yl-6,7,8,9-tetrahydro-5H-pyrimido-[4,5-d]azepin-4-amine |
| 96 | thiomorpholin-4-yl | morpholin-4-yl | LCMS Rt = 1.71 min; ES+ m/z 336 [MH]⁺. | 2-morpholin-4-yl-4-thio-morpholin-4-yl-6,7,8,9-tetrahydro-5H-pyrimido-[4,5-d]azepin-4-amine |
| 97 | N(CH₃)₂ | morpholin-4-yl | LCMS Rt = 2.16 min; ES+ m/z 278 [MH]⁺. | N,N-dimethyl-2-morpholin-4-yl-6,7,8,9-tetrahydro-5H-pyrimido-[4,5-d]azepin-4-amine |
| 98 | HN–ethyl | N(CH₃)(ethyl) | LCMS Rt = 2.41 min; ES+ m/z 250 [MH]⁺. | N-2,N-4-diethyl-N-2-methyl-6,7,8,9-tetrahydro-5H-pyrimido[4,5-d]-azepin-4-amine |

-continued

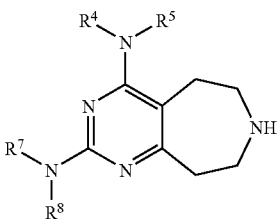

| Ex No. | NR⁴R⁵ | NR⁷R⁸ | Data | Name |
|---|---|---|---|---|
| 99 | cyclopropylmethyl-NH- | -N(Et)(Me) | LCMS Rt = 2.58 min; ES+ m/z 276 [MH]⁺. | N-4-(cyclopropylmethyl)-N-2-ethyl-N-2-methyl-6,7,8,9-tetrahydro-5H-pyrimido[4,5-d]azepine-4-amine |
| 100 | -N(Me)(Me) | -N(Et)(Me) | LCMS Rt = 2.51 min; ES+ m/z 250 [MH]⁺. | N-2-ethyl-N-2,N-4,N-4-trimethyl-6,7,8,9-tetrahydro-5H-pyrimido-[4,5-d]azepine-2,4-diamine |
| 101 | isobutyl-NH- | -N(Et)(Me) | LCMS Rt = 2.81 min; ES+ m/z 278 [MH]⁺. | N-2-ethyl-N-4-isobutyl-N-2-methyl-6,7,8,9-tetrahydro-5H-pyrimido[4,5-d]azepine-2,4-diamine |
| 102 | Me-NH- | -N(Et)(Me) | LCMS Rt = 2.24 min; ES+ m/z 236 [MH]⁺. | N-2-ethyl-N-2,N-4-dimethyl-6,7,8,9-tetrahydro-5H-pyrimido[4,5-d]-azepine-2,4-diamine |
| 103 | propyl-NH- | -N(CH₂-cyclopropyl)(Me) | LCMS Rt = 2.85 min; ES+ m/z 290 [MH]⁺. | N-2-(cyclopropylmethyl)-N-2-methyl-N-4-propyl-6,7,8,9-tetrahydro-5H-pyrimido[4,5-d]azepine-2,4-diamine |
| 104 | -N(Me)(Me) | -N(CH₂-cyclopropyl)(Me) | LCMS Rt = 2.75 min; ES+ m/z 276 [MH]⁺. | N-2-(cyclopropylmethyl)-N-2,N-4,N-4-trimethyl-6,7,8,9-tetrahydro-5H-pyrimido[4,5-d]azepine-2,4-diamine |
| 105 | morpholin-4-yl | -N(CH₂Ph)(Me) | LCMS Rt = 3.06 min; ES+ m/z 354 [MH]⁺. | N-benzyl-N-methyl-4-morpholin-4-yl-6,7,8,9-tetrahydro-5H-pyrimido-[4,5-d]azepin-2-amine |
| 106 | thiomorpholin-4-yl | pyrrolidin-1-yl | LCMS Rt = 2.75 min; ES+ m/z 320 [MH]⁺. | 2-pyrrolodin-1-yl-4-thiomorpholin-4-yl-6,7,8,9-tetrahydro-5H-pyrimido[4,5-d]azepine |
| 107 | -N(Me)(Me) | -N(Me)(Me) | LCMS Rt = 2.18 min; ES+ m/z 236 [MH]⁺. | N,N,N',N'-tetramethyl-6,7,8,9-tetrahydro-5H-pyrimido[4,5-d]azepine-2,4-diamine |
| 108 | benzyl-NH- | azetidin-1-yl | LCMS Rt = 2.59 min; ES+ m/z 310 [MH]⁺. | 2-azetidin-1-yl-N-benzyl-6,7,8,9-tetrahydro-5H-pyrimido[4,5-d]azepine-4-amine |
| 109 | thiomorpholin-4-yl | cyclopropyl-NH- | LCMS Rt = 2.35 min; ES+ m/z 306 [MH]⁺. | N-cyclopropyl-4-thiomorpholin-4-yl-6,7,8,9-tetrahydro-5H-pyrimido-[4,5-d]azepin-2-amine |
| 110 | thiomorpholin-4-yl | 2-phenylethyl-NH- | LCMS Rt = 1.99 min; ES+ m/z 370 [MH]⁺. | N-(2-phenylethyl)-4-thiomorpholin-4-yl-6,7,8,9-tetrahydro-5H-pyrimido[4,5-d]azepine-2-amine |

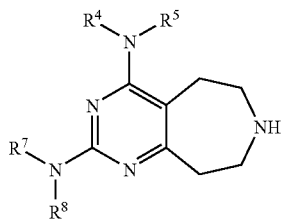

| Ex No. | NR⁴R⁵ | NR⁷R⁸ | Data | Name |
|---|---|---|---|---|
| 111 | thiomorpholin-4-yl | HN-propyl | LCMS Rt = 2.62 min; ES+ m/z 308 [MH]⁺. | N-propyl-4-thiomorpholin-4-yl-6,7,8,9-tetrahydro-5H-pyrimido[4,5-d]-azepin-2-amine |
| 112 | N-methyl-N-(cyclopropylmethyl) | HN-ethyl | LCMS Rt = 2.55 min; ES+ m/z 276 [MH]⁺. | N-4-(cyclopropylmethyl)-N-2-ethyl-N-4-methyl-6,7,8,9-tetrahydro-5H-pyrimido[4,5-d]azepine-2,4-diamine |
| 113 | N,N-dimethyl | N-methyl-N-benzyl | LCMS Rt = 3.06 min; ES+ m/z 312 [MH]⁺. | N-2-benzyl-N,2-N,4-N,4-trimethyl-6,7,8,9-tetrahydro-5H-pyrimido[4,5-d]azepine-2,4-diamine |

Preparations

The following Preparations illustrate the synthesis of certain intermediates used in the preparation of the preceding Examples.

Preparation 1

Step A

Tert-butyl 2-benzyl-4-oxo-5,6,8,9-tetrahydro-7H-pyrimido[4,5-d]azepine-7-carboxylate

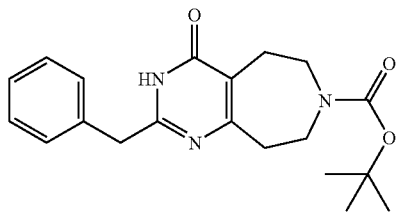

1-Tert-butyl 4-ethyl 5-oxoazepane-1,4-dicarboxylate (See WO2006029154, example 1a, p 34) (1.32 g, 4.6 mmol) and 2-phenyl-acetamidine (750 mg, 4.4 mmol) were added to a solution of NaOMe (3.8M, 3.5 mL, 13.2 mmol) in MeOH (15.0 mL) at 0° C. and stirred at 0° C. to room temperature overnight. The reaction was quenched with water, partitioned with ethyl acetate and the phases separated. The combined organics layer were dried over magnesium sulfate, filtered and concentrated in vacuo to provide the crude product as an orange gum. The residue was purified by flash column chromatography eluting with CH$_2$Cl$_2$:ethyl acetate (90:10 to 70:30) to afford the title compound as a white solid (1.30 g, 83% yield).

¹H NMR (400 MHz, CDCl$_3$) δ: 1.48 (s, 9H); 2.83-2.92 (m, 2H); 2.92-3.01 (m, 2H); 3.48-3.65 (m, 4H); 3.95 (s, 2H); 7.25-7.39 (m, 5H). LCMS Rt=2.76 min; ES+ m/z 355 [MH]⁺.

Step B

Tert-butyl 2-benzyl-4-{[(trifluoromethyl)sulfonyl]oxy}-5,6,8,9-tetrahydro-7H-pyrimido[4,5-d]azepine-7-carboxylate

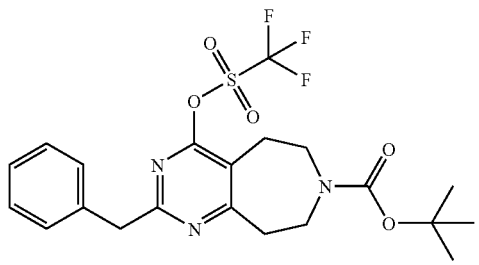

Triflic anhydride (516 mg, 0.30 mL, 1.83 mmol) was added dropwise to a solution of the product of Step A (500 mg, 1.41 mmol) and pyridine (167 mg, 0.17 mL, 2.11 mmol) in CH$_2$Cl$_2$ (5.0 mL) at 0° C. The resulting solution was allowed to warm to room temperature and stirred for 1 h. The reaction mixture was quenched by addition of water then partitioned between 5% citric acid and ethyl acetate. The organic layer was washed with sodium bicarbonate (sat.), dried over magnesium sulfate and concentrated under vacuum to yield the crude product as a yellow gum (670 mg). This material was taken on without further purification.

LCMS Rt=3.86 min; ES+ AP+ m/z 432 [MH-tBu]⁺.

¹H NMR (400 MHz, CDCl$_3$) δ: 1.45 (s, 9H), 2.89 (m, 2H), 3.18 (m, 2H), 3.62 (m, 4H), 4.19 (s, 2H), 6.97 (d, 2H), 7.28 (t, 1H), 7.39 (d, 2H). LRMS APCI m/z 432 [M-$^t$BuH]⁺

Preparation 2
Step A:

2-Phenylpropanimidamide

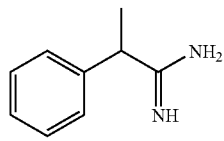

Ammonium chloride (535 mg, 10.0 mmol) was suspended in toluene (3 ml), cooled to 0° C., under nitrogen then trimethylaluminium (5 ml, 2M in toluene) was added dropwise. The reaction mixture was warmed to room temperature and stirred for 2 h. Then 2-phenylpropionitrile (1.33 ml, 10.0 mmol) in toluene (2 ml) was added and heated to 80° C. for 17 h. The reaction mixture was poured onto a slurry of silica (20 g) in dichloromethane (20 ml) and stirred for 5 min. It was filtered and the filtrate concentrated in vacuo. Trituration of the residue with diethyl ether afforded the title compound as a solid in 95% yield, 1.75 g.

$^1$HNMR (400 MHz, CD$_3$OD) δ: 1.64 (t, 3H), 4.00 (q, 1H), 7.33 (m, 5H)

Step B:

Tert-butyl 4-oxo-2-(1-phenylethyl)-3,4,5,6,8,9-hexahydro-7H-pyrimido[4,5-d]azepine-7-carboxylate

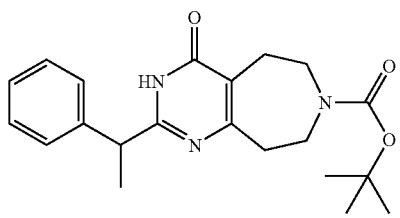

The title compound was prepared by a similar method to that of Preparation 1, Step A, starting from 2-phenylpropanimidamide of Step A. The title compound was obtained as a white solid (780 mg, 91% yield).

$^1$H NMR (400 MHZ, CDCl$_3$) δ: 1.46 (s, 9H); 1.65 (d, 3H); 2.80-3.05 (m, 4H); 3.45-3.75 (m, 4H); 4.05 (q, 1H); 7.21-7.40 (m, 5H). LCMS Rt=3.11 min; ES+ m/z 370 [MH]$^+$.

Step C:

Tert-butyl 2-(1-phenylethyl)-4-{[(trifluoromethyl)sulfonyl]oxy}-5,6,8,9-tetrahydro-7H-pyrimido[4,5-d]azepine-7-carboxylate

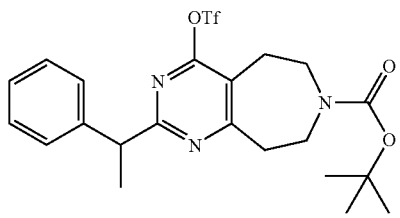

A similar method to that of Preparation 1, Step B, was used to afford the crude product as a yellow gum (410 mg). This material was taken on to subsequent reactions without further purification.

LCMS Rt=4.04 min; ES+ m/z 446 [MH-tBu]$^+$

Step D:

Tert-butyl 2-(1-phenylethyl)-5,6,8,9-tetrahydro-7H-pyrimido[4,5-d]azepine-7-carboxylate

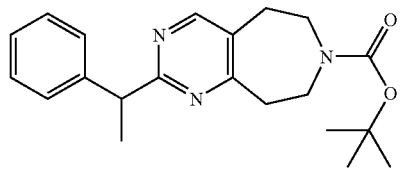

Palladium acetate (2.7 mg, 0.012 mmol), 1,1'-Bis(diphenylphosphino)ferrocene) (13 mg, 0.024 mmol), triethylamine (182 mg, 0.25 mL, 1.80 mmol) and formic acid (55 mg, 0.05 mL, 1.20 mmol) were added to a solution of the triflate of Step B (300 mg, 0.60 mmol) in DMF (4.0 mL) and the reaction mixture was warmed to 50° C. for 2 h with stirring, to give a ~70:30 mixture of the corresponding pyrimidinone:to the title compound. Water (10 mL) was added and products extracted with diethyl ether (2×10 mL). The combined organics were washed with brine, dried over magnesium sulfate, filtered and the solvent evaporated in vacuo to provide crude product residue as a yellow gum (165 mg). The crude material was purified by flash column chromatography eluting with CH$_2$Cl$_2$:ethyl acetate (100:0 to 70:30) to provide the title compound as a white solid (137 mg, 65% yield).

$^1$H NMR (400 MHZ, CDCl$_3$) δ: 1.48 (s, 9H); 1.73 (d, 3H); 2.80 (bs, 2H); 3.10 (bs, 2H); 3.59 (bs, 4H); 4.39 (q, 1H); 7.16-7.22 (m, 1H); 7.23-7.32 (m, 2H); 7.37-7.44 (m, 2H).

LCMS Rt=3.41 min; ES+ m/z 354 [MH]$^+$.

Preparation 3

Tert-butyl 4-(methylamino)-2-(1-phenylethyl)-5,6,8,9-tetrahydro-7H-pyrimido[4,5-d]azepine-7-carboxylate

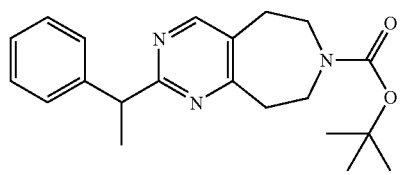

A solution of methylamine (2.0M, 0.65 mL, 1.30 mmol) was added to a solution of Tert-butyl 2-(1-phenylethyl)-4-{[(trifluoromethyl)sulfonyl]oxy}-5,6,8,9-tetrahydro-7H-pyrimido[4,5-d]azepine-7-carboxylate of preparation 2, step B (130 mg, 0.26 mmol) in MeCN (4.0 mL) at room temperature with stirring. The mixture was stirred at room temperature for 20 h. The solvent was evaporated in vacuo to provide the crude title compound as a yellow gum. The crude material was purified by flash column chromatography eluting with CH$_2$Cl$_2$:ethyl acetate (100:0 to 50:50) to yield the desired product as a white crystalline solid (89 mg, 90% yield).

Preparation 4
Step A:

2-Benzyl-4-(2,4,6-trimethyl-benzenesulfonyloxy)-5,6,8,9-tetrahydro-pyrimido[4,5-d]azepine-7-carboxylic acid Tert-butyl ester

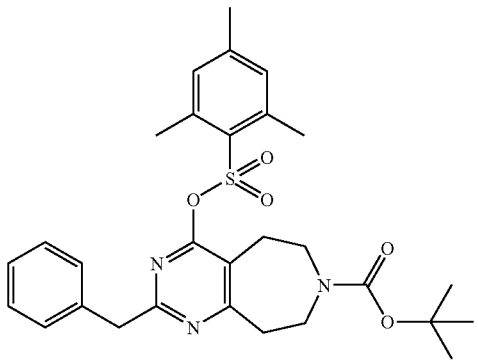

A solution of pyrimidinone of preparation 1, step A (1.00 g, 2.81 mmol) and 2,4,6-trimethylbenzenesulfonyl chloride (0.677 g, 3.09 mmol) in dichloromethane (18 ml) was treated with triethylamine (1.56 ml, 11.3 mmol) and N,N-dimethylaminopyridine (34 mg, 0.28 mmol) and stirred at room temperature for 2 h. The solution was poured into 50 ml of dichloromethane, washed twice with 5% citric acid aq. dried over solid MgSO$_4$, filtered and concentrated in vacuo to give the crude product. The resulting solid was dissolved in hot ethyl acetate (25 ml), cooled to room temperature and treated with n-heptane (25 ml) which caused a white solid to form. The solid was collected by filtration and dried to give the title compound (1.02 g, 67% yield).

$^1$H-NMR (400 MHz, DMSO-d$_6$) δ: 1.48 (s, 9H) 2.36 (s, 3H) 2.65 (s, 6H) 2.99 (m, 2H) 3.10 (m, 2H) 3.59 (m, 4H) 3.92 (s, 2H) 6.99 (m, 4H) 7.15 (m, 3H); LRMS APCI m/z 482 [M-tBu]+.

Step B:

(R,S)-2-Benzyl-4-(2-methyl-pyrrolidin-1-yl)-5,6,8,9-tetrahydro-pyrimido[4,5-d]azepine-7-carboxylic acid Tert-butyl ester

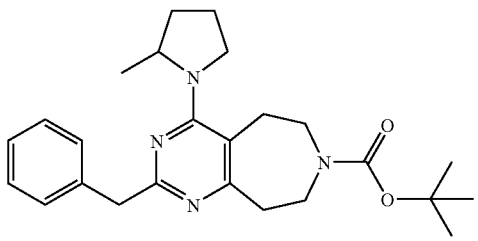

A solution of the product from step A (100 mg, 0.186 mmol) and (R,S)-2-methylpyrrolidine (90 µl, 0.93 mmol) in N,N-dimethylacetamide (2.6 ml) was stirred for 18 h at room temperature. The solvent was removed in vacuo and the residue was dissolved in ethyl acetate (25 ml), washed thrice with sat. aq. NH$_4$Cl, dried over MgSO$_4$, filtered and concentrated to give the crude product which was purified by silica gel column chromatography eluting from 20 to 100% ethyl acetate/CyH to give to give the title compound (77 mg, 98% yield).

$^1$H-NMR (400 MHz, MeOH-d$_4$) δ: 1.14 (d, 3H), 1.37 (s, 9H) 1.57 (m, 1H), 1.68 (m, 1H), 1.95 (m, 1H), 2.12 (m, 1H), 2.80 (ddd, 1H), 2.94 (ddd, 1H), 2.97 (m, 2H), 3.33 (m, 1H), 3.45 (m, 1H), 3.61 (m, 2H), 3.68 (m, 1H), 3.74 (dt, 1H), 3.95 (dd, 2H), 4.32 (m, 1H), 7.15 (m, 1H), 7.23 (t, 2H), 7.30 (m, 2H); LRMS APCI m/z 423 [MH]+.

Preparation 5
Step A:

2-(4-Fluorophenyl)ethanimidamide

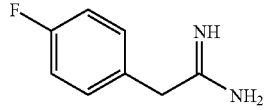

The title compound was prepared by a similar method to that of 2-Phenylpropanimidamide and was obtained as a colourless solid (552 mg, 98%).

$^1$HNMR 400 MHz CDCl$_3$ δ: 3.72 (s, 2H), 7.08 (t, 2H), 7.31 (dd, 2H)

Step B:

Tert-butyl 2-(4-fluorobenzyl)-4-oxo-3,4,5,6,8,9-hexahydro-7H-pyrimido[4,5,d]azepine-7-carboxylate

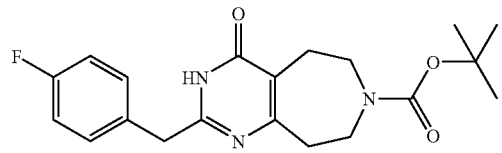

The title compound was prepared by a method similar to Preparation 1, Step A, starting from 2-(4-fluorophenyl)ethanimidamide from step A (373 mg, 2.45 mmol). The residue was columned on an ISCO Combiflash 12 gm cartridge, eluting with DCM/2% MeOH. The relevant fractions were combined and concentrated in vacuo to leave a beige solid. (597 mg, 65%)

$^1$HNMR 400 MHz CDCl$_3$ δ: 1.49 (s, 9H), 2.91 (bd, 4H), 3.57 (bd, 4H), 3.90 (s, 2H), 6.98 (t, 2H), 7.36 (dd, 2H). LRMS ES+ and AP+ m/z 374 [MH]$^+$.

Step C:

Tert-butyl 2-(4-fluorobenzyl)-4-[(trifluoromethylsulfonyl)oxy]-5,6,8,9-tetrahydro-7H-pyrimido[4,5,d]azepine-7-carboxylate

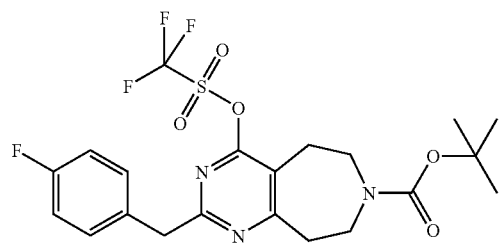

The title compound was prepared by a similar method to that of Preparation 1, Step B, starting from Tert-butyl 2-(4-fluorobenzyl)-4-oxo-3,4,5,6,8,9-hexahydro-7H-pyrimido[4,5,d]azepine-7-carboxylate of Step B, except that lutidine was used instead of pyridine. A white solid. (270 mg, 99%) was obtained after concentration of the organic layer after work-up.

$^1$HNMR 400 MHz CDCl$_3$ δ: 1.48 (s, 9H), 2.92 (dd, 2H), 3.17 (dd, 2H), 3.56-3.66 (m, 4H), 4.14 (s, 2H), 6.98 (t, 2H), 7.33 (dd, 2H). LRMS ES+ and AP+ m/z 506 [MH]$^+$.

Step D:

Tert-butyl 2-(4-fluorobenzyl)-4-(methylamino)-5,6,8,9-tetrahydro-7H-pyrimido[4,5,d]azepine-7-carboxylate

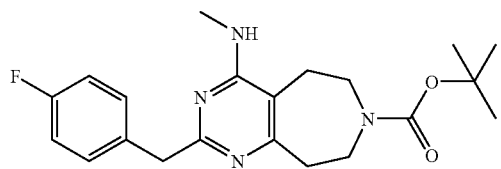

To a solution of the triflate from Step C (90.0 mg, 0.18 mmol) in DMA (2 mL) was added methylamine solution in THF (0.45 mL, 2.0M, 0.89 mmol) and the reaction was stirred for 48 h. The reaction mixture was concentrated in vacuo and the material was used without further purification. A quantitative yield was assumed. LRMS ES+ and AP+ m/z 387 [MH]$^+$.

Preparation 6

Tert-butyl 4-(dimethylamino)-2-(4-fluorobenzyl)-5,6,8,9-tetrahydro-7H-pyrimido[4,5,d]azepine-7-carboxylate

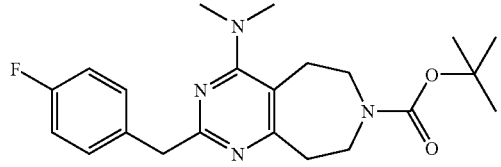

The title compound was prepared by a similar method to that of Preparation 5, Step D starting from the product of Preparation 5, Step C and dimethylamine. A quantitative yield was assumed.

LRMS ES+ and AP+ m/z 401 [MH]$^+$.

Preparation 7

Tert-butyl 2-(4-fluorobenzyl)-4-pyrrolidin-1-yl-5,6,8,9-tetrahydro-7H-pyrimido[4,5,d]azepine-7-carboxylate

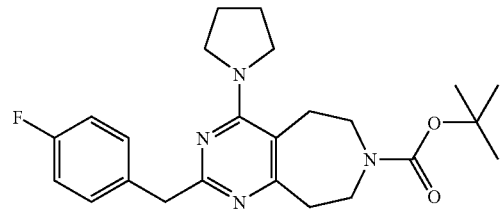

To a solution of the product of Preparation 5, Step C (90.0 mg, 0.18 mmol) in DMA (2 mL) was added pyrrolidine (0.074 mL, 0.89 mmol) and the reaction was stirred for 48 h. The reaction mixture was concentrated in vacuo and the material was used without further purification. Assume 100% yield. LRMS ES+ and AP+ m/z 427 [MH]$^+$.

Preparation 8
Step A

Tert-butyl 2-[difluoro(phenyl)methyl]-4-oxo-3,4,5,6,8,9-hexahydro-7H-pyrimido[4,5-d]azepine-7-carboxylate

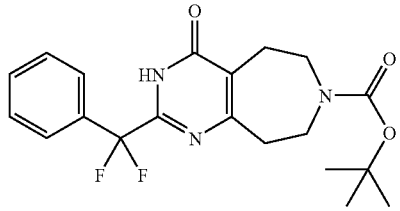

The title compound was prepared by a similar method to that of Preparation 1, Step A, starting from 2,2-difluoro-2-phenylethanimidamide. The title compound was obtained as a white solid (226 mg, 20% yield).

$^1$H NMR (400 MHZ, CDCl$_3$) δ: 1.42 (s, 9H); 2.83-2.92 (m, 2H); 2.92-2.99 (m, 2H); 3.48-3.61 (m, 4H); 7.22-7.51 (m, 3H); 7.61 (d, 2H). LCMS Rt=3.06 min; ES− m/z 391 [M]$^−$; ES+ m/z 336 [MH-tBu]$^+$.

Step B:

Tert-butyl 2-[difluoro(phenyl)methyl]-4-{[(trifluoromethyl)sulfonyl]oxy}-5,6,8,9-tetrahydro-7H-pyrimido[4,5-d]azepine-7-carboxylate

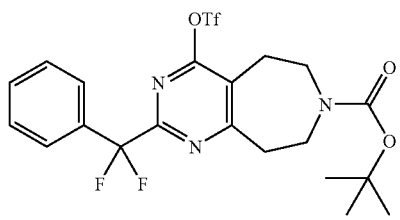

A similar method to that of Preparation 1, Step B was used to afford the crude product as a yellow gum (67 mg), starting from the product of Step A. This material was taken on without further purification.

LCMS Rt=3.86 min; ES+ AP+ m/z 468 [MH-tBu]$^+$.

Step C

Tert-butyl 2-[difluoro(phenyl)methyl]-4-(methylamino)-5,6,8,9-tetrahydro-7H-pyrimido[4,5-d]azepine-7-carboxylate

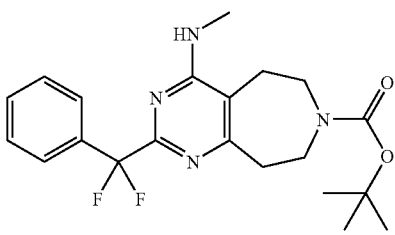

A similar method to that of Preparation 5, Step D was used to afford the crude product as a brown gum (50 mg), starting from the product of Step B. This material was taken on without further purification.

LCMS Rt=3.19 min; ES+ AP+ m/z 405 [MH]+.

Preparation 9
Step A

Tert-butyl 2-(1-methyl-1-phenylethyl)-4-oxo-3,4,5,6,8,9-hexahydro-7H-pyrimido[4,5-d]azepine-7-carboxylate

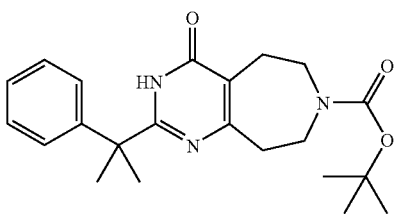

The title compound was prepared by a similar method to that of Preparation 1, Step A, starting from 2-methyl-2-phenylpropanimidamide. The title compound was obtained as a white solid (280 mg, 64% yield).

$^1$H NMR (400 MHZ, CDCl$_3$) δ: 1.48 (s, 9H); 1.67 (s, 6H); 2.80-2.86 (m, 2H); 2.98-3.07 (m, 2H); 3.53-3.60 (m, 2H); 3.61-3.66 (m, 2H). LRMS ES+ and AP+ m/z 384 [MH]+.

LCMS Rt=3.25 min; ES+ m/z 383 [MH]+.

Step B

Tert-butyl 2-(1-methyl-1-phenylethyl)-4-{[(trifluoromethyl)sulfonyl]oxy}-5,6,8,9-tetrahydro-7H-pyrimido[4,5-d]azepine-7-carboxylate

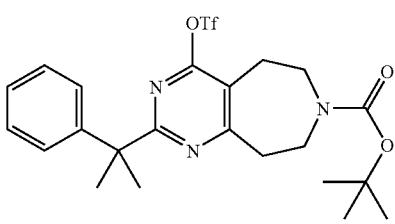

The title compound was prepared by a similar method to that of Preparation 5, Step D, starting from the product of step A. The crude product was obtained as a yellow gum (270 mg, ~100% yield which was taken on without further purification.

$^1$H NMR (400 MHZ, CDCl$_3$) δ: 1.45 (s, 9H), 1.79 (s, 6H), 2.90-2.96 (m, 2H), 3.13-3.21 (m, 2H), 3.58-3.65 (m, 4H), 7.15-7.36 (m, 5H). LRMS ES+ and AP+ m/z 516 [MH]+.

LCMS Rt=4.18 min; AP+ m/z 516 [MH]+.

Preparation 10

Tert-butyl 2-(1-methyl-1-phenylethyl)-5,6,8,9-tetrahydro-7H-pyrimido[4,5-d]azepine-7-carboxylate

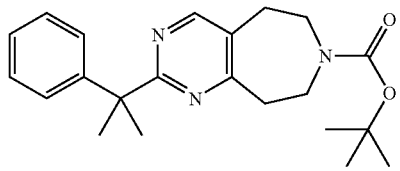

The title compound was prepared by a similar method to that of Preparation 2, Step D, starting from tert-butyl 2-(1-methyl-1-phenylethyl)-4-{[(trifluoromethyl)sulfonyl]oxy}-5,6,8,9-tetrahydro-7H-pyrimido[4,5-d]azepine-7-carboxylate of Preparation 9, Step B. The title compound was obtained as a colourless solid (12 mg, 34% yield).

$^1$H NMR (400 MHZ, CDCl$_3$) δ: 1.45 (s, 9H), 1.79 (s, 6H), 2.75-2.85 (m, 2H), 3.05-3.15 (m, 2H), 3.55-3.65 (m, 4H), 7.15-7.35 (m, 5H), 8.37 (s, 1H). LCMS Rt=3.69 min; ES+ AP+ m/z 368 [MH]+.

Preparation 11

Tert-butyl 4-(methylamino)-2-(1-methyl-1-phenylethyl)-5,6,8,9-tetrahydro-7H-pyrimido[4,5-d]azepine-7-carboxylate

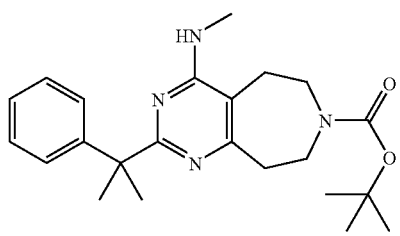

A similar method to that of Preparation 5, Step D, starting from tert-butyl 2-(1-methyl-1-phenylethyl)-4-{[(trifluoromethyl)sulfonyl]oxy}-5,6,8,9-tetrahydro-7H-pyrimido[4,5-d]azepine-7-carboxylate of Preparation 9, Step B, was used to afford the crude title compound as a brown gum (40 mg). The material was used in subsequent reactions without further purification.

$^1$H NMR (400 MHZ, CDCl$_3$) δ: 1.42 (s, 9H); 1.79 (s, 6H); 2.58-2.65 (m, 2H); 2.95-2.16 (m, 2H); 3.55-3.75 (m, 4H); 7.16-7.21 (m, 5H). LCMS Rt=2.33 min; ES+ AP+ m/z 397 [MH]+.

Preparation 12

Tert-butyl 2-(1-methyl-1-phenylethyl)-4-morpholin-4-yl-5,6,8,9-tetrahydro-7H-pyrimido[4,5-d]azepine-7-carboxylate

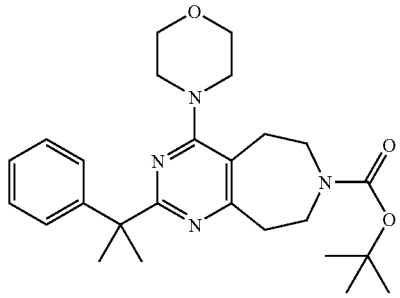

A similar method to that of Preparation 5, Step D, starting from tert-butyl 2-(1-methyl-1-phenylethyl)-4-{[(trifluoromethyl)sulfonyl]oxy}-5,6,8,9-tetrahydro-7H-pyrimido[4,5-d]azepine-7-carboxylate of Preparation 9, Step B, was used to afford the crude title compound as a brown gum (45 mg). The material was used in subsequent reactions without further purification.

LCMS Rt=2.70 min; ES+ m/z 453 [MH]+.

Preparation 13

Tert-butyl 2-(1-methyl-1-phenylethyl)-4-pyrrolidin-1-yl-5,6,8,9-tetrahydro-7H-pyrimido[4,5-d]azepine-7-carboxylate

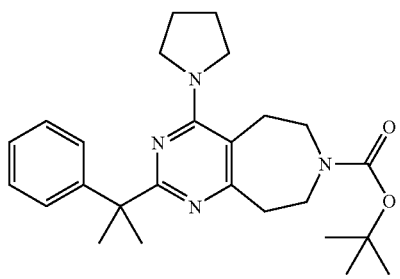

A similar method to that of Preparation 5, Step D, starting from tert-butyl 2-(1-methyl-1-phenylethyl)-4-{[(trifluoromethyl)sulfonyl]oxy}-5,6,8,9-tetrahydro-7H-pyrimido[4,5-d]azepine-7-carboxylate of Preparation 9, Step B, was used to afford the crude title compound as a brown gum (45 mg). The material was used in subsequent reactions without further purification.

LCMS Rt=2.53 min; ES+ AP+ m/z 438 [MH]+.

Preparation 14
Step A

Tert-butyl 2-(1-phenylcyclopropyl)-4-oxo-3,4,5,6,8,9-hexahydro-7H-pyrimido[4,5-d]azepine-7-carboxylate

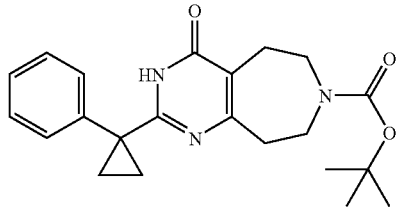

A similar method to that of Preparation 1, Step A, starting from 1-phenylcyclopropanecarboximidamide was used to afford the title compound a white solid (291 mg, 57% yield).
$^1$H NMR (400 MHZ, CDCl$_3$) δ: 1.32-1.38 (m, 2H); 1.48 (s, 9H); 1.77-1.81 (m, 2H); 2.78-2.92 (m, 4H); 3.46-3.68 (m, 4H); 7.37-7.45 (m, 5H). LCMS Rt=3.16 min; ES+ m/z 382 [MH]+

Step B

Tert-butyl 2-(1-phenylcyclopropyl)-4-{[(trifluoromethyl)sulfonyl]oxy}-5,6,8,9-tetrahydro-7H-pyrimido[4,5-d]azepine-7-carboxylate

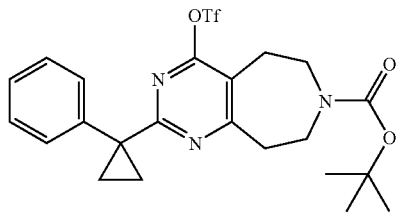

The title compound was prepared by a similar method to that of Preparation 1, Step B, starting from tert-butyl 2-(1-phenylcyclopropyl)-4-oxo-3,4,5,6,8,9-hexahydro-7H-pyrimido[4,5-d]azepine-7-carboxylate of Step A. The crude product was obtained as a yellow gum (86 mg) which was taken on without further purification.
$^1$H NMR (400 MHZ, CDCl$_3$) δ: 1.38-1.43 (m, 2H), 1.45 (s, 9H), 1.71 (m, 2H), 2.80-2.96 (m, 2H), 3.03-3.11 (m, 2H), 3.45-3.65 (m, 4H), 7.22-7.40 (m, 5H). LCMS Rt=2.00 min; AP+ m/z 514 [MH]+.

Preparation 15

Tert-butyl 4-morpholin-4-yl-2-(1-phenylcyclopropyl)-5,6,8,9-tetrahydro-7H-pyrimido[4,5-d]azepine-7-carboxylate

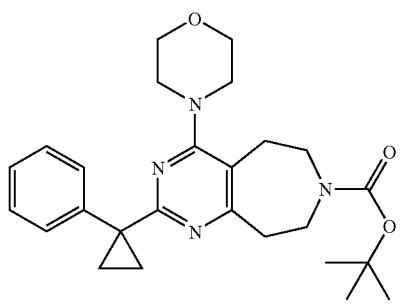

A similar method to that of Preparation 5, Step D, starting from tert-butyl 2-(1-phenylcyclopropyl)-4-{[(trifluoromethyl)sulfonyl]oxy}-5,6,8,9-tetrahydro-7H-pyrimido[4,5-d] azepine-7-carboxylate of Preparation 14, Step B, was used to afford the crude title compound as a brown gum (80 mg), which was used in subsequent reactions without further purification.

LRMS ES+ AP+ m/z 451 [MH]+. LCMS Rt=2.57 min; ES+ AP+ m/z 451 [MH]+.

Preparation 16
Step A

Tert-butyl 2-[benzyl(methyl)amino]-4-oxo-3,4,5,6,8,9-hexahydro-7H-pyrimido[4,5,d]azepine-7-carboxylate

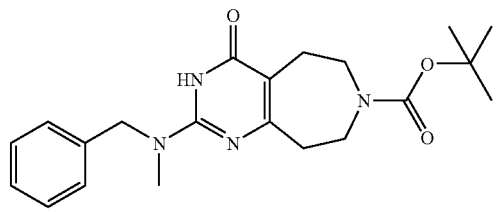

The title compound was prepared by a similar method to that of Preparation 1, Step A, starting from 1-benzyl-1methylguanidine. The title compound was obtained as an off-white solid. (544 mg, 92%).

Step B

Tert-butyl 2-[benzyl(methyl)amino]-4-([{trifluoromethyl)sulfonyl]oxy}-5,6,8,9-tetrahydro-7H-pyrimido[4,5,d]azepine-7-carboxylate

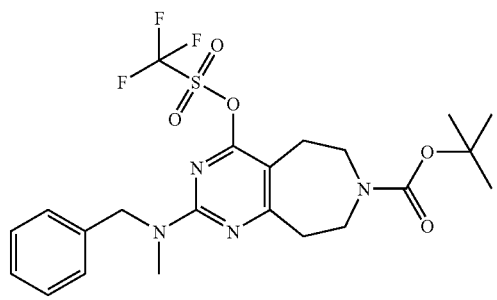

The title compound was prepared using a similar method to that of Preparation 1, Step B, starting from the product of step A, except that no pyridine was used. Concentration of the organic layer left a reddish oil which was used without further purification. (100% yield assumed).

LRMS AP+ m/z 517 [MH]+.

Step C

Tert-butyl 2-[benzyl(methyl)amino]-4-(dimethylamino)-5,6,8,9-tetrahydro-7H-pyrimido[4,5,d]azepine-7-carboxylate

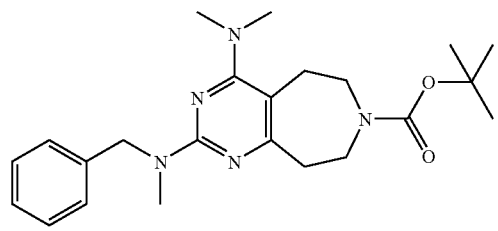

A similar method to that of Preparation 5, Step D, starting from tert-butyl 2-[benzyl(methyl)amino]-4-([{trifluoromethyl)sulfonyl]oxy}-5,6,8,9-tetrahydro-7H-pyrimido[4,5,d] azepine-7-carboxylate of Preparation 16, Step B, was used to afford the crude title compound as an off-white solid. (64 mg, 100% yield assumed). The material was used in subsequent reactions without further purification.

LRMS ES+ and AP+ m/z 412 [MH]+

Preparation 17

Tert-butyl 2-[benzyl(methyl)amino]-4-morpholin-4-yl-5,6,8,9-tetrahydro-7H-pyrinnido[4,5,d]azepine-7-carboxylate

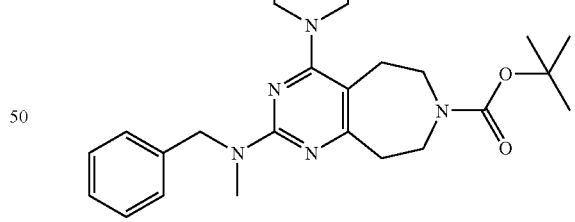

A similar method to that of Preparation 5, Step D, starting from tert-butyl 2-[benzyl(methyl)amino]-4-([{trifluoromethyl)sulfonyl]oxy}-5,6,8,9-tetrahydro-7H-pyrimido[4,5,d] azepine-7-carboxylate of Preparation 16, Step B, was used to afford the crude title compound as an off-white solid. (78 mg, assume 100% yield). The material was used in subsequent reactions without further purification LRMS ES+ and AP+ m/z 454 [MH]+

Preparation 18

Tert-butyl 2-[benzyl(methyl)amino]-4-methoxy-5,6,8,9-tetrahydro-7H-pyrimido[4,5,d]azepine-7-carboxylate

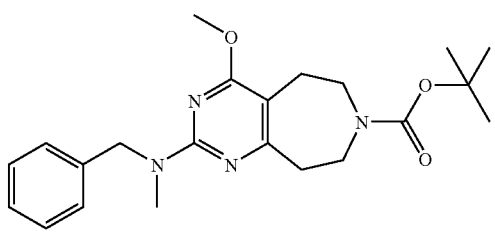

To a solution of tert-butyl 2-[benzyl(methyl)amino]-4-oxo-3,4,5,6,8,9-hexahydro-7H-pyrimido[4,5,d]azepine-7-carboxylate of Preparation 16, Step A (70 mg, 0.19 mmol) in DCM (2 ml) was added trimethyloxonium tetrafluoroborate (3 eq., 84.1 mg, 0.57 mmol) and the mixture was stirred for 2 h. The combined organic layers were combined, dried over MgSO$_4$, filtered and concentrated in vacuo. The residue was purified by column chromatography eluting with ethyl actate/pentane (1:3 to 1:1). The relevant fractions were combined and concentrated in vacuo to afford the title compound as a colourless oil (31 mg, 41% yield).

$^1$HNMR 400 MHz CDCl$_3$ δ: 1.49 (s, 9H), 2.75 (dd, 2H), 2.90 (dd, 2H), 3.10 (s, 3H), 3.46-3.62 (m, 4H), 3.85 (s, 3H), 4.86 (s, 2H), 7.21-7.32 (m, 5H). LRMS ES+ m/z 399 [MH]$^+$.

Preparation 19
Step A

1-Tert-butyl 4-ethyl 6-methyl-5-oxoazepane-1,4-dicarboxylate

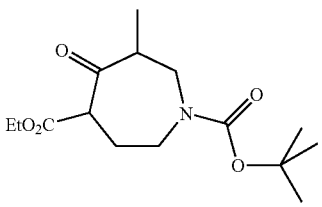

The title compound was prepared by a similar method to that of 1-tert-butyl 4-ethyl 5-oxoazepane-1,4-dicarboxylate (see WO2006029154, example 1a, p 34) from Tert-butyl 3-methyl-4-oxopiperidine-1-carboxylate, yielding 100% of title compound which was taken on for pyrimidone formation without further purification.

LRMS APCI m/z 244 [M-$^t$BuH]$^+$

Step B

Tert-butyl 2-benzyl-9-methyl-4-oxo-3,4,5,6,8,9-hexahydro-7H-pyrimido[4,5-d]azepine-7-carboxylate

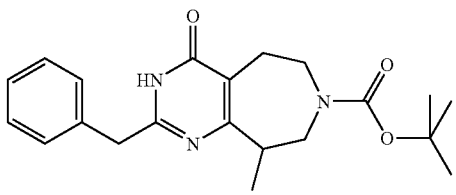

The title compound was prepared by a similar method to that of Preparation 1, Step A, starting from 1-tert-butyl 4-ethyl 6-methyl-5-oxoazepane-1,4-dicarboxylate and 2-phenyl-acetamidine, yielding 70% of title compound.

$^1$H NMR (400 MHz, CDCl$_3$) δ: 1.26 (d, 3H), 1.43 (s, 9H), 2.79 (m, 1H), 3.15 (m, 2H), 3.40 (m, 1H) 3.63 (m, 3H), 3.93 (s, 2H), 7.38 (m, 5H). LRMS APCI m/z 370 [MH]$^+$

Step C

Tert-butyl 2-benzyl-9-methyl-4-{[(trifluoromethyl)sulfonyl]oxy}-5,6,8,9-tetrahydro-7H-pyrimido[4,5-d]azepine-7-carboxylate

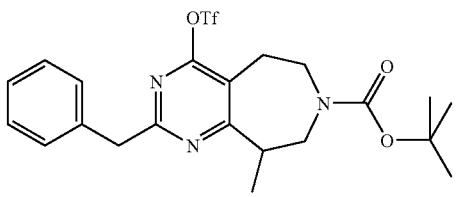

The title compound was prepared by a similar method to that of Preparation 1, Step B starting from the pyrimidinone of step B, yielding 100% of title compound.

$^1$H NMR (400 MHz, CDCl$_3$) δ: 1.30 (d, 3H), 1.47 (s, 9H), 2.93 (m, 2H), 3.38 (m, 1H), 3.61 (m, 4H), 4.19 (s, 2H), 7.39 (m, 5H). LRMS APCI m/z 446 [M-$^t$BuH]$^+$

Step D

Tert-butyl 2-benzyl-9-methyl-5,6,8,9-tetrahydro-7H-pyrimido[4,5-d]azepine-7-carboxylate

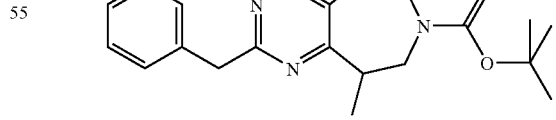

The title compound was prepared by a similar method to that of Preparation 2, Step D, starting from the triflate of Step C, yielding 55% of the title compound.

$^1$HNMR (CDCl3, 44 MHz) δ: 1.31 (d, 3H), 1.43 (s, 9H), 2.76 (m, 1H), 2.91 (m, 1H), 3.22 (m, 1H), 3.40-3.60 (m, 4H), 4.22 (s, 2H), 7.20 (m, 1H), 7.31 (m, 2H), 7.39 (m, 2H), 8.31 (s, 1H). LRMS APCI m/z 354 [MH]$^+$

Preparation 20

Step A

Tert-butyl (4E)-4-[(dimethylamino)methylene]-5-oxoazepane-1-carboxylate

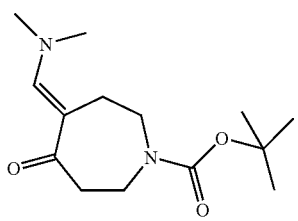

1-Tert-butyl 4-ethyl 5-oxoazepane-1,4-dicarboxylate (1 g, 5 mmol) was dissolved in dimethylformamide dimethyl acetal (15 ml) and the mixture stirred at reflux for 16 h. The reaction mixture was concentrated in vacuo to yield 1.1 g of crude vinalogous amide, which taken on for pyrimidine formation without further purification.

Step B

Tert-butyl N-[2-(2-chlorophenyl)ethyl]-6,7,8,9-tetrahydro-5H-pyrimido[4,5-d]azepine-7-carboxylate

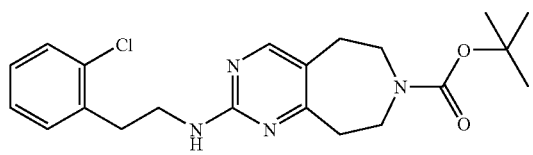

To a solution of the crude vinalogous amide from step A (100 mg, 0.38 mmol) in ethanol (6 ml) was added N-2-(2-chlorophenyl)ethyl-guanidine hydrochloride (0.41 mmol) and potassium carbonate (0.41 mmol). The reaction mixture heated at reflux for 16 h. The reaction mixture was concentrated in vacuo and residue partitioned between water and ethyl acetate. Organic layer was separated and dried over magnesium sulfate and concentrated in vacuo. The residue was then purified by column chromatography, eluting with 0 to 10% MeOH:DCM.60%

$^1$H NMR (400 MHz, CD$_3$OD) δ: 1.40 (s, 9H), 2.69 (m, 2H), 2.90 (m, 2H), 3.05 (m, 2H), 3.51 (m, 2H), 3.63 (m, 5H), 7.18 (m, 2H), 7.26 (m, 1H), 7.37 (m, 1H), 7.96 (s, 1H).

LRMS APCI m/z 403 [MH]$^+$

Preparation 21

Tert-butyl N-methyl,N-benzyl-6,7,8,9-tetrahydro-5H-pyrimido[4,5-d]azepine-7-carboxylate

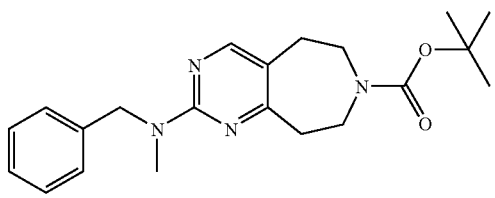

The title compound was prepared in 58% yield by a similar method to that of Preparation 20, Step B, starting from 1-benzyl-1-methyl guanidine and tert-butyl (4E)-4-[(dimethylamino)methylene]-5-oxoazepane-1-carboxylate from Preparation 20, Step A.

$^1$H NMR (400 MHz, CD$_3$OD) δ: 1.40 (s, 9H), 2.71 (m, 2H), 2.97 (m, 2H), 3.05 (s, 3H), 3.56 (m, 2H), 3.69 (m, 2H), 4.26 (s, 2H), 7.21-7.35 (m, 5H), 8.03 (s, 2H). LRMS APCI m/z 369 [MH]$^+$

Preparation 22

Tert-butyl N,N-dimethyl-6,7,8,9-tetrahydro-5H-pyrimido[4,5-d]azepine-7-carboxylate

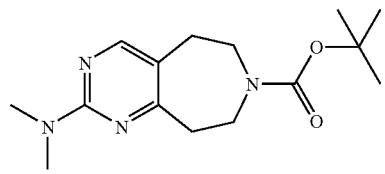

The title compound was prepared in 47% yield by a similar method to that of Preparation 20, Step B, starting from N,N-dimethyl guanidine and tert-butyl (4E)-4-[(dimethylamino)methylene]-5-oxoazepane-1-carboxylate from Preparation 20, Step A.

$^1$H NMR (400 MHz, CD$_3$OD) δ:1.40 (s, 9H), 2.68 (m, 2H), 2.98 (m, 2H), 3.17 (s, 6H), 3.51 (m, 2H), 3.69 (m, 2H), 8.03 (s, 1H). LRMS APCI m/z 293 [MH]$^+$

Preparation 23

Step A

Ethyl 2-benzyl 4-oxo-5,6,8,9-tetrahydro-7H-pyrimido[4,5-d]azepine-7-carboxylate

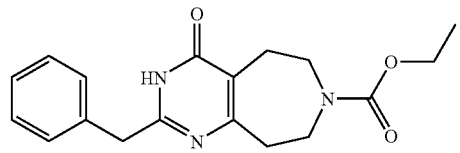

The title compound was prepared by a similar method to Preparation 1, Step A, except that diethyl 5-oxoazepane-1,4-dicarboxylate (see J Het. Chem., 1992, 29(4), 779-86) was used instead of 1-benzyl 4-ethyl 5-oxoazepane-1,4-dicarboxylate.

82%; $^1$H NMR 400 MHz, CDCl$_3$ δ: 1.14 (t, 3H), 2.64 (m, 2H), 2.80 (m, 2H), 3.42 (m, 2H), 3.52 (m, 2H), 3.79 (s, 2H), 4.04 (q, 2H), 7.26 (m, 5H). LRMS APCI m/z 328 [MH]$^+$

Step B

Ethyl 2-benzyl-4-chloro-5,6,8,9-tetrahydro-pyrimido[4,5-d]azepine-7-carboxylate

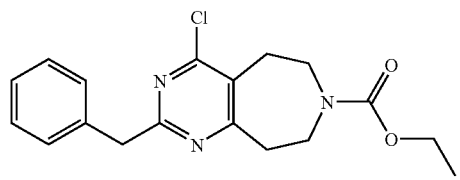

A suspension of the compound from step A (2.94 g, 8.98 mmol) in propionitrile (75 mL) was treated with phosphoryl chloride (12.6 mL) and tetrabutylammonium chloride (4.46 g, 26.9 mmol) and the mixture heated at 100° C. for 1.5 h. The reaction mixture was evaporated to dryness and the brown residue partitioned between dichloromethane (50 mL) and water (30 mL). The organic phase was dried over magnesium sulphate and evaporated in vacuo to afford the title compound as an orange gum in 100% yield, 3.29 g.

$^1$H NMR (400 MHZ, CDCl$_3$) δ: 1.25 (t, J 7 Hz, 3H), 3.10 (m, 2H), 3.18 (m, 2H), 3.70 (m, 4H), 4.15 (m, 4H), 7.25 (m, 3H), 7.40 (m, 2H); LRMS APCI m/z 346 [MH]$^+$

Step C

2-Benzyl-4-[(1-methyl-1H-pyrazol-4-ylmethyl)-amino]-5,6,8,9-tetrahydro-pyrimido[4,5-d]azepine-7-carboxylic acid ethyl ester

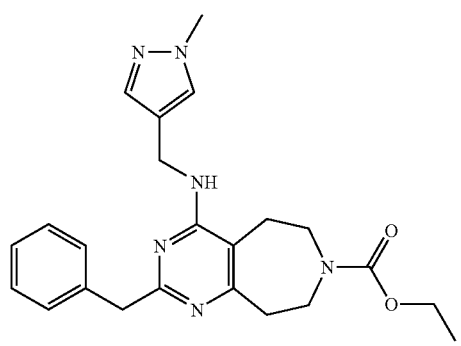

A solution of ethyl 2-benzyl-4-chloro-5,6,8,9-tetrahydro-pyrimido[4,5-d]azepine-7-carboxylate of Step B (50 mg, 0.14 mmol), triethylamine (0.10 ml, 0.72 mmol) and C-(1-Methyl-1H-pyrazol-4-yl)-methylamine (50 mg, 0.45 mmol) in N,N-dimethylacetamide (2.0 ml) was stirred for 18 h at 60° C. The solvent was removed in vacuo and the crude product was deprotected without further purification. LRMS APCI m/z 421 [MH]+.

Preparation 24

Ethyl 2-benzyl-4-ethyl-,5,6,8,9-tetrahydro7H-pyrimido[4,5-d]azepine-7-carboxylate

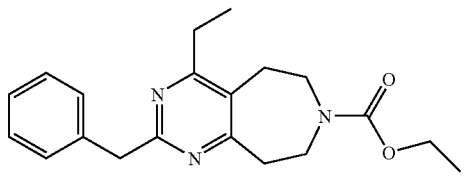

To a suspension of ethyl 2-benzyl-4-chloro-5,6,8,9-tetrahydro7H-pyrimido[4,5-d]azepine 7 carboxylate of preparation 23, Step B, (100.0 mg, 0.289 mmol)) in toluene/water (1:1, 5.0 mL) at room temperature was added ethylboronic acid (64.1 mg, 0.867 mmol). The mixture was then degassed by three vacuum/nitrogen sequences. Potassium phosphate (215.0 mg, 1.01 mmol) and tricyclohexylphosphine (9.73 mg, 0.0347 mmol) were added and the mixture degassed again. Palladium acetate (5.19 mg, 0.0231 mmol) was added and the mixture heated at 100° C. for 30 min. The reaction mixture was allowed to cool to room temperature and then poured onto water (10 mL). The mixture was extracted with ethyl acetate (3×15 mL) and the combined extracts dried over magnesium sulphate, filtered (over a pad of Arbocel) and concentrated in vacuo to give the title compound as a pale yellow gum in 98% yield, 96.0 mg.

$^1$H NMR (400 MHz, CDCl$_3$) δ: 1.24 (m, 6H), 2.81 (m, 2H), 2.90 (m, 2H), 3.09 (m, 2H), 3.63 (m, 4H), 4.19 (m, 4H), 7.20 (m, 1H), 7.28 (m, 2H), 7.40 (m, 2H); LRMS APCI m/z 340 [MH]$^+$

Preparation 25

Ethyl 2-benzyl-4-cyclopropyl-5,6,8,9-tetrahydro-7H-pyrimido[4,5-d]azepine-7-carboxylate

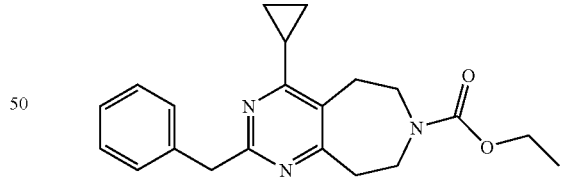

The title compound was prepared according to the method of Preparation 24 starting from the product of Preparation 23, Step B, and cyclopropylboronic acid. The title compound was obtained as a pale yellow gum in 113% yield, 115 mg.

$^1$HNMR (400 MHz, CDCl$_3$) δ: 1.00 (m, 2H), 1.15 (m, 2H), 1.27 (t, 3H), 2.07 (m, 1H), 3.08 (m, 4H), 3.66 (m, 4H), 4.16 (m, 4H), 7.19 (m, 1H), 7.27 (m, 2H), 7.37 (m, 2H);

LRMS APCI m/z 352 [MH]$^+$

Preparation 26
Step A

Benzyl 2-benzyl-4-oxo-5,6,8,9-tetrahydro-7H-pyrimido[4,5-d]azepine-7-carboxylate

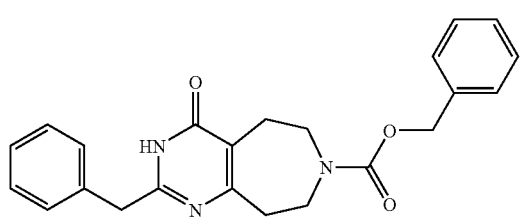

To a solution of 1-benzyl 4-ethyl 5-oxoazepane-1,4-dicarboxylate (4.5 g, 14 mmol) in MeOH (30 ml) was added benzyl amidine hydrochloride (3.1 g, 18 mmol) and NaOMe (2.3 g, 42 mmol). The resulting solution was stirred at room temperature for 16 h. The reaction mixture was concentrated under reduced pressure and residue partitioned between sat. $NH_4Cl$ (aq) and ethyl The combined organic layers were combined, dried over $MgSO_4$, filtered and concentrated in vacuo. The residue was purified by column chromatography eluting with ethyl actate/pentane (1:3 to 1:1). The relevant fraction were combined and concentrated in vacuo to afford the title compound as a colourless oil (31 mgs, 41% yield).

The organic layer was dried over magnesium sulfate and concentrated in vacuo to yield the crude piperidone, which was further purified by trituration with diethyl ether (×2) 89%;

$^1$H NMR (400 MHz, CDCl$_3$) δ: 2.86 (m, 2H), 2.95 (m, 2H), 3.62 (m, 2H), 3.67 (m, 2H), 3.91 (s, 2H), 5.19 (s, 2H), 7.25-7.40 (m, 10H). LRMS APCI m/z 390 [MH]$^+$

Step B

Benzyl 2-benzyl-4-chloro-5,6,8,9-tetrahydro-7H-pyrimido[4,5-d]azepine-7-carboxylate

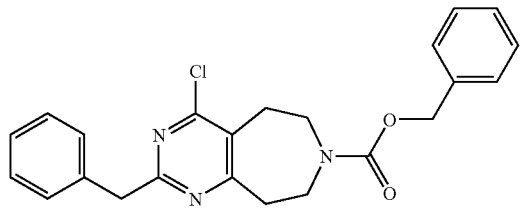

To a suspension of the product from step A (4 g, 10 mmol) in acetonitrile (100 ml) was added N,N-dimethylaniline (1.4 ml, 11.3 mmol), followed by careful addition of POCl$_3$ (9.6 ml, 100 mmol). The resulting brown solution was heated at 80° C. for 4 h. The reaction mixture was concentrated in vacuo, azeotroped with PhMe (×2) and DCM. The residue was partitioned between 2 N HCl and ethyl acetate. The organic layer was dried over magnesium sulfate and concentrated in vacuo to yield 3.5 g (84%) of title compound as brown oil, which solidified on standing.

$^1$H NMR (400 MHz, CDCl$_3$) δ: 3.09 (m, 4H), 3.66 (m, 4H), 4.13 (s, 2H), 5.15 (s, 2H), 7.18-7.37 (m, 10H). LRMS APCI m/z 408 [MH]$^+$

Preparation 27

2-Benzyl-4-imidazol-1-yl-5,6,8,9-tetrahydro-pyrimido[4,5-d]azepine-7-carboxylic acid benzyl ester

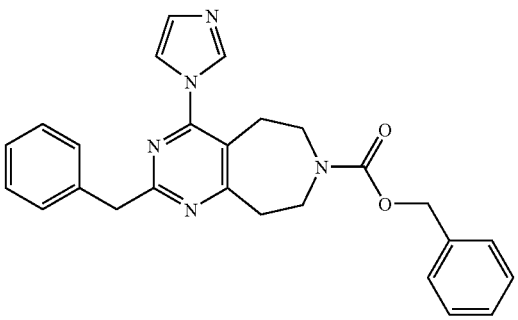

A solution of benzyl 2-benzyl-4-chloro-5,6,8,9-tetrahydro-7H-pyrimido[4,5-d]azepine-7-carboxylate of preparation 26, Step B, (0.100 g, 0.245 mmol) and imidazole (0.167 g, 2.45 mmol) in 1-methylpyrrolidinone (5 ml) was stirred at 120° C. for 18 h. The reaction solution was cooled to room temperature, poured into ethyl acetate (50 ml) and cyclohexane (50 ml), washed three times with water, dried over MgSO$_4$, filtered and concentrated in vacuo to give the crude product which was used without further purification.

$^1$H-NMR (400 MHz, DMSO-d$_6$) δ: 2.88 (m, 2H), 3.19 (m, 2H), 3.62 (m, 4H), 4.13 (s, 2H), 5.05 (s, 2H), 7.10 (s, 1H), 7.20 (m, 1H), 7.30 (m, 9H), 7.50 (s, 1H), 8.00 (s, 1H);
LRMS ESI m/z 440 [MH]+.

Preparation 28
Step A

7-Benzyl-2-(3-chlorobenzyl)-3,5,6,7,8,9-hexahydro-4H-pyrimido[4,5-d]azepin-4-one

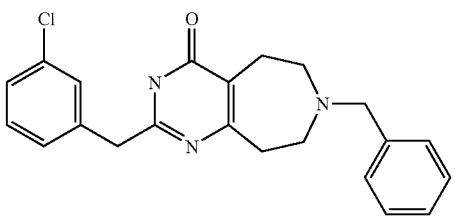

Ethanol (30 ml) was cooled in an ice bath then sodium (160 mg, 6.70 mmol) was added, with vigorous stirring. Once the sodium was dissolved, 2-(3-chlorophenyl)ethanimidamide (474 mg, 2.81 mmol) and ethyl 1-benzyl-5-oxoazepane-4-carboxylate (876 mg, 2.81 mmol) was added. The reaction mixture was refluxed, under nitrogen, for 17 h. Water (2 ml) was added to quench the reaction then the reaction mixture was concentrated in vacuo. The residue was partitioned between ethyl acetate (20 ml) and water (20 ml). The organic phase was dried over magnesium sulphate and concentrated in vacuo. Trituration of the residue with diethyl ether afforded the title compound as a solid in 33% yield, 361 mg.

$^1$HNMR (400 MHz, CDCl$_3$) δ: 2.60 (m, 2H), 2.65 (m, 2H), 2.88 (m, 2H), 2.94 (m, 2H), 3.65 (s, 2H), 3.89 (s, 2H), 7.24-7.34 (m, 9H).
LRMS APCI m/z 380 [MH]$^+$

Step B

7-Benzyl-4-chloro-2-(3-chlorobenzyl)-6,7,8,9-tetrahydro-5H-pyrimido[4,5-d]azepine

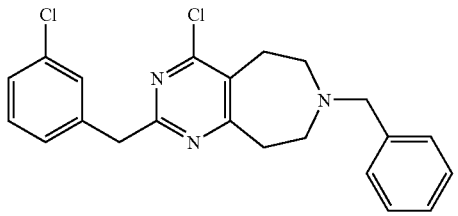

Phosphoryl chloride (1.33 ml, 14.3 mmol) and tetra-ethyl ammonium chloride (472 mg, 2.85 mmol) were added to a solution of the product of Step A (361 mg, 0.95 mmol) in propionitrile (10 ml) and heated to 100° C. for 17 h. The reaction mixture was concentrated in vacuo then azeotroped with toluene then dichloromethane. The residue was partitioned between dichloromethane (30 ml) and water (20 ml), stirred for 30 min then the organic layer was separated, dried over magnesium sulphate and concentrated in vacuo to give the title compound as a foam in 87.7% yield, 332 mg.

$^1$HNMR (400 MHz, CDCl$_3$) δ: 2.74 (m, 2H), 3.17 (m, 1H), 3.44 (m, 1H), 3.73 (m, 2H), 3.88 (m, 1H), 4.12 (s, 2H), 4.20 (m, 1H), 4.24 (s, 2H), 7.21-7.26 (m, 4H), 7.47 (m, 3H), 7.59 (m, 2H).

LRMS APCI m/z 398 [MH]$^+$

Step C

7-Benzyl-2-(3-chlorobenzyl)-6,7,8,9-tetrahydro-5H-pyrimido[4,5-d]azepine

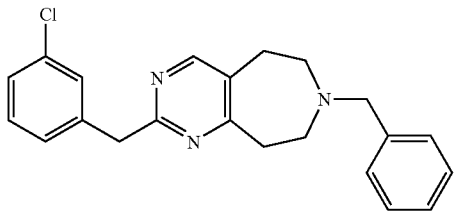

Zinc dust (943 mg, 14.4 mmol) was added to a mixture of the product from Step B (221 mg, 0.56 mmol) and 0.880 ammonia (20 ml) in tetrahydrofuran (5 ml). This was heated to reflux for 5 h. The reaction mixture was filtered then filtrate was extracted with ethyl acetate (15 ml). The organic phase was dried over magnesium sulphate and concentrated in vacuo. The residue was purified by column chromatography on a silica cartridge, eluting with DCM:MeOH (100:0 to 95:5), to afford the title compound as a pale orange oil in 66.9% yield, 135 mg.

$^1$HNMR (400 MHz, CDCl$_3$) δ: 2.91 (m, 4H), 3.04 (m, 2H), 3.33 (m, 2H), 3.89 (s, 2H), 4.41 (s, 2H), 7.41-7.57 (m, 9H), 8.53 (s, 1H); LRMS APCI m/z 364 [MH]$^+$

Preparation 29
Step A

7-Benzyl-2-(4-chlorobenzyl)-3,5,6,7,8,9-hexahydro-4H-pyrimido[4,5-d]azepin-4-one

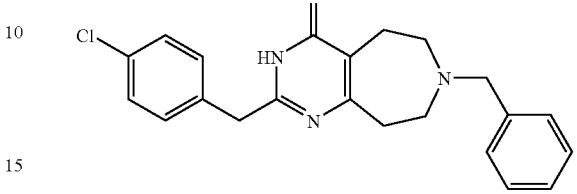

The title compound was obtained according to a similar method to that of Preparation 28, Step A, starting from 2-(4-chlorophenyl)ethanimidamide. Purification by column chromatography on Biotage 40S cartridge, eluting with DCM:MeOH (100:0 to 95:5), afforded the title compound as a pale brown foam in 16% yield, 200 mg.

$^1$HNMR (400 MHz, CDCl$_3$) δ: 2.60 (m, 4H), 2.87 (m, 4H), 3.62 (s, 2H), 3.86 (s, 2H), 7.22-7.32 (m, 9H); LRMS APCI m/z 380 [MH]$^+$

Step B

7-Benzyl-4-chloro-2-(4-chlorobenzyl)-6,7,8,9-tetrahydro-5H-pyrimido[4,5-d]azepine

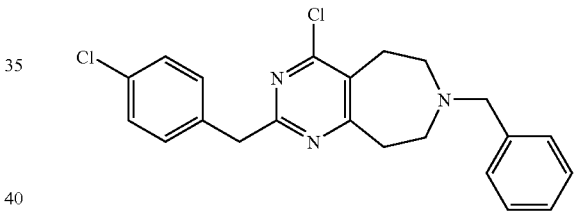

The title compound was obtained as a foam in 100% yield, 247 mg, according to a similar method to that of Preparation 28, Step B, starting from 7-benzyl-2-(4-chlorobenzyl)-3,5,6,7,8,9-hexahydro-4H-pyrimido[4,5-d]azepin-4-one of Step A.

$^1$HNMR (400 MHz, CDCl$_3$) δ: 2.74 (m, 4H), 3.21 (m, 1H), 3.37 (m, 1H), 3.75 (m, 1H), 3.93 (m, 1H), 4.12 (s, 2H), 4.25 (s, 2H), 7.26 (m, 5H), 7.49 (m, 4H); LRMS APCI m/z 398 [MH]$^+$

Step C

7-Benzyl-2-(4-chlorobenzyl)-6,7,8,9-tetrahydro-5H-pyrimido[4,5-d]azepine

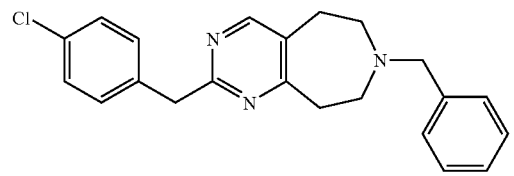

The title compound was obtained as a foam in 100% yield, 247 mg, according to a similar method to that of Preparation 28, Step C, starting from 7-benzyl-4-chloro-2-(4-chlorobenzyl)-6,7,8,9-tetrahydro-5H-pyrimido[4,5-d]azepine of Step B. Purification by column chromatography on a silica cartridge, eluting with DCM:MeOH (100:0 to 95:5), afforded the title compound as a pale orange oil in 34% yield, 66 mg.

¹HNMR (400 MHz, CDCl₃) δ: 2.70 (m, 4H), 2.83 (m, 2H), 3.11 (m, 2H), 3.72 (s, 2H), 4.17 (s, 2H), 7.23-7.36 (m, 9H), 8.30 (s, 1H); LRMS APCI m/z 364 [MH]⁺

Preparation 30
Step A

7-Benzyl-2-(1-phenylethyl)-3,5,6,7,8,9-hexahydro-4H-pyrimido[4,5-d]azepin-4-one

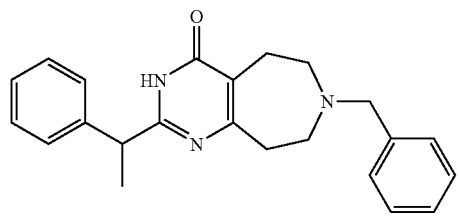

The title compound was obtained according to a similar method to that of Preparation 28, Step A, starting from 2-phenylpropanimidamide of Preparation 2. Purification by column chromatography on Biotage 40S cartridge, eluting with DCM:MeOH (100:0 to 95:5), afforded the title compound as an orange foam in 24% yield, 909 mg.

¹HNMR (400 MHz, CDCl₃) δ: 1.62 (d, 3H), 2.59 (m, 4H), 2.82 (m, 2H), 2.94 (m, 2H), 3.63 (s, 2H), 3.97 (q, 1H), 7.25-7.33 (m, 10H); LRMS APCI m/z 360 [MH]⁺

Step B

7-Benzyl-4-chloro-2-(1-phenylethyl)-6,7,8,9-tetrahydro-5H-pyrimido[4,5-d]azepine

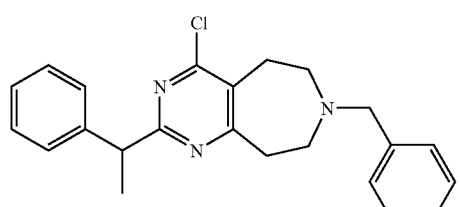

A similar method to that of Preparation 28, Step B, starting from the product of Step A yielded the title compound as a foam in 100% yield, 1.15 g.

¹HNMR (400 MHz, CDCl₃) δ: 1.68 (d, 3H), 2.79 (m, 2H), 3.32 (m, 2H), 3.57 (m, 2H), 3.75 (m, 1H), 3.91 (m, 1H), 4.26 (s, 2H), 4.34 (q, 1H), 7.19-7.30 (m, 4H), 7.37 (m, 2H), 7.51 (m, 4H); LRMS APCI m/z 378 [MH]⁺

Preparation 31
Step A

7-Benzyl-2-(2-fluorobenzyl)-3,5,6,7,8,9-hexahydro-4H-pyrimido[4,5-d]azepin-4-one

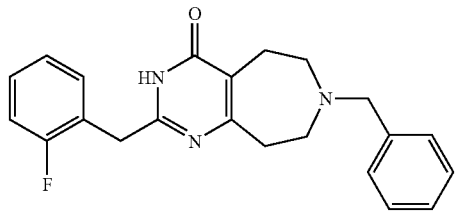

The title compound was obtained according to a similar method to that of Preparation 28, Step A, starting from 2-(2-fluorophenyl)ethanimidamide. Purification by column chromatography on silica cartridge, eluting with DCM:MeOH (94:6) afforded the title compound as a brown foam in 11% yield, 136 mg ¹HNMR (400 MHz, CDCl₃) δ: 2.60 (m, 4H), 2.85 (m, 4H), 3.63 (s, 2H), 3.97 (s, 2H), 7.13-7.34 (m, 9H); LRMS APCI m/z 364 [MH]⁺

Step B

7-Benzyl-4-chloro-2-(2-fluorobenzyl)-6,7,8,9-tetrahydro-5H-pyrimido[4,5-d]azepine

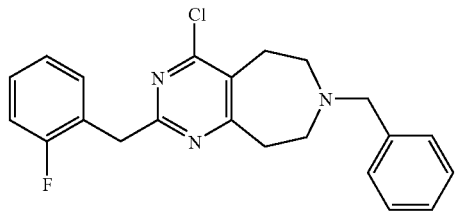

The title compound was obtained as a brown foam in 95% yield, 136 mg, according to a similar method to that of Preparation 28, Step B, starting from the product of Step A.

¹HNMR (400 MHz, CDCl₃) δ: 2.72 (m, 2H), 3.19 (m, 1H), 3.53 (m, 1H), 3.72 (m, 3H), 3.90 (m, 1H), 4.22 (s, 2H), 4.27 (s, 2H), 7.08 (m, 2H), 7.24 (m, 2H), 7.52 (m, 5H);
LRMS APCI m/z 382 [MH]⁺

Preparation 32
Step A

7-Benzyl-2-(3-fluorobenzyl)-3,5,6,7,8,9-hexahydro-4H-pyrimido[4,5-d]azepin-4-one

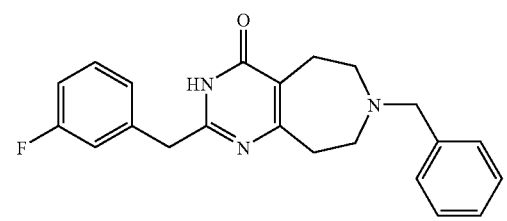

The title compound was obtained as a brown foam in 19% yield, 135 mg, according to a similar method to that of Preparation 28, Step A, starting from 2-(3-fluorophenyl)ethanimidamide.

$^1$HNMR (400 MHz, CDCl$_3$) δ: 2.60 (m, 4H), 2.87 (m, 4H), 3.64 (s, 2H), 3.91 (s, 2H), 7.00-7.34 (m, 9H); LRMS APCI m/z 364 [MH]$^+$

Step B

7-Benzyl-4-chloro-2-(3-fluorobenzyl)-6,7,8,9-tetrahydro-5H-pyrimido[4,5-d]azepine

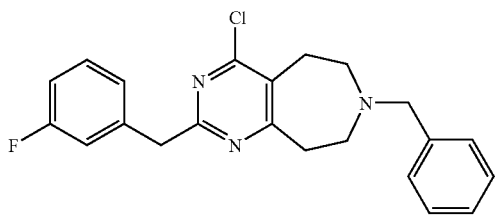

A similar method to that of Preparation 28, Step B, starting from the product of Step A yielded the title compound as a brown foam in 67% yield, 157 mg.

$^1$HNMR (400 MHz, CDCl$_3$) δ: 2.70 (m, 2H), 3.24 (m, 1H), 3.51 (m, 1H), 3.74 (m, 3H), 3.91 (m, 1H), 4.23 (s, 2H), 4.30 (s, 2H), 6.83-6.45 (m, 9H); LRMS APCI m/z 382 [MH]$^+$

Preparation 33
Step A

7-Benzyl-2-(4-fluorobenzyl)-3,5,6,7,8,9-hexahydro-4H-pyrimido[4,5-d]azepin-4-one

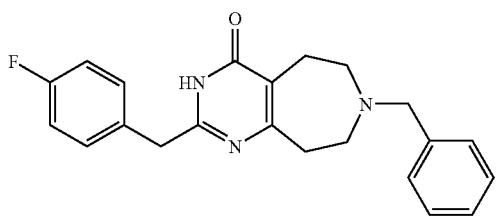

A similar method to that of Preparation 28, Step A, using 2-(4-fluorophenyl)ethanimidamide afforded the title compound as a light brown solid in 19% yield, 253 mg $^1$HNMR (400 MHz, CDCl$_3$) δ: 2.59 (m, 4H), 2.91 (m, 4H), 3.64 (s, 2H), 3.91 (s, 2H), 7.05 (m, 2H), 7.25-7.38 (m, 7H); LRMS APCI m/z 364 [MH]$^+$ Step B 7-Benzyl-4-chloro-2-(4-fluorobenzyl)-6,7,8,9-tetrahydro-5H-pyrimido[4,5-d]azepine

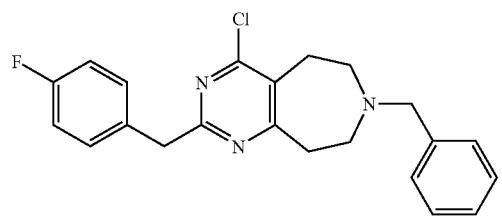

A similar method to that of Preparation 28, Step B, starting from the product of Step A afforded the title compound as a brown foam in 77% yield, 206 mg.

$^1$HNMR (400 MHz, CDCl$_3$) δ: 2.72 (m, 2H), 3.15 (m, 1H), 3.45 (m, 1H), 3.72 (m, 3H), 3.85 (m, 1H), 4.11 (s, 2H), 4.24 (s, 2H), 6.97 (m, 2H), 7.07-7.30 (m, 3H), 7.46 (m, 2H), 7.58 (m, 2H); LRMS APCI m/z 382 [MH]$^+$

Preparation 34
Step A

7-Benzyl-2-[3-(trifluoromethyl)benzyl]-3,5,6,7,8,9-hexahydro-4H-pyrimido[4,5-d]azepin-4-one

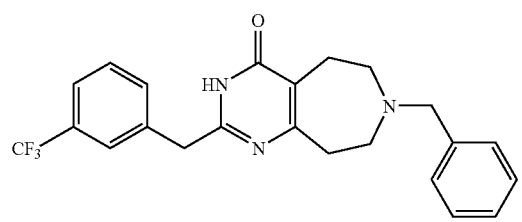

A similar method to that of Preparation 28, Step A, using 2-[3-(trifluoromethyl)phenyl]ethanimidamide afforded the title compound as a light brown solid in 13% yield, 126 mg $^1$HNMR (400 MHz, CD$_3$OD) δ: 2.60 (m, 4H), 2.83 (m, 4H), 3.65 (s, 2H), 3.97 (s, 2H), 7.25-7.36 (m, 5H), 7.49-7.60 (m, 4H); LRMS APCI m/z 414 [MH]$^+$ Step B 7-Benzyl-4-chloro-2-[3-(trifluoromethyl)benzyl]-6,7,8,9-tetrahydro-5H-pyrimido[4,5-d]azepine

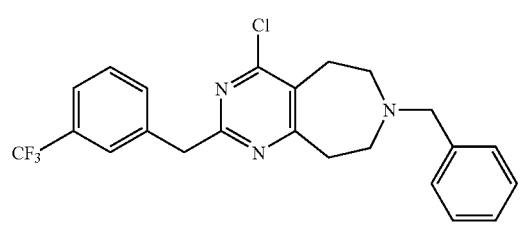

A similar method to that of Preparation 28, Step B, starting from 7-benzyl-2-[3-(trifluoromethyl)benzyl]-3,5,6,7,8,9-hexahydro-4H-pyrimido[4,5-d]azepin-4-one of Step A afforded the title compound as a brown foam in quantitative yield, 147 mg.

¹HNMR (400 MHz, CDCl₃) δ: 2.64 (m, 2H), 3.15 (m, 1H), 3.44 (m, 1H), 3.79 (m, 3H), 3.98 (m, 1H), 4.28 (s, 2H), 4.46 (s, 2H), 6.72 (m, 2H), 7.47 (m, 4H), 6.60 (m, 4H);
LRMS APCI m/z 432 [MH]⁺

Preparation 35
Step A

7-Benzyl-2-(4-methylbenzyl)-3,5,6,7,8,9-hexahydro-4H-pyrimido[4,5-d]azepin-4-one

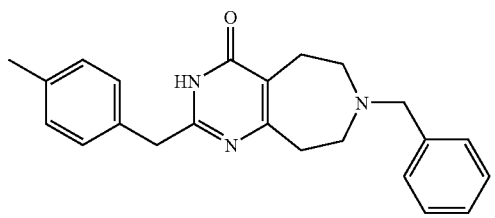

Under nitrogen, 2-(4-methylphenyl)ethanimidamide hydrochloride (360 mg, 1.95 mmol) and ethyl 1-benzyl-5-oxoazepane-4-carboxylate hydrochloride (500 mg, 1.61 mmol) were added to a freshly-prepared solution of sodium ethoxide (from sodium (120 mg, 5.22 mmol) dissolved in ethanol (15 ml)) and the mixture refluxed overnight. The reaction mixture was concentrated in vacuo and the residue treated with water. The mixture was acidified with 2M HCl solution, then rebasified using saturated aqueous NaHCO₃ solution and extracted with dichloromethane. The dichloromethane extract was dried over magnesium sulphate and concentrated in vacuo. The residue was purified by purified by column chromatography on silica gel, eluting with DCM:MeOH, 98:2 to 94:6, to afford the title compound as a solid in 43% yield, 250 mg.

¹HNMR (400 MHz, CD₃OD) δ: 2.29 (s, 3H), 2.57 (m, 2H), 2.64 (m, 2H), 2.81 (m, 2H), 2.91 (m, 2H), 3.64 (s, 2H), 3.83 (s, 2H), 7.11-7.38 (m, 9H); LRMS m/z 360 [MH]⁺

Step B

7-Benzyl-4-chloro-2-(4-methylbenzyl)-6,7,8,9-tetrahydro-5H-pyrimido[4,5-d]azepine

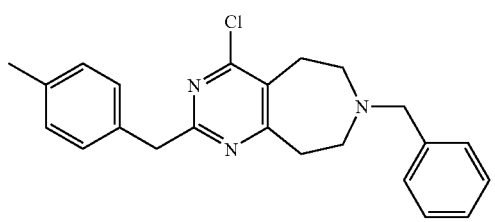

A similar method to that of Preparation 28, Step B, starting from 7-benzyl-2-(4-methylbenzyl)-3,5,6,7,8,9-hexahydro-4H-pyrimido[4,5-d]azepin-4-one of Step A, except that purification of the residue was carried out by column chromatography on silica gel, eluting with dichloromethane:diethyl ether, 4:1, then 2:1 to afford the title compound as a gum in 79% yield, 150 mg.

¹HNMR (400 MHz, CD₃OD) δ: 2.27 (s, 3H), 2.67 (m, 4H), 3.12 (m, 4H), 3.64 (s, 2H), 4.06 (s, 2H), 7.06-7.36 (m, 9H); LRMS m/z 378,380 [MH]⁺

Preparation 36
Step A

7-Benzyl-2-(3-methylbenzyl)-3,5,6,7,8,9-hexahydro-4H-pyrimido[4,5-d]azepin-4-one

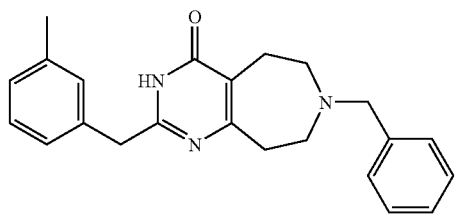

A similar method to that of Preparation 35, Step A, starting from 2-(3-methylphenyl)ethanimidamide hydrochloride afforded the title compound as a solid in 33% yield, 225 mg.

¹HNMR (400 MHz, CD₃OD) δ: 2.30 (s, 3H), 2.58 (m, 2H), 2.64 (m, 2H), 2.81 (m, 2H), 2.91 (m, 2H), 3.64 (s, 2H), 3.83 (s, 2H), 7.05-7.35 (m, 9H); LRMS m/z 360 [MH]⁺

Step B

7-Benzyl-4-chloro-2-(3-methylbenzyl)-6,7,8,9-tetrahydro-5H-pyrimido[4,5-d]azepine

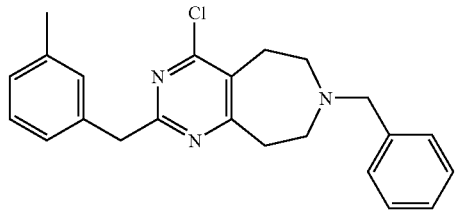

A similar method to that of Preparation 28, Step B, starting from 7-Benzyl-2-(3-methylbenzyl)-3,5,6,7,8,9-hexahydro-4H-pyrimido[4,5-d]azepin-4-one of Step A, afforded the title compound as a gum in 94% yield, 149 mg.

¹HNMR (400 MHz, CD₃OD) δ: 2.28 (s, 3H), 2.67 (m, 4H), 3.13 (m, 4H), 3.65 (s, 2H), 4.06 (s, 2H), 7.00-7.15 (m, 4H), 7.22-7.35 (m, 5H); LRMS m/z 378,380 [MH]⁺

Preparation 37
Step A

7-Benzyl-2-(2-methylbenzyl)-3,5,6,7,8,9-hexahydro-4H-pyrimido[4,5-d]azepin-4-one

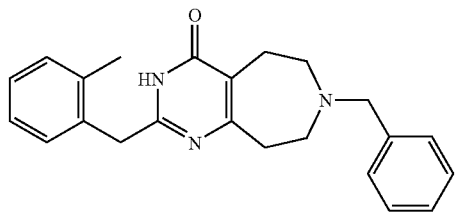

A similar method to that of Preparation 35, Step A, starting from 2-(2-methylphenyl)ethanimidamide hydrochloride afforded the title compound as a solid in 33% yield, 230 mg.

¹HNMR (400 MHz, CD₃OD) δ: 2.31 (s, 3H), 2.60 (m, 2H), 2.65 (m, 2H), 2.83 (m, 2H), 2.89 (m, 2H), 3.65(s, 2H), 3.92 (s, 2H), 7.03-7.36 (m, 9H); LRMS m/z 360 [MH]⁺

Step B

7-Benzyl-4-chloro-2-(2-methylbenzyl)-6,7,8,9-tetrahydro-5H-pyrimido[4,5-d]azepine

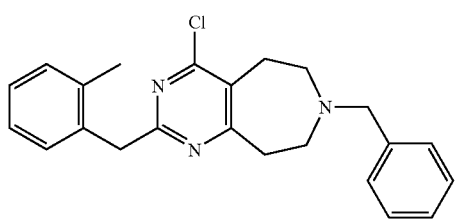

A similar method to that of Preparation 28, Step B starting from 7-Benzyl-2-(2-methylbenzyl)-3,5,6,7,8,9-hexahydro-4H-pyrimido[4,5-d]azepin-4-one afforded the title compound as a gum in 92% yield, 155 mg.

¹HNMR (400 MHz, CD₃OD) δ: 2.33 (s, 3H), 2.67 (m, 4H), 3.12 (m, 4H), 3.65 (s, 2H), 4.14 (s, 2H), 7.06-7.15 (m, 4H), 7.22-7.35 (m, 5H); LRMS m/z 378,380 [MH]⁺

Preparation 38

Step A 2,7-Dibenzyl-6,7,8,9-tetrahydro-5H-pyrimido[4,5-d]azepin-4-one

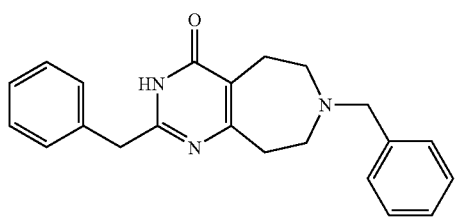

Ethanol (50 ml) was cooled in an ice bath then sodium (442 mg, 19.2 mmol) added, with vigorous stirring. Once the sodium was dissolved, 2-phenylethanimidamide (1.29 g, 9.6 mmol) and ethyl 1-benzyl-5-oxoazepane-4-carboxylate (2.5 g, 8 mmol) was added. The reaction mixture was refluxed, under nitrogen, for 17 h. Water (10 ml) was added to quench the reaction then the reaction mixture concentrated in vacuo. The residue was partitioned between ethyl acetate (200 ml) and water (200 ml). The organic phase was dried over magnesium sulphate and concentrated in vacuo. The residue was purified by column chromatography on silica gel, eluting with DCM:MeOH (98:2 to 95:5), to afford a white solid, 1.35 g, 49%

¹HNMR (400 MHz, CD₃OD) δ: 2.59 (m, 2H), 2.66 (m, 2H), 2.80 (m, 2H), 2.90 (m, 2H), 3.64 (s, 2H), 3.88 (s, 2H), 7.2-7.40 (m, 10H).

LRMS APCI m/z 346 [MH]⁺

Step B 2,7-Dibenzyl-4-chloro-6,7,8,9-tetrahydro-5H-pyrimido[4,5-d]azepine

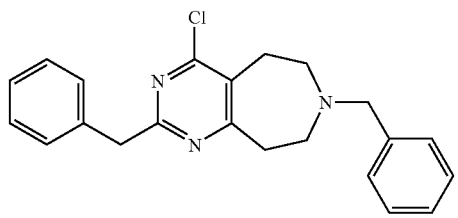

Phosphoryl chloride (5.47 ml, 58.6 mmol) and tetra-ethyl ammonium chloride (1.94 g, 11.7 mmol) were added to a solution of 2,7-dibenzyl-6,7,8,9-tetrahydro-5H-pyrimido[4,5-d]azepin-4-ol of Step A (1.35 g, 3.9 mmol) in propionitrile (40 ml) and heated to 100° C. for 17 h. The reaction mixture was concentrated in vacuo then azeotroped with toluene then dichloromethane. The residue was partitioned between dichloromethane (30 ml) and water (20 ml), stirred for 30 min then the organic layer was separated, dried over magnesium sulphate and concentrated in vacuo. The residue was purified by column chromatography on silica gel, eluting with pentane:ethyl acetate (8:2) to pentane:ethyl acetate (1:1), to afford a white solid 950 mg (67%).

¹HNMR (400 MHz, CDCl₃) δ: 2.66 (m, 4H), 3.11 (m, 4H), 3.64 (s, 2H), 4.10 (s, 2H), 7.15-7.35 (m, 10H)

LRMS APCI m/z 364 [MH]⁺

Step C 2,7-Dibenzyl-4-methoxy-6,7,8,9-tetrahydro-5H-pyrimido[4,5-d]azepine

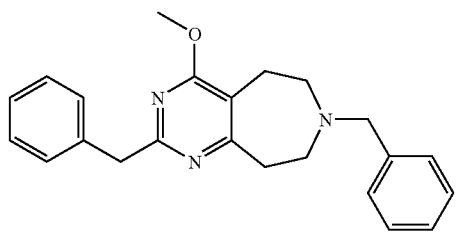

2,7-dibenzyl-4-chloro-6,7,8,9-tetrahydro-5H-pyrimido[4,5-d]azepine of Step B (86 mg, 0.23 mmol) was dissolved in methanol (10 ml) and sodium methoxide (25 mg, 0.47 mmol) was added. The reaction was refluxed under nitrogen for 16 h. The reaction mixture was concentrated in vacuo and the residue was partitioned between ethyl acetate (50 ml) and water (50 ml). The organic layer was separated, washed with brine (50 ml), dried over MgSO₄, filtered and concentrated in vacuo to afford a colourless oil, 75.5 mg, 89%.

¹HNMR (400 MHz, CD₃OD) δ:2.58 (t, 2H), 2.67 t, 2H), 2.88 (t, 2H), 3.01 (t, 2H), 3.65 (s, 2H), 3.93 (s, 3H), 7.15-7.38 (m, 10H).

LRMS APCI m/z 360 [MH]⁺

Preparation 39

2,7-Dibenzyl-4-methyl-6,7,8,9-tetrahydro-5H-pyrimido[4,5-d]azepine

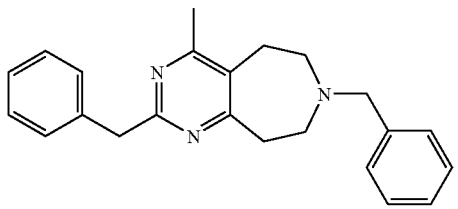

2,7-dibenzyl-4-chloro-6,7,8,9-tetrahydro-5H-pyrimido[4,5-d]azepine (70 mg, 0.193 mmol) of Preparation 38, Step B, was dissolved in dioxane (5 ml) and Caesium carbonate (251 mg, 0.77 mmol), trimethylboroxine (0.054 ml, 0.385 mmol) and Catalyst 1 (10 mg) were added. The reaction was refluxed under nitrogen for 3 h. The reaction was filtered over arbocel and diluted with ethyl acetate, washed with water, dried over MgSO$_4$ filtered and concentrated in vacuo to afford the title compound as a colourless oil in 99% yield, 66 mg.

$^1$HNMR (400 MHz, CD$_3$OD) δ: 2.47 (s, 3H), 2.65 (m, 4H), 2.95 (m, 2H), 3.10 (m, 2H), 3.64 (s, 2H), 4.10 (s, 2H), 7.15-7.40 (m, 10H); LRMS APCI m/z 344 [MH]$^+$

Preparation 40

2,7-Dibenzyl-4-butyl-6,7,8,9-tetrahydro-5H-pyrimido[4,5-d]azepine

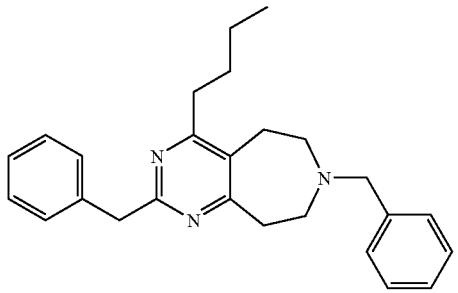

The title compound was prepared using a similar method to that of Preparation 39, starting from 2,7-dibenzyl-4-chloro-6,7,8,9-tetrahydro-5H-pyrimido[4,5-d]azepine of Preparation 38, Step B and n-butaneboronic acid. The title compound was obtained as a colourless oil 126 mg, 79%

$^1$HNMR (400 MHz, CD$_3$OD) δ: 0.92 (t, 3H), 1.37 (m, 2H), 1.57 (m, 2H), 2.64 (m, 4H), 2.79 (t, 2H), 2.96 (t, 2H), 3.10 (t, 2H), 3.64 (s, 2H), 4.12 (s, 2H), 7.15-7.40 (m, 10H); LRMS APCI m/z 386 [MH]$^+$

Preparation 41

(R)-2-(Hydroxy-phenyl-methyl)-5,6,8,9-tetrahydro-pyrimido[4,5-d]azepine-7-carboxylic acid Tert-butyl ester and (S)-2-(hydroxy-phenyl-methyl)-5,6,8,9-tetrahydro-pyrimido[4,5-d]azepine-7-carboxylic acid Tert-butyl ester

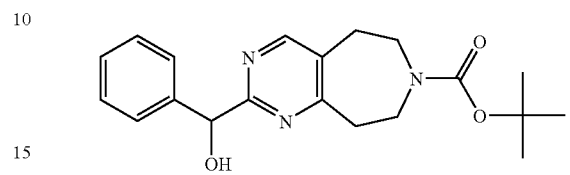

The title compounds were prepared in a manner identical to Preparation 20, step B, starting with 4-dimethylaminomethylene-5-oxo-azepane-1-carboxylic acid, tert-butyl ester (0.500 g, 1.86 mmol) and 2-hydroxy-2-phenyl-acetamidine (1.04 g, 5.59 mmol). Separation of the enantiomers by chiral prep HPLC using a Chiralcel OD-H column, elating with Hexane/IPA, gave the two products of undetermined absolute stereochemistry.

$^1$H-NMR (400 MHz, CDCl$_3$) δ: 1.46 (s, 9H), 2.82 (m, 2H), 3.13 (m, 2H), 3.60 (m, 4H), 5.80 (s, 1H), 7.25 (m, 2H), 7.29 (m, 2H), 7.48 (m, 2H); Stereoisomer 1 (24 mg, 3.6% yield): room temperature 10.179 min; Stereoisomer 2 (3 mg, 0.5% yield): room temperature 12.044 min.

Preparation 42

Step A tert-Butyl-4-oxo-2-thioxo-1,2,3,4,5,6,8,9-octahydro-7H-pyrimido[4,5-d]azepine-7-carboxylate

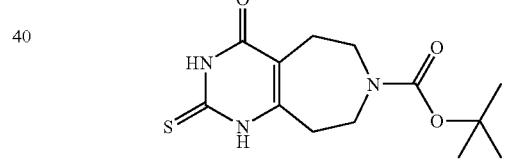

The title compound was prepared by a similar method to that of Preparation 1, Step A, starting from thiourea. The title compound was obtained as a white solid (250 g, 80% yield).

$^1$HNMR 400 MHz, CDCl$_3$, δppm: 1.45 (s, 9H), 2.65-2.83 (m, 4H), 3.52 (s, 2H), 3.76 (s, 2H), 9.40 (bs, 2H); ES+ m/z 298 [MH]$^+$.

Step B

Tert-Butyl-2,4-dichloro-5,6,8,9-tetrahydro-7H-pyrimido[4,5-d]azepine-7-carboxylate

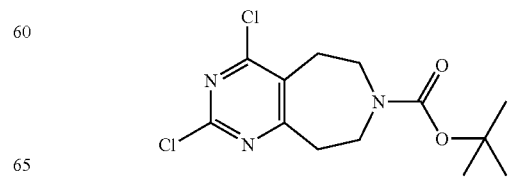

To a solution of the product from Step A (300 g, 1.01 mol) in POCl$_3$ (1500 mL) was added DMF (10 mL). The reaction mixture was heated at 90° C. until TLC analysis (EtOAc/Petroleum ether=1:2) showed the complete consumption of starting material. The excess POCl$_3$ was removed under vacuum and the residue was poured into crushed ice slowly with stirring. The pH of the aqueous solution was adjusted to 8 with solid K$_2$CO$_3$, and a solution of (Boc)$_2$O (235 g, 1.09 mol) and Et$_3$N (600 mL) in THF (1 L) was added. The reaction mixture was stirred at room temperature overnight until TLC analysis (EtOAc/Petroleum ether=1:25) showed the complete consumption of starting material. THF was removed in vacuum and the aqueous solution was extracted with CH$_2$Cl$_2$ (1 L×3). The organic layers were combined, washed with brine, dried over Na$_2$SO$_4$ and concentrated to afford crude product, which was purified by column chromatography (EtOAc/Petroleum ether=1:25) to afford (44 g, 14%) as a white solid.

$^1$HNMR 400 MHz, CDCl$_3$, δppm: 1.46 (s, 9H), 3.03-3.10 (m, 4H), 3.56 (bs, 4H)

The invention claimed is:
1. A compound of formula (I):

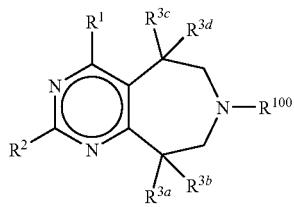

or a pharmaceutically acceptable salt thereof, wherein:
$R^1$ is H, (C$_1$-C$_4$)alkyl, fluoro(C$_1$-C$_4$)alkyl, (C$_3$-C$_6$)cycloalkyl, fluoro(C$_3$-C$_6$)cycloalkyl, fluoro(C$_1$-C$_4$)alkoxy, —NR$^4$R$^5$, —OR$^{10}$, or Het$^1$, wherein said alkyl, cycloalkyl and alkoxy are optionally substituted with one to four hydroxyl;
Het$^1$ is a 5- or 6-membered heterocyclic ring containing one nitrogen atom at the point of attachment, and comprising up to 2 further heteroatoms selected from oxygen, nitrogen and sulfur, said ring being optionally substituted with 1 to 3 groups independently selected from amino, —NH[(C$_1$-C$_4$)alkyl], —N[(C$_1$-C$_4$)alkyl]$_2$, hydroxyl, halogen, cyano, (C$_1$-C$_4$)alkyl, fluoro(C$_1$-C$_4$)alkyl, (C$_1$-C$_4$)alkoxy, fluoro(C$_1$-C$_4$)alkoxy, said alkyl and alkoxy being optionally substituted with one to four hydroxyl;
R$^2$ is —(CH$_2$)$_p$-phenyl, —CH(R$^6$)-phenyl, —C(R$^6$)$_2$-phenyl, —NR$^7$R$^8$, or —NR$^9$—(CH$_2$)$_p$-phenyl wherein in each instance the phenyl radical is optionally substituted with one to four groups independently selected from amino, —NH[(C$_1$-C$_4$)alkyl], —N[(C$_1$-C$_4$)alkyl]$_2$, hydroxyl, halogen, cyano, (C$_1$-C$_4$)alkyl, fluoro(C$_1$-C$_4$)alkyl, (C$_1$-C$_4$)alkoxy, fluoro(C$_1$-C$_4$)alkoxy, said alkyl and alkoxy being optionally substituted with one to four hydroxyl;
R$^{3a}$, R$^{3b}$, R$^{3c}$ and R$^{3d}$ are independently H, (C$_1$-C$_4$)alkyl or fluoro(C$_1$-C$_4$)alkyl;
R$^4$ is H, (C$_1$-C$_4$)alkyl or fluoro(C$_1$-C$_4$)alkyl;
R$^5$ is (C$_1$-C$_6$)alkyl, fluoro(C$_1$-C$_6$)alkyl, (C$_3$-C$_6$)cycloalkyl methylene, fluoro(C$_3$-C$_6$)cycloalkylmethyl, said alkyl and cycloalkyl being optionally substituted with one to four hydroxyl, phenyl, or —(CH$_2$)$_q$-Het$^2$;
Het$^2$ is a 5-membered heterocyclic ring containing 1 or 2 heteroatoms independently selected from nitrogen and oxygen, said ring being optionally substituted with 1 to 3 groups selected from amino, —NH[(C$_1$-C$_4$)alkyl], —N[(C$_1$-C$_4$)alkyl]$_2$, hydroxyl, halogen, cyano, (C$_1$-C$_4$)alkyl, fluoro(C$_1$-C$_4$)alkyl, (C$_1$-C$_4$)alkoxy, fluoro(C$_1$-C$_4$)alkoxy, said alkyl and alkoxy being optionally substituted with one to four hydroxyl;
each R$^6$ is independently (C$_1$-C$_4$)alkyl, fluoro(C$_1$-C$_4$)alkyl, hydroxyl, or fluorine;
when R$^2$ is —C(R$^6$)$_2$-phenyl, both R$^6$ can be taken together with the carbon to which they are attached to form a (C$_3$-C$_6$)cycloalkyl or a fluoro(C$_3$-C$_6$)cycloalkyl group;
R$^7$ is H, (C$_1$-C$_4$)alkyl, fluoro(C$_1$-C$_4$)alkyl, (C$_3$-C$_6$)cycloalkyl or fluoro(C$_3$-C$_6$)cycloalkyl;
R$^8$ is (C$_1$-C$_4$)alkyl, fluoro(C$_1$-C$_4$)alkyl, (C$_3$-C$_6$)cycloalkyl, (C$_3$-C$_6$)cycloalkylmethyl, or fluoro(C$_3$-C$_6$)cycloalkyl;
or R$^7$ and R$^8$, together with the nitrogen atom to which they are bound, form a 4- to 6-membered heterocyclic ring optionally containing one further heteroatom selected from oxygen and sulfur, said ring being optionally fused to a phenyl ring;
R$^9$ is H, (C$_1$-C$_4$)alkyl or fluoro(C$_1$-C$_4$)alkyl;
R$^{10}$ is (C$_1$-C$_4$)alkyl optionally substituted by —(C$_3$-C$_6$)cycloalkyl, —(C$_1$-C$_4$)alkoxy, —CF$_3$, —N[(C$_1$-C$_4$)alkyl]$_2$, phenyl optionally substituted by cyano, or Het$^3$;
Het$^3$ is a 5- or 6-membered heterocyclic ring containing 1 or 2 heteroatoms independently selected from nitrogen and oxygen, said ring being optionally substituted by (C$_1$-C$_4$)alkyl;
p is 1 or 2;
q is 0, 1 or 2;
and R$^{100}$ is H.

2. The compound of claim 1, or a pharmaceutically acceptable salt thereof, wherein R$^{3a}$ is H or methyl.

3. The compound of claim 2, or a pharmaceutically acceptable salt thereof, wherein each R$^{3b}$, R$^{3c}$ and R$^{3d}$ is H.

4. The compound of claim 1, or a pharmaceutically acceptable salt thereof, wherein R$^1$ is H, (C$_1$-C$_4$)alkyl, (C$_3$-C$_6$)cycloalkyl, (C$_1$-C$_4$)alkoxy, —NR$^4$R$^5$, or Het$^1$.

5. The compound of claim 1 or a pharmaceutically acceptable salt thereof, wherein Het$^1$ is a 5-or 6-membered heterocyclic ring containing one nitrogen atom at the point of attachment, and further comprising either (a) 0, 1 or 2 nitrogen atoms or (b) one oxygen atom, said ring being optionally substituted by 1 to 3 groups independently selected from amino, —NH[(C$_1$-C$_4$)alkyl], —N[(C$_1$-C$_4$)alkyl]$_2$, hydroxyl, halogen, cyano, (C$_1$-C$_4$)alkyl, fluoro(C$_1$-C$_4$)alkyl, (C$_1$-C$_4$)alkoxy, fluoro(C$_1$-C$_4$)alkoxy, said alkyl and alkoxy being optionally substituted by one to four hydroxyl.

6. The compound of claim 1, or a pharmaceutically acceptable salt thereof, wherein Het$^2$ is tetrahydrofuran-2-yl, optionally substituted by 1 to 3 groups independently selected from amino, —NH[(C$_1$-C$_4$)alkyl], —N[(C$_1$-C$_4$)alkyl]$_2$, hydroxyl, halogen, cyano, (C$_1$-C$_4$)alkyl, fluoro(C$_1$-C$_4$)alkyl, (C$_1$-C$_4$)alkoxy, or fluoro(C$_1$-C$_4$)alkoxy, said alkyl and alkoxy being optionally substituted by one to four hydroxyl.

7. The compound of claim 1 or a pharmaceutically acceptable salt thereof, wherein R$^2$ is —(CH$_2$)$_p$-phenyl, —CH(R$^6$)-phenyl, —C(R$^6$)$_2$-phenyl, or —NR$^9$—(CH$_2$)$_p$-phenyl, wherein in each instance the phenyl radical is optionally substituted by one to four groups independently selected from halogen, cyano, (C$_1$-C$_4$)alkyl, fluoro(C$_1$-C$_4$)alkyl, (C$_1$-C$_4$)alkoxy, or fluoro(C$_1$-C$_4$)alkoxy, said alkyl and alkoxy being optionally substituted by one to four hydroxyl.

8. The compound of claim 7, or a pharmaceutically acceptable salt thereof, wherein $R^2$ is benzyl.

9. The compound of claim 1 which is selected from:

2-benzyl-N,9-dimethyl-6,7,8,9-tetrahydro-5H-pyrimido [4,5-d]azepin-4-amine;

2-benzyl-4-(1 H-pyrazol-1-yl)-6,7,8,9-tetrahydro-5H-pyrimido[4,5-d]azepine;

2-(1-phenylethyl)-6,7,8,9-tetrahydro-5H-pyrimido[4,5-d] azepine;

2-(4-methylbenzyl)-6,7,8,9-tetrahydro-5H-pyrimido[4,5-d]azepine;

2-benzyl-6,7,8,9-tetrahydro-5H-pyrimido[4,5-d]azepine;

2-benzyl-4-imidazol-1-yl-6,7,8,9-tetrahydro-5H-pyrimido[4,5-d]azepine;

4-ethoxy-2-(1-phenylethyl)-6,7,8,9-tetrahydro-5H-pyrimido[4,5-d]azepine ;

2-(3-fluorobenzyl)-6,7,8,9-tetrahydro-5H-pyrimido[4,5-d]azepine;

2-benzyl-N-methyl-6,7,8,9-tetrahydro-5H-pyrimido[4,5-d]azepin-4-amine;

(2S)-2-[(2-benzyl-6,7,8,9-tetrahydro-5H-pyrimido[4,5-d] azepin-4-yl)amino]-3-methylbutan-1-ol;

2-benzyl-N-[2-(1 H-pyrazol-1 -yl)ethyl]-6,7,8,9-tetrahydro-5H-pyrimido[4,5-d]azepin-4-amine;

2-benzyl-4-morpholin-4-yl-6,7,8,9-tetrahydro-5H-pyrimido[4,5-d]azepine;

1-{[(2-benzyl-6,7,8,9-tetrahydro-5H-pyrimido[4,5-d] azepin-4-yl)amino]methyl}cyclobutanol;

[1-(2-benzyl-6,7,8,9-tetrahydro-5H-pyrimido[4,5-d] azepin-4-yl)pyrrolidin-3-yl]methanol;

2-benzyl-4-[(3S)-3-methylmorpholin-4-yl]-6,7,8,9-tetrahydro-5H-pyrimido[4,5-d]azepine;

2-benzyl-N,N-dimethyl-6,7,8,9-tetrahydro-5H-pyrimido [4,5-d]azepin-4-amine;

2-[Difluoro(phenyl)methyl]-N-methyl-6,7,8,9-tetrahydro-5H-pyrimido[4,5-d]azepin-4-amine; or 2-[difluoro (phenyl)methyl]-4-methoxy-6,7,8,9-tetrahydro-5H-pyrimido[4,5-d]azepine;

or a pharmaceutically acceptable salt thereof.

10. A pharmaceutical composition comprising a compound of formula (I) or a pharmaceutically acceptable salt thereof, as defined in claim 1, together with a pharmaceutically or veterinarily acceptable excipient.

11. A method of treating a 5-HT$_{2c}$ receptor-mediated disorder, which comprises administering to a subject in need of such treatment a therapeutically effective amount of a compound of formula (I) or a pharmaceutically acceptable salt thereof, as defined in claim 1 wherein the disorder is female sexual arousal disorder, female orgasmic disorder, hypoactive sexual desire disorder, sexual pain disorders, male erectile dysfunction (MED), benign prostatic hyperplasia, overactive bladder, lower urinary tract symptoms, psychosis, schizophrenia, schizophreniform disorder; schizoaffective disorder, delusional disorder; substance-induced psychotic disorder, personality disorder of the paranoid type, personality disorder of the schizoid type, dementia, cognitive deficit symptoms of Alzheimer's disease, attention deficit symptoms of Alzheimer's disease, multi-infarct dementia, alcoholic dementia or other drug-related dementia, dementia associated with intracranial tumors or cerebral trauma, dementia associated with Huntington's disease or Parkinson's disease, AIDS-related dementia, delirium, amnestic disorder, post-traumatic stress disorder, mental retardation, a learning disorder, attention-deficit/hyperactivity disorder, age-related cognitive decline, cognitive deficits associated with psychoses, cognitive deficits associated with schizophrenia, or anxiety, panic disorder, agoraphobia, a specific phobia, social phobia, obsessive-compulsive disorder, post-traumatic stress disorder, acute stress disorder, generalized anxiety disorder, eating disorders or obesity.

* * * * *